US007744884B2

(12) United States Patent
Elson

(10) Patent No.: US 7,744,884 B2
(45) Date of Patent: Jun. 29, 2010

(54) NEUTRALIZING ANTIBODIES AND METHODS OF USE THEREOF

(75) Inventor: Greg Elson, Collonges sous Saleve (FR)

(73) Assignee: NovImmune S.A., Geneva (CH)

( * ) Notice: Subject to any disclaimer, the term of this patent is extended or adjusted under 35 U.S.C. 154(b) by 0 days.

(21) Appl. No.: 12/004,280

(22) Filed: Dec. 19, 2007

(65) Prior Publication Data

US 2008/0118514 A1    May 22, 2008

Related U.S. Application Data

(62) Division of application No. 11/009,939, filed on Dec. 10, 2004, now Pat. No. 7,312,320.

(60) Provisional application No. 60/528,812, filed on Dec. 10, 2003, provisional application No. 60/528,811, filed on Dec. 10, 2003, provisional application No. 60/528,962, filed on Dec. 10, 2003.

(51) Int. Cl.
*A61K 39/395* (2006.01)
*A61K 39/00* (2006.01)
*C12P 21/08* (2006.01)

(52) U.S. Cl. .............. 424/144.1; 424/143.1; 424/141.1; 424/133.1; 424/142.1; 530/388.1; 530/388.2; 530/388.22; 530/387.3; 530/388.85

(58) Field of Classification Search .................. None
See application file for complete search history.

(56) References Cited

U.S. PATENT DOCUMENTS 7,271,248 B2 *   9/2007   Hardiman et al. ........ 530/387.1
2002/0192217 A1 * 12/2002  Calandra et al. ......... 424/145.1

FOREIGN PATENT DOCUMENTS

WO    WO 03/013440     2/2003
WO    WO 2005/047330   5/2005

OTHER PUBLICATIONS

O'Neill 2003. Curr. Opin in Pharm 3:396-403.*
Abdollahi-Roodsaz et al 2007. Arthritis and Rheumatism 56:2957-2967.*
Raschi et al 2008. Lupus 17:937-942.*
Akashi et al., "Cutting edge: Cell surface expression and lipopolysaccharide signaling via the Toll-like receptor 4-MD-2 complex on mouse peritoneal macrophages," J. Immunol., vol. 164(7): 3471-3475 (2000).
Akashi et al., "Lipopolysaccharide interaction with cell surface Toll-like receptor 4-MD-2: Higher affinity than that with MD-2 or CD14," J. Exp. Med., vol. 198(7): 1035-1042 (2003).
Backhed et al, "TLR4-dependent recognition of lipopolysaccharide by epithelial cells requires sCD14," Cellular Microbiology, vol. 4(8): 493-501 (2002).
Buell et al., "Blockade of human P2X7 receptor function with a monoclonal antibody." Blood 92: 3521-3528 (1998).
Devaney et al., "Neutrophil elastase up-regulates interleukin via toll-like receptor 4," FEBS Letters, vol. 544 (1-3): 129-132 (2003).
GenBank Accession No. AAH20690. I "Lymphocyte antigen 96 [*Homo sapiens*]" 2006.
GenBank Accession No. BAA78717.1 "MD-2 [*Homo sapiens*]" 1999.
GenBank Accession No. CAH72619.1 "toll-like receptor 4 [*Homo sapiens*]" 2009.
GenBank Accession No. CAH72620 "toll-like receptor 4 [*Homo sapiens*]" 2005.
GenBank Accession No. NP_056179, "MD-2 protein [*Homo sapiens*]" 2009.
GenBank Accession No. Q9Y6Y9, "RecName: Full=Lymphocyte antigen 96; AltName: Full=Protein MD-2; AltName: Full=ESPO-1; Flags: Precursor" 2009.
Ishida et al., "Hypoxia diminishes Toll-like Receptor 4 expression through reactive oxygen species generated by mitochondria in endothelial cells," J. Immunol., vol. 169(4): 2069-2075 (2002).
Johnson et al., "Activation of mammalian Toll-like receptors by endogenous agonists" Crit. Rev. Immunol., 23(1-2):15-44 (2003).
Jones and Bendig, "Rapid PCR-cloning of full-length mouse immunoglobulin variable regions." Biotechnology (N. Y.), 9: 88-89 (1991).
Kammann et al., "Rapid insertional mutagenesisof DNA by polymerase chain reaction (PCR)," Nucleic Acids Res. vol. 17: 5404 (1989).
Kawasaki et al., "Identification of mouse MD-2 residues important for forming the cell surface TLR4- MD-2 complex recognized by anti-TLR4-MD2 antibodies, and for conferring LPS and taxol responsiveness on mouse TLR4 by alanine-scanning mutagenesis," J. Immunol., vol. 170(1): 413-420 (2003).
Kirkland et al., "Analysis of Lipopolysaccharide Binding by CD14," J. Biol. Chem., vol. 268(33): 24818-24823(1993).
Kolbinger et al., "Humanization of a mouse anti-human IgE antibody: a potential therapeutic for IgE-mediated allergies" Protein Eng. 6, 971-980, 1993).
Lakhani et al., "Toll-like receptor signaling in sepsis" Curr. Opin. Pediatr. 15: 278-282 (2003).

(Continued)

*Primary Examiner*—Gary B Nickol
*Assistant Examiner*—Shulamith H Shafer
(74) *Attorney, Agent, or Firm*—Mintz Levin Cohn Ferris Glovsky and Popeo, P.C.; Ivor R. Elrifi, Esq.

(57) ABSTRACT

This invention provides monoclonal antibodies that recognize the Toll-like Receptor 4/MD-2 receptor complex, and monoclonal antibodies that recognize the TLR4/MD2 complex as well as TLR4 when not complexed with MD-2. The invention further provides methods of using the monoclonal antibodies as therapeutics. This invention also provides soluble chimeric proteins, methods of expressing and purifying soluble chimeric proteins, and methods of using soluble chimeric proteins as therapeutics, in screening assays and in the production of antibodies.

12 Claims, 26 Drawing Sheets

OTHER PUBLICATIONS

Lenhardt et al., "Activation of innate immunity in the CNS triggers neurodegeneration through a Toll like receptor 4-dependent pathway," PNAS, vol. 100(14): 8514-8519 (2003).

Miyake, "Endotoxin recognition molecules MD-2 and Toll-like Receptor 4 as potential targets for therapeutic intervention of endotoxin shock," Current Drug Targets: Inflammation and Allergy, vol. 3(3): 291-297 (2004).

Miyake, "Innate recognition of lipopolysaccharide by CD14 and toll-like receptor 4-MD-2: unique roles for MD-2," International Immunopharmacology, vol. 3(1): 1199-128 (2003).

Nijhuis et al, "Endothelial cells are main producers of Interleukin 8 through Toll-like receptor 2 and 4 signaling during bacterial infection in leukopenic cancer patients," Clinical aid Diagnostic Laboratory Immunology, vol. 10(4): 558-563 (2003).

O'Neill, "Therapeutic targeting of Toll-like receptors for inflammatory and infectious diseases" Curr. Opin. Pharmacol. 3: 396-403 (2003).

Ohashi et al., "Cutting Edge: Heat Shock Protein 60 is a Putative Endogenous Ligand of the Toll-Like Receptor-4 Complex," J. Immunol., vol. 164: 558-561 (2000).

Okamura et al., "The Extra Domain A of Fibronectin Activates Toll-like Receptor 4," J. Biol. Chem. vol. 276(13): 10229-10233 (2001).

Pasterkamp et al., "Role of Toll-like Receptor 4 in the initiation and progression of atherosclerotic disease," Eur. J. Clin. Invest., vol. 34(5): 328-334 (2004).

Pivarcsi et al., "Expression and Function of Toll-like Receptors 2 and 4 in Human Keratinocytes," International Immunology, vol. 15(6): 721-730 (2003).

Pugin et al., "Soluble MD-2 activity in plasma from patients with severe sepsis and septic shock," Blood, vol. 104(13): 4071-4079 (2004).

Sato et al., "Reshaping a human antibody to inhibit the interleukin 6-dependent tumor cell growth," Cancer Res. vol. 53: 851-856 (1993).

Shimazu et al., "MD-2, a molecule that confers lipopolysaccharide responsiveness on Toll-like receptor 4," J. Exp. Med., vol. 189(11): 1777-1782 (1999).

Takeda et al., "Toll-like receptors" Annu. Rev. Immunol., 21: 335-76 (2003).

Yang et al., "Cellular events mediated by lipopolysaccharide-stimulated Toll-like receptor 4," J. Biol. Chem., vol. 275(27): 20861-20866 (2000).

\* cited by examiner

18H10

Figure 3
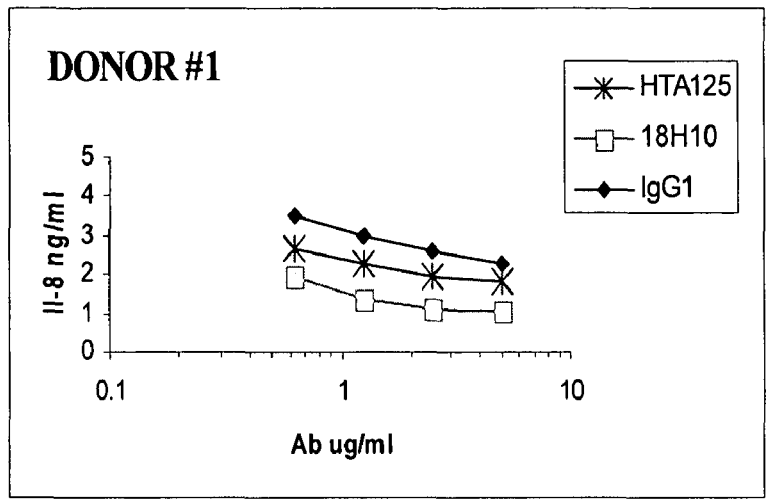
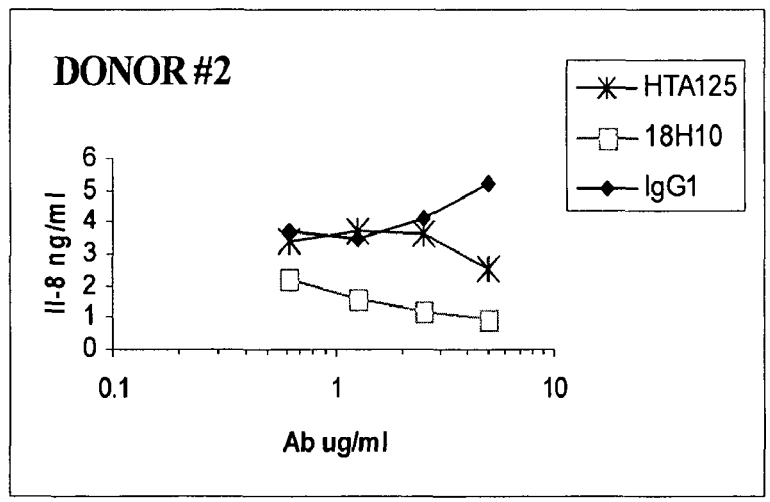
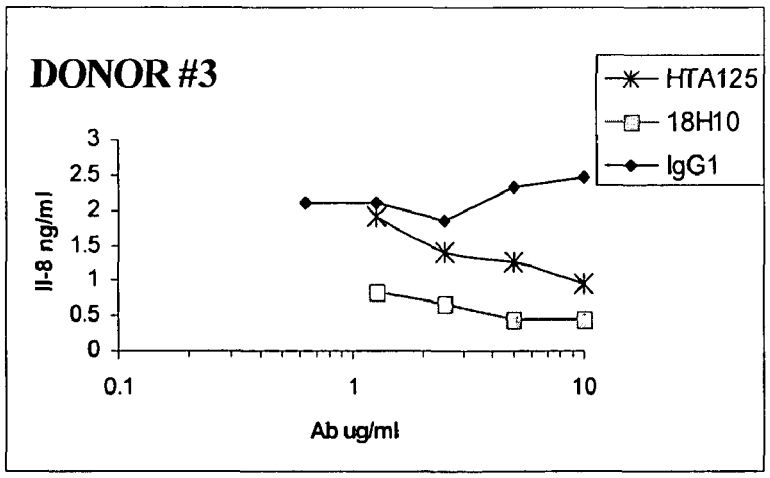

Figure 5B
Panel 1:
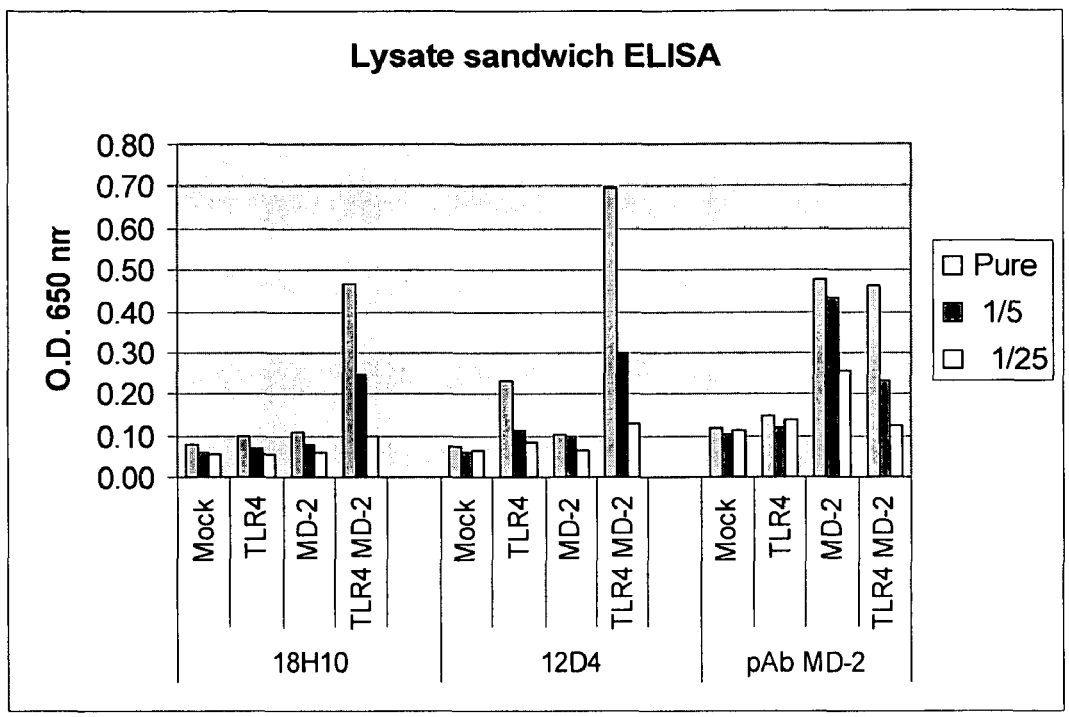
Panel 2:
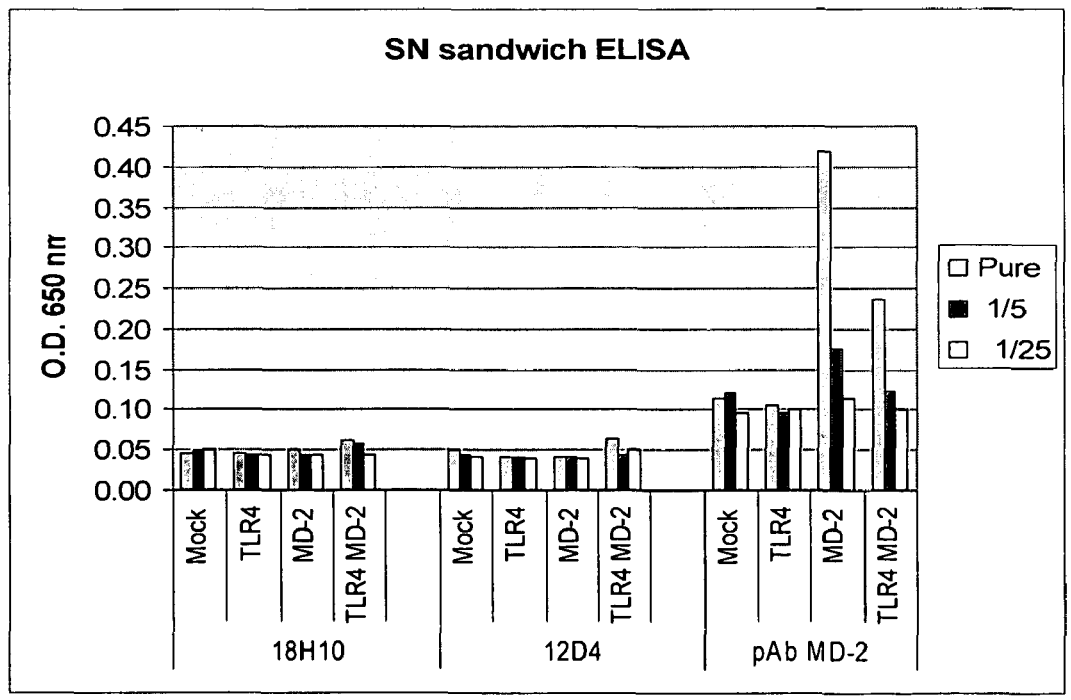

Figure 6A: 18H10 VH nucleotide sequence

```
  1 caggtgcaac tgcagcagtc tggggctgat cttgtgaggc caggggcctt
      q  v  q   l  q  q  s   g  a  d   l  v  r   p  g  a
 51 agtcaagttg tcctgcacag cttctggctt caacattaaa gactcctata
      l  v  k   l  s  c   t  a  s  g   f  n  i  k   d  s  y
101 tacactgggt gaagaagagg cctgaatggg gcctggagtg gattggatgg
      i  h  w   v  k  k   r  p  e  w   g  l  e  w   i  g  w
151 actgatcctg agaatgttaa ttctatatat gacccgaggt ttcagggcaa
      t  d  p   e  n  v   n  s  i  y   d  p  r   f  q  g
201 ggccagtata acagcagaca catcctccaa cacagccttc cttcagctca
      k  a  s  i   t  a  d   t  s  s   n  t  a  f   l  q  l
251 ccagcctgac atctgaggac actgccgtct attactgtgc tagggggttat
      t  s  l   t  s  e  d   t  a  v   y  y  c   a  r  g  y
301 aacggtgttt actatgctat ggactactgg ggccaaggga cctcagtcac
      n  g  v   y  y  a   m  d  y  w   g  q  g   t  s  v
351 cgtctcctca (SEQ ID NO:1)
      t  v  s  s (SEQ ID NO:2)
```

Figure 6B: 18H10 VH protein sequence

```
  1 qvqlqqsgad lvrpgalvkl sctasgfnik dsyihwvkkr pewglewigw
 51 tdpenvnsiy dprfqgkasi tadtssntaf lqltsltsed tavyycargy
101 ngvyyamdyw gqgttvtvss (SEQ ID NO:2)
```

Figure 6C: 18H10 VH CDR protein sequences dsyih (SEQ ID NO:3)
wtdpenvnsiydprfqg (SEQ ID NO:4)
gyngvyyamdy (SEQ ID NO:5)

Figure 6D: 18H10 VL nucleotide sequence

```
  1 caaattgttc tcacccagtc tccatcaatc atgtctgcgt ctctagggga
      q  i  v   l  t  q   s  p  s  i   m  s  a   s  l  g
 51 ggagatcacc ctaacctgca gtgccagctc gagtgtaatt tacatgcact
      e  e  i  t   l  t  c   s  a  s   s  v  i   y  m  h
101 ggtaccagca gaagtcaggc acttctccca aactcttgat ttataggaca
      w  y  q   q  k  s  g   t  s  p   k  l  l   i  y  r  t
151 tacaacctgg cttctggagt cccttctcgc ttcagtggca gtgggtctgg
      y  n  l   a  s  g   v  p  s   r  f  s  g   s  g  s
201 gacctttat tctctcacaa tcagcagtgt ggaggctgaa gatgctgccg
      g  t  f  y   s  l  t   i  s  s   v  e  a   e  d  a  a
251 attattactg ccatcagtgg agtagttttc cgtacacgtt cggaggggggg
      d  y  y   c  h  q  w   s  s  f   p  y  t   f  g  g  g
301 accaagctgg aaatcaaacg g (SEQ ID NO:6)
      t  k  l   e  i  k   r (SEQ ID NO:7)
```

Figure 6E: 18H10 VL protein sequence

```
  1 qviltqspsi msaslgeeit ltcsasssvi ymhwyqqksg tspklliyrt
 51 ynlasgvpsr fsgsgstfy sltissveae daadyychqw ssfpytfggg
101 tkleikr (SEQ ID NO:7)
```

Figure 6F: 18H10 VL CDR protein sequences sasssviymh (SEQ ID NO:8)
rtynlas (SEQ ID NO:9)
hqwssfpyt (SEQ ID NO:10)

16G7

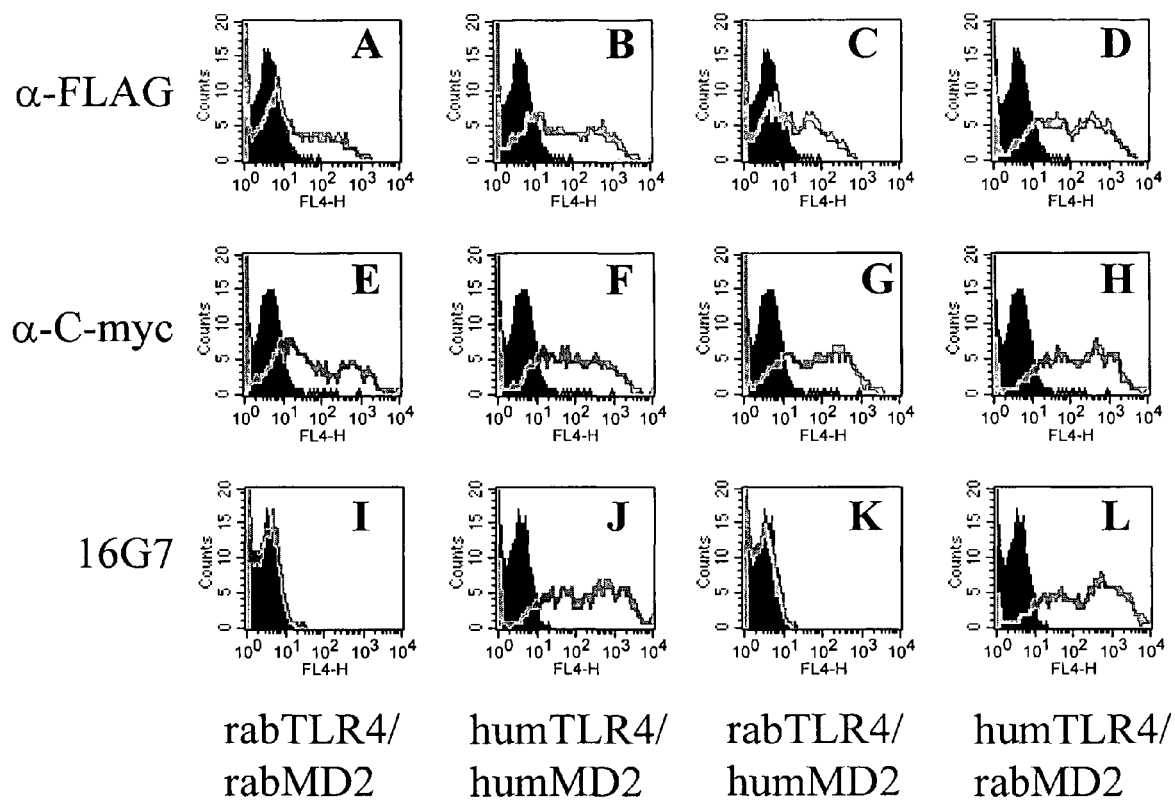

Figure 13A: 16G7 VH nucleotide sequence

```
1    aggtgaaact gcaggagtct ggagctgagc tgatgaagcc tggggcctca
        v  k  l   q  e  s    g  a  e    l  m  k     p  g  a  s
51   gtgaagatat cctgcaaggc tactggctac aaattcagtg actactggat
        v  k  i   s  c  k    a  t  g  y   k  f  s   d  y  w
101  agagtggata aaacagaggc ctggacatgg ccttgagtgg attggagaga
        i  e  w  i   k  q  r   p  g  h   g  l  e  w   i  g  e
151  ttttgcctgg aagtggtagt actaactaca atgaggactt caaggacaag
        i  l  p  g  s  g  s   t  n  y    n  e  d    f  k  d  k
201  gccacattca cttcagatac atcctccaac acagcctaca tgcaactcag
        a  t  f   t  s  d    t  s  s  n   t  a  y    m  q  l
251  cagcctgaca tctgaagact ctgccgtcta ttactgtgca aaagaggaga
        s  s  l  t   s  e  d    s  a  v   y  y  c  a   k  e  e
301  gggcgtacta ctttggctat ggggccaag ggaccacggt caccgtctcc
        r  a  y   y  f  g  y   w  g  q    g  t  t    v  t  v  s
351  tca (SEQ ID NO:11)
        s (SEQ ID NO:12)
```

Figure 13B: 16G7 VH protein sequence

```
1    qvqlqqsgaelmkpgasvkisckatgykfs*dywie*wikqrpghglewig*e*
51   *ilpgsgstnynedfkd*katftsdtssntaymqlssltsedsavyycak*ee*
101  *rayyfgy*wgqgttvtvss (SEQ ID NO:12)
```

Figure 13C: 16G7 VH CDR protein sequences dywie (SEQ ID NO:13)
eilpgsgstnynedfkd (SEQ ID NO:14)
eerayyfgy (SEQ ID NO:15)

Figure 13D: 16G7 VL nucleotide sequence

```
1    gatgttttga tgacccaaac tccactctcc ctgcctgtca gtcttggaga
        d  v  l  m   t  q    t  p  l  s    l  p  v   s  l  g
51   tcaagcctcc atctcttgca ggtctagtca gagccttgaa aacagtaatg
        d  q  a  s   i  s  c   r  s  s   q  s  l  e   n  s  n
101  gaaacaccta tttgaactgg tacctccaga aaccaggcca gtctccacag
        g  n  t   y  l  n  w   y  l  q    k  p  g    q  s  p  q
151  ctcctgatct acagggtttc caaccgattt tctggggtcc tagacaggtt
        l  l  i  y   r  v   s  n  r  f   s  g  v    l  d  r
201  cagtggtagt ggatcaggga cagatttcac actgaaaatc agcagagtgg
        f  s  g  s   g  s  g    t  d  f    t  l  k  i   s  r  v
251  aggctgagga tttgggagtt tatttctgcc tccaagttac acatgtccct
        e  a  e   d  l  g  v    y  f  c    l  q  v    t  h  v  p
301  cccacgttcg gtgctgggac caagctggaa ctgaaacgg (SEQ ID NO:16)
        p  t  f   g  a  g    t  k  l  e    l  k  r (SEQ ID NO:17)
```

Figure 13E: 16G7 VL protein sequence

```
1    dvvmtqtplslpvslgdqasisc*rssqslensngntyln*wylqkpgqspq
51   lliy*rvsnrfs*gvldrfsgsgsgtdftlkisrveaedlgvyfc*lqvthvp*
101  *pt*fgagtklelkr (SEQ ID NO:17)
```

Figure 13F: 16G7 VL CDR protein sequences rssqslensngntyln (SEQ ID NO:18)
rvsnrfs (SEQ ID NO:19)
lqvthvppt (SEQ ID NO:20)

15C1

Figure 16
Donor 1
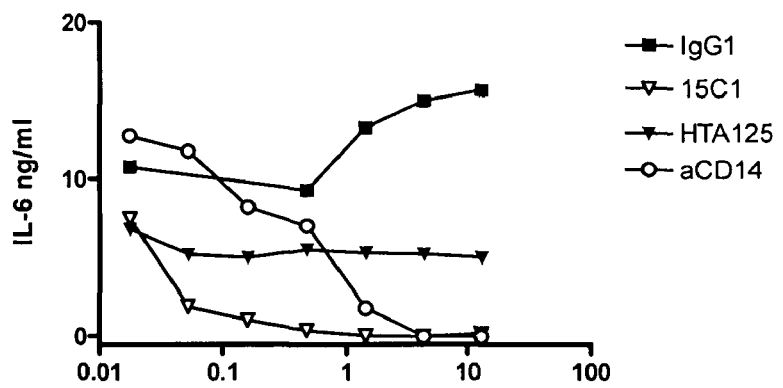
Donor 2
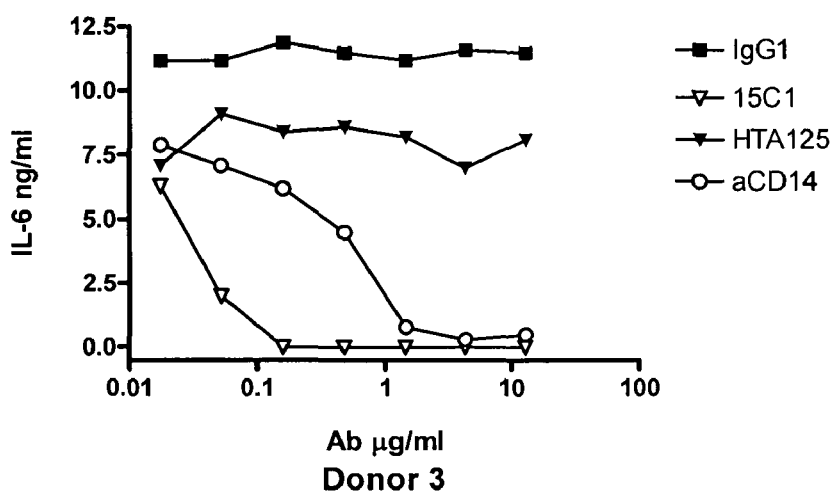
Donor 3
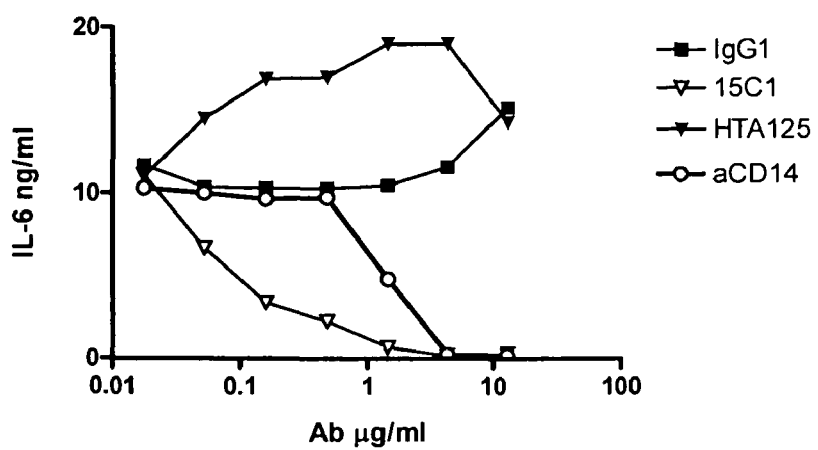

Figure 18A: 15C1 VH nucleotide sequence

```
1   gatgtgcagc ttcaggagtc aggacctgac ctaatacaac cttctcagtc actttcactc acctgcactg
     d  v  q   l  q  e   s  g  p  d  l  i  q   p  s  q    s  l  s  l   t  c  t
71  tcactggcta ctccatcacc ggtggttata gctggcactg gatccggcag tttccaggaa acaaactgga
     v  t  g  y  s  i  t   g  g  y   s  w  h  w  i  r  q   f  p  g  n  k  l
141 atggatgggc tacatccact acagtggtta cactgacttc aaccctctc  tcaaaactcg aatctctatc
     e  w  m  g  y  i  h   y  s  g   y  t  d  f  n  p  s  l  k  t   r  i  s  i
211 actcgagaca catccaagaa ccagttcttc ctgcagttga attctgtgac tactgaagac acagccacat
     t  r  d   t  s  k  n  q  f  f   l  q  l   n  s  v   t  t  e  d  t  a  t
281 attactgtgc aagaaaagat ccgtccgacg gatttcctta ctggggccaa gggactctgg tcactgtctc
     y  y  c   a  r  k  d   p  s  d   g  f  p   y  w  g  q  g  t  l  v  t  v
351 tgca (SEQ ID NO:21)
     s  a (SEQ ID NO:22)
```

Figure 18B: 15C1 VH protein sequence

```
1   dvqlqesgpd liqpsqslsl tctvtgysit ggyswhwirq fpgnklewmg
51  yihysgytdf npslktrisi trdtsknqff lqlnsvtted tatyycarkd
101 psdgfpywgq gtlvtvsa (SEQ ID NO:22)
```

Figure 18C: 15C1 VH CDR protein sequences

```
ggyswh (SEQ ID NO:23)
yihysgytdfnpslkt (SEQ ID NO:24)
kdpsdgfpy (SEQ ID NO:25)
```

Figure 18D: 15C1 VL nucleotide sequence

```
1   gacattgtga tgacccagtc tccagccacc ctgtctgtga ctccaggtga tagagtctct
     d  i  v  m  t  q   s  p  a  t   l  s  v   t  p  g   d  r  v  s
61  ctttcctgca gggccagcca gagtatcagc gaccacttac actggtatca acaaaaatca
     l  s  c   r  a  s  q  s  i  s   d  h  l   h  w  y   q  q  k  s
121 catgagtctc cacggcttct catcaaatat gcttcccatg ccatttctgg gatcccctcc
     h  e  s   p  r  l   l  i  k  y   a  s  h   a  i  s  g  i  p  s
181 aggttcagtg gcagtggatc agggacagat ttcactctca gcatcaaaag tgtggaacct
     r  f  s   g  s  g   s  g  t  d   f  t  l   s  i  k   s  v  e  p
241 gaagatattg gggtgtatta ctgtcaaaat ggtcacagtt ttccgctcac gttcggtgct
     e  d  i   g  v  y   y  c  q  n   g  h  s   f  p  l   t  f  g  a
301 gggaccaagc tggagctgaa a (SEQ ID NO:26)
     g  t  k   l  e  l   k (SEQ ID NO:27)
```

Figure 18E: 15C1 VL protein sequence

```
1   divmtqspat lsvtpgdrvs lscrasqsis dhlhwyqqks hesprlliky
51  ashaisgips rfsgsgsgtd ftlsiksvep edigvyycqn ghsfplttfga
101 gtklelkr (SEQ ID NO:27)
```

Figure 18F: 15C1 VL CDR protein sequences

```
rasqsisdhlh (SEQ ID NO:28)
yashais (SEQ ID NO:29)
qnghsfplt (SEQ ID NO:30)
```

7E3

Figure 23
Donor 1
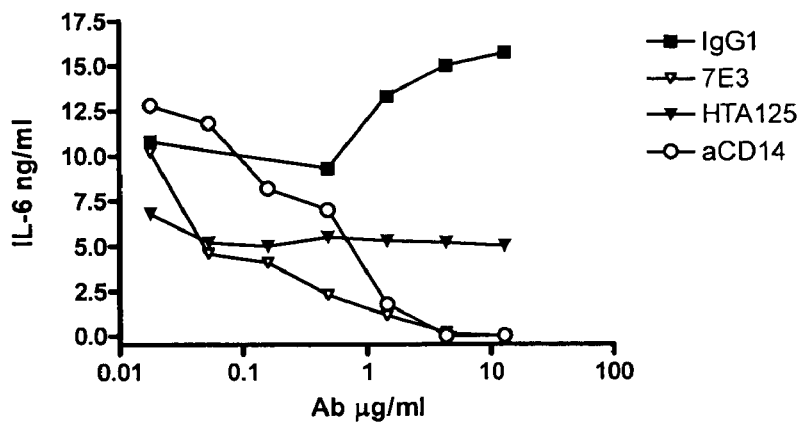
Donor 2
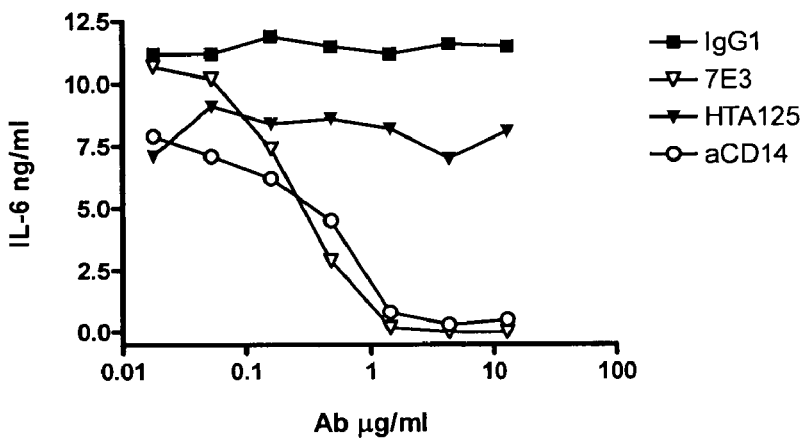
Donor 3
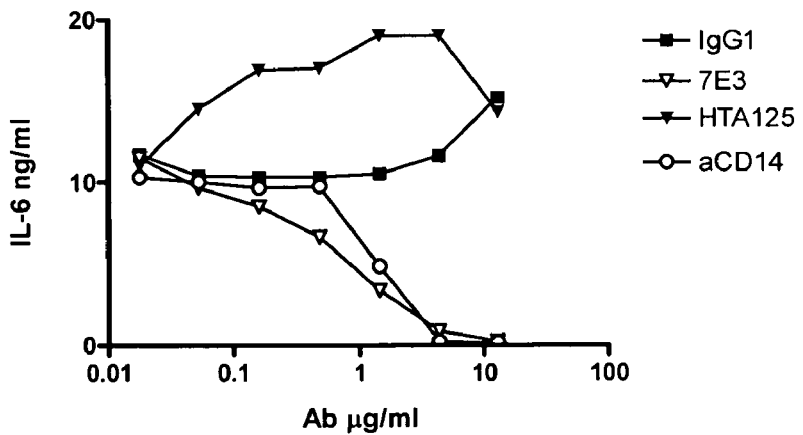

Figure 25A: 7E3 VH nucleotide sequence

```
1    caggttactc tgaaagagtc tggccctggg atattgcagc cctcccagac cctcagtctg acttgttctt
      q  v  t   l  k  e    s  g  p  g  i  l  q    p  s  q    t  l  s  l  t  c  s
71   tctctgggtt tcactgacc acttataata taggagtagg ctggattcgt cagccttcag ggaagggtct
      f  s  g   f  s  l  t  t  y  n  i  g  v    g  w  i  r    q  p  s  g  k  g
141  ggagtggctg gcacacattt ggtggaatga taatatttac tataatacag tccttaagag ccgactcaca
      l  e  w  l  a  h  i  w  w  n    d  n  i  y  y  n  t    v  l  k  s  r  l  t
211  ttctccaagg atacctccaa caaccaggtt ttcctcaaga tcgccagtgt ggacattgca gatactgcca
      f  s  k   d  t  s    n  n  q  v  f  l  k    i  a  s   v  d  i  a   d  t  a
281  catattactg tattcgaatg gctgagggaa ggtacgacgc tatggactac tggggtcaag gaacctcagt
      t  y  y   c  i  r  m    a  e  g    r  y  d  a  m  d  y  w  g  q   g  t  s
351  caccgtctcc tca (SEQ ID NO:31)
      v  t  v  s  s (SEQ ID NO:32)
```

Figure 25B: 7E3 VH protein sequence

```
1    qvtlkesgpg ilqpsqtlsl tcsfsgfslt tynigvgwir qpsgkglewl
51   ahiwwndniy yntvlksrlt fskdtsnnqv flkiasvdia dtatyycirm
101  aegrydamdy wgqgtsvtvs s (SEQ ID NO:32)
```

Figure 25C: 7E3 VH CDR protein sequences

```
tynigvg (SEQ ID NO:33)
hiwwndniyyntvlks (SEQ ID NO:34)
maegrydamdy (SEQ ID NO:35)
```

Figure 25D: 7E3 VL nucleotide sequence

```
1    gctatccaga tgacacagag tacatcctcc ctgtctgcct ctctgggaga cagagtcacc atcaattgca
      a  i  q   m  t  q    s  t  s  s  l  s  a    s  l  g    d  r  v  t   i  n  c
71   gggcaagtca ggacatcacc aattatttaa attggtatca gcagaaacca gatggaactg tcagactcct
      r  a  s   q  d  i  t   n  y  l    n  w  y  q  q  k  p   d  g  t   v  r  l
141  gatctattat acatcaaaat tacactcagg agccccatca aggttcagtg gccgtgggtc tggaacagat
      l  i  y  y   t  s  k   l  h  s    g  a  p  s   r  f  s   g  r  g   s  g  t  d
211  tattctctca ccattagtaa cctggagcaa gaggatattg ccacttactt ttgccaacag ggtaatacgt
      y  s  l   t  i  s   n  l  e  q    e  d  i  a   t  y  f  c  q  q    g  n  t
281  ttccgtggac gttcggtgga ggcaccaaac tggaaatcaa acgt (SEQ ID NO: 36)
      f  p  w   t  f  g  g   g  t  k   l  e  i   k  r (SEQ ID NO:37)
```

Figure 25E: 7E3 VL protein sequence

```
1    aiqmtqstss lsaslgdrvt incrasqdit nylnwyqqkp dgtvrlliyy
51   tsklhsgaps rfsgrgsgtd ysltisnleq ediatyfcqq gntfpwtfgg
101  gtkleikr (SEQ ID NO:37)
```

Figure 25F: 7E3 VL CDR protein sequences

```
rasqditnyln (SEQ ID NO:38)
ytsklhs (SEQ ID NO:39)
qqgntfpwt (SEQ ID NO:40)
```

♦ IgG1
▼ 7E3 chimeric

▲ 7E3
▼ 7E3 chimeric

Figure 32A

MD-1 nucleic acid sequence:

```
1    ggcacgagcg gcacgagccc accatgaagg gtttcacagc cactctcttc ctctggactc
61   tgattttcc  cagctgcagt ggaggcggcg gtgggaaagc ctggcccaca cacgtggtct
121  gtagcgacag cggcttggaa gtgctctacc agagttgcga tccattacaa gattttggct
181  tttctgttga aaagtgttcc aagcaattaa aatcaaatat caacattaga tttggaatta
241  ttctgagaga ggacatcaaa gagctttttc ttgacctagc tctcatgtct caaggctcat
301  ctgttttgaa tttctcctat cccatctgtg aggcggctct gcccaagttt tctttctgtg
361  gaagaaggaa aggagagcag atttactatg ctgggcctgt caataatcct gaatttacta
421  ttcctcaggg agaataccag gttttgctgg aactgtacac tgaaaaacgg tccaccgtgg
481  cctgtgccaa tgctactatc atgtgctcct gactgtggcc tgtagcaaaa atcacagcca
541  gctgcatctc gtgggacctc caagctcctc tgactgaacc tacgtgggag gagaagcagt
601  ctgatgacag agagaggctc tacaagaag  cgccccaaa  gagtgcagct gctaatttta
661  gtcccaggac cagacatccc cagactccac agatgtaatg aagtccccga atgtatctgt
721  ttctaaggag cctcttggca gtccttaagc agtcttgagg gtccatcctt tttctctaat
781  tggtcgcctc ccaccagact cacctgcttt tcaactttt  aggagtgctt cctcacagtt
841  accaagaata aagaaagctg gccacc (SEQ ID NO:41)
```

Figure 32B

MD-1 amino acid sequence:

```
1    mkgftatlfl wtlifpscsg ggggkawpth vvcsdsglev lyqscdplqd fgfsvekcsk
61   qlksninirf giilredike lfldlalmsq gssvlnfsyp iceaalpkfs fcgrrkgeqi
121  yyagpvnnpe ftipqgeyqv llelytekrs tvacanatim cs (SEQ ID NO:42)
```

Figure 33A

MD-2 nucleic acid sequence:
```
1    ggcgggccgc tcccacttcg gcacgagggg cacgaggtaa atcttttctg cttactgaaa
61   aggaagagtc tgatgattag ttactgatcc tctttgcatt tgtaaagctt tggagatatt
121  gaatcatgtt accatttctg ttttttttcca ccctgttttc ttccatattt actgaagctc
181  agaagcagta ttgggtctgc aactcatccg atgcaagtat ttcatacacc tactgtgata
241  aaatgcaata cccaatttca attaatgtta accctgtat agaattgaaa ggatccaaag
301  gattattgca cattttctac attccaagga gagatttaaa gcaattatat ttcaatctct
361  atataactgt caacaccatg aatcttccaa agcgcaaaga agttatttgc cgaggatctg
421  atgacgatta ctcttttgc agagctctga agggagagac tgtgaataca acaatatcat
481  tctccttcaa gggaataaaa ttttctaagg gaaaatacaa atgtgttgtt gaagctattt
541  ctgggagccc agaagaaatg ctcttttgct tggagtttgt catcctacac caacctaatt
601  caaattagaa taaattgagt attt (SEQ ID NO:43)
```

Figure 33B

MD-2 amino acid sequence:
```
1    MLPFLFFSTL FSSIFTEAQK QYWVCNSSDA SISYTYCDKM QYPISINVNP CIELKGSKGL
61   LHIFYIPRRD LKQLYFNLYI TVNTMNLPKR KEVICRGSDD DYSFCRALKG ETVNTTISFS
121  FKGIKFSKGK YKCVVEAISG SPEEMLFCLE FVILHQPNSN (SEQ ID NO:44)
```

NEUTRALIZING ANTIBODIES AND METHODS OF USE THEREOF

RELATED APPLICATIONS

This application is a divisional of U.S. application Ser. No. 11/009,939, filed Dec. 10, 2004, issued as U.S. Pat. No. 7,312,320, which claims the benefit of U.S. Provisional Application No. 60/528,812, filed Dec. 10, 2003; of U.S. Provisional Application No. 60/528,811, filed Dec. 10, 2003; and of U.S. Provisional Application No. 60/528,962, filed Dec. 10, 2003; each of which is incorporated herein by reference in its entirety.

FIELD OF THE INVENTION

This invention relates generally to the generation of neutralizing monoclonal antibodies, and in particular, to monoclonal antibodies that recognize the Toll-like Receptor 4/MD-2 receptor complex, to monoclonal antibodies that recognize both the Toll-like Receptor 4/MD-2 receptor complex and Toll-like Receptor 4 when not complexed with MD-2, and to methods of using the monoclonal antibodies as therapeutics. This invention also relates to soluble chimeric proteins, methods of expressing and purifying soluble chimeric proteins, and methods of using soluble chimeric proteins as therapeutics, in screening assays and in the production of antibodies.

BACKGROUND OF THE INVENTION

Toll receptors, first discovered in *Drosophila*, are type I transmembrane protein having leucine-rich repeats (LRRs) in the extracellular portion of the protein, and one or two cysteine-rich domains. The mammalian homologs of the *Drosophila* Toll receptors are known as "Toll-like receptors" (TLRs). TLRs play a role in innate immunity by recognizing microbial particles and activating immune cells against the source of these microbial particles.

Currently, ten types of Toll-like receptors have been identified in humans, TLRs 1-10. These TLRs are characterized by the homology of their intracellular domains to that of the IL-1 receptor, and by the presence of extracellular leucine-rich repeats. The different types of TLRs are activated by different types of microbial particles. For example, TLR4 is primarily activated by lipopolysaccharide (LPS), while TLR2 is activated by lipoteichoic (LTA), lipoarabinomannan (LAM); lipoprotein (BLP), and peptideglycans (PGN). Toll receptor homologs, such as RP105, have also been identified.

Myeloid differentiation protein-2 (MD-2), a TLR4 accessory protein, has been identified and characterized. This protein has been found to interact directly with TLR4, and MD-2 has the ability to enable post-translational modifications of TLR4, as well as facilitate its transport to the cell surface. TLR4 and MD-2 form a complex on the cell surface.

Lipopolysaccharide (LPS), a component of gram-negative bacteria, is a microbial particle capable of strongly activating the innate immune system. LPS delivers signals to immune cells via its multi-chain receptor, comprising the TLR4/MD-2 complex as the principle signaling component.

Accordingly, there exists a need for methods and compositions that modulate signaling that is mediated by the TLR4/MD-2 complex.

SUMMARY OF THE INVENTION

The invention provides monoclonal antibodies recognizing the TLR4/MD-2 receptor expressed on the cell surface. The antibodies are capable of blocking LPS-induced IL-8 production. In some cases, the monoclonal antibodies of the invention also recognize TLR4 when not complexed with MD-2 (e.g., soluble TLR4 proteins, TLR4 expressed on the cell surface). Exemplary monoclonal antibodies include 18H10, 16G7, 15C1 and 7E3.

The antibodies of the invention contain a heavy chain variable region having the amino acid sequence of SEQ ID NOS: 2, 12, 22 or 32 and a light chain variable region having the amino acid sequence of SEQ ID NOS: 7, 17, 27 or 37. Preferably, the three heavy chain CDRs include an amino acid sequence at least 90%, 92%, 95%, 97% 98%, 99% or more identical a sequence selected from the group consisting of DSYIH (SEQ ID NO:3); WTDPENVNSIYDPRFQG (SEQ ID NO:4), GYNGVYYAMDY (SEQ ID NO:5); DYWIE (SEQ ID NO:13); EILPGSGSTNYNEDFKD (SEQ ID NO:14); EERAYYFGY (SEQ ID NO:15); GGYSWH (SEQ ID NO:23); YIHYSGYTDFNPSLKT (SEQ ID NO:24); KDPSDGFPY (SEQ ID NO:25); TYNIGVG (SEQ ID NO:33); HIWWNDNIYYNTVLKS (SEQ ID NO:34); and MAEGRYDAMDY (SEQ ID NO:35) and a light chain with three CDR that include an amino acid sequence at least 90%, 92%, 95%, 97% 98%, 99% or more identical to a sequence selected from the group consisting of the amino acid sequence of SASSSVIYMH (SEQ ID NO:8); RTYNLAS (SEQ ID NO:9); HQWSSFPYT (SEQ ID NO:10); RSSQSLENSNGNTYLN (SEQ ID NO:18); RVSNRFS (SEQ ID NO:19); LQVTHVPPT (SEQ ID NO:20); RASQSISDHLH (SEQ ID NO:28); YASHAIS (SEQ ID NO:29); QNGHSFPLT (SEQ ID NO:30); RASQDITNYLN (SEQ ID NO:38); YTSKLHS (SEQ ID NO:39); and QQGNTFPWT (SEQ ID NO:40). The antibody binds to the TLR4/MD-2 complex, to TLR4 when not complexed with MD-2, or to both.

The present invention also provides methods of treating or preventing pathologies associated with aberrant TLR4/MD-2 activation and/or aberrant LPS activity (e.g., aberrant IL-8 production), or alleviating a symptom associated with such pathologies, by administering a monoclonal antibody of the invention to a subject in which such treatment or prevention is desired. The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to reduce LPS-induced production of IL-8. As used herein, the term "reduced" refers to a decreased production of IL-8 in the presence of a monoclonal antibody of the invention, wherein the production is, for example, local IL-8 production (e.g., at a site of inflamed tissue) or systemic IL-8 production. LPS-induced production of IL-8 is decreased when the level of IL-8 production in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of IL-8 production (i.e., the level of IL-8 production in the absence of the monoclonal antibody). Level of IL-8 production is measured, e.g., using the human whole blood or huTLR4/MD2 transfected HEK293 cellular assays described herein. Those skilled in the art will appreciate that the level of IL-8 production can be measured using a variety of assays, including, for example, commercially available ELISA kits.

Pathologies treated and/or prevented using the monoclonal antibodies of the invention include, for example, sepsis induced by microbial products, acute inflammation, chronic inflammation (e.g., chronic inflammation associated with allergic conditions and asthma), autoimmune diseases (e.g., IBD and atherosclerosis) and diseases in which mechanical stress induces the expression of endogenous soluble stress factors (e.g., Hsp60, fibronectin, heparan sulphate, hyaluronan, gp96, β-Defensin-2 and surfactant protein A). Pathologies in which mechanical stress induces the expression of endogenous soluble stress factors include, for example, osteoarthritis and rheumatoid arthritis. Pathologies associated with mechanical stress can also occur in subjects and patients placed on respirators, ventilators and other respiratory-assist devices. Such pathologies include, for example, ventilator-induced lung injury ("VILI"), also referred to as ventilation-associated lung injury ("VALI").

Pharmaceutical compositions according to the invention can include an antibody of the invention and a carrier. These pharmaceutical compositions can be included in kits, such as, for example, diagnostic kits.

The present invention also provides soluble chimeric toll receptor proteins (also referred to herein as toll-like receptor proteins), methods for expressing toll receptor proteins, and methods for purifying such proteins in a soluble form.

The present invention provides chimeric polypeptides in which a toll-like receptor polypeptide, or a biologically active derivative thereof, is operably linked to an MD accessory polypeptide, or a biologically active derivative thereof. The toll-like receptor polypeptide is a polypeptide selected from the group consisting of TLRs 1-10 and RP105.

The MD accessory polypeptide is, for example, MD-1 or MD-2. The toll-like receptor polypeptide is, in some instances, operably linked to the MD accessory polypeptide using a flexible glycine-serine linker, which renders the toll receptor both stable during expression and soluble during purification. For example, a chimeric polypeptide of the invention includes the extracellular portion of a toll receptor fused at its C terminus to the N terminus of a mature MD protein (i.e., MD-1 or MD-2) via a flexible glycine/serine linker.

The present invention also provides methods for producing soluble chimeric fusion proteins by coupling a toll-like receptor polypeptide, or a biologically active derivative thereof, to an MD accessory polypeptide, or a biologically active derivative thereof. The present invention also provides methods for producing soluble chimeric fusion proteins by constructing a vector that includes a nucleic acid sequence encoding a toll-like receptor polypeptide (or a biologically active derivative thereof) coupled to a nucleic acid sequence encoding an MD accessory polypeptide (or a biologically active derivative thereof); transfecting a cell with this vector; culturing the cell under conditions that permit production of a fusion protein having a toll-like receptor polypeptide coupled to an MD accessory polypeptide; and isolating that fusion protein. The MD accessory polypeptide is, for example, MD-1 or MD-2, and the toll-like receptor polypeptide can be a polypeptide selected from the group consisting of TLRs 1-10 and RP105. The toll-like receptor polypeptide is operably linked to the MD accessory polypeptide by a flexible glycine-serine linker, which renders the toll receptor both stable during expression and soluble during purification.

The present invention also provides methods of treating or preventing pathologies associated with aberrant toll-like receptor function, or alleviating a symptom associated with these pathologies, by administering a soluble chimeric polypeptide of the invention to a subject in which such treatment or prevention or alleviation is desired in an amount sufficient to treat or prevent or alleviate the pathology, or a symptom thereof, in the subject. The subject to be treated is, e.g., human. The amount of soluble chimeric polypeptide sufficient to treat or prevent the pathology in the subject is an amount that is sufficient to modulate (e.g., reduce or prevent) the activation of a toll-like receptor in the subject to be treated. Activation of a toll-receptor is reduced or decreased when the level of toll-receptor activation in the presence of a chimeric protein of the invention is greater than or equal to 5%, 10%, 20%, 25%, 30%, 40%, 50%, 60%, 70%, 75%, 80%, 90%, 95%, 99%, or 100% lower than a control level of toll-like receptor activation (i.e., the level of activation the absence of the chimeric protein). The level of toll-receptor activation is measured using any of a variety of techniques known in the art. For example, the level of TLR4 activation can be measured by detecting the level of LPS-induced IL-8 production. Those skilled in the art will appreciate that the level of toll-receptor activation can also be measured, for example, by detecting activation, if any, of NF-kappa B or JNK (c-jun terminal kinase), which initiate the transcription of genes encoding pro-inflammatory cytokines (e.g., IL1-alpha, IL1-beta, IL6, and TNF-alpha). Activation of JNK and/or NF-kappa B can be detected by measuring the levels of one or more pro-inflammatory cytokines.

In some embodiments, the pathology to be treated is sepsis, acute inflammation, chronic inflammation or an autoimmune disease. For example, the pathology is any one of a variety of types of arthritis.

The present invention also includes antibodies that immunospecifically bind to the soluble chimeric polypeptides of the invention, such as, for example, monoclonal antibodies or humanized antibodies.

Pharmaceutical compositions according to the invention can include a soluble chimeric polypeptide of the invention and a carrier, and/or an antibody of the invention and a carrier. These pharmaceutical compositions can be included in kits, such as, for example, diagnostic kits.

The invention also provides methods of screening for a ligand that binds a toll-like receptor and modulates toll-like receptor activity. According to these methods of the invention, these ligands are identified by providing a chimeric polypeptide of the invention that has a property or function that is ascribable to that polypeptide; contacting the chimeric polypeptide with a candidate compound; and determining whether the candidate compound alters the property or function ascribable to the polypeptide, wherein an alteration in the property or function ascribable to the polypeptide in the presence of the candidate compound indicates that the candidate compound is a ligand that modulates toll-like receptor activity.

One skilled in the art will appreciate that the chimeric polypeptides and antibodies of the invention have a variety of uses. For example, the chimeric proteins of the invention are used as therapeutic agents to prevent the activation of TLRs in disorders such as, for example, sepsis, acute inflammation, chronic inflammation, autoimmune diseases and various forms of arthritis. The chimeric proteins of the invention are also used as immunogens in more efficient methods of generating binding and blocking anti-TLR antibodies, and/or these chimeric polypeptides can be used as reagents in assays that screen for small molecular weight binders and blockers of TLRs activity. The chimeric proteins and/or antibodies of the invention are also used as reagents in diagnostic kits or as diagnostic tools, or these chimeric proteins and/or antibodies can be used in competition assays to generate therapeutic reagents.

BRIEF DESCRIPTION OF THE DRAWINGS

FIG. 3 is a series of graphs depicting inhibition of LPS-induced IL-8 production in human whole blood by the monoclonal antibody 18H10. Whole blood was drawn from 3 healthy volunteers, treated with heparin and diluted 1:4 in RPMI medium. The following antibodies were added at the concentrations indicated: control monoclonal antibody; HTA125 and 18H10. LPS was subsequently added for a final concentration of 10 ng/ml, and IL-8 levels were measured 6 hours post LPS treatment.

FIG. 5B is a graph demonstrating that MD-2 must be associated with TLR4 for the 18H10 antibody to recognize it. Lysates (Panel 1, i.e., upper panel) or supernatants (Panel 2, i.e., lower panel) from HEK 293 cells, transiently transfected as indicated, were incubated in wells coated with anti-FLAG M2. Binding of a biotinylated form of 18H10 was detected using streptavidin-HRP. Biotinylated 12D4 (an anti-TLR4 MAb) with streptavidin-HRP or a polyclonal rabbit Ab raised against soluble MD-2 with an anti rabbit IgG-HRP controlled the presence of TLR4 and MD-2 respectively. In this experiment, TLR4 had a FLAG tag at the N-terminus and was expressed using the vector pCNDA3.1 (–)hygro (Invitrogen). MD-2 had FLAG and 6× Histidine tags at the C terminus and was expressed using the vector pcDNA3 (Invitrogen). Mock cells were transfected with empty plasmid.

FIGS. 6A-6F are a series of illustrations depicting the VH nucleotide sequence (SEQ ID NO:1) (FIG. 6A), the VH amino acid sequence (SEQ ID NO:2) (FIG. 6B), the VL nucleotide sequence (SEQ ID NO:6) (FIG. 6D), and the VL amino acid sequence (SEQ ID NO:7) for 18H10 (FIG. 6E). The VH complementarity determining regions (CDRs) (SEQ ID NOs:3, 4 and 5) (FIG. 6C) and the VL CDRs (SEQ ID NOs: 8, 9 and 10) (FIG. 6F) are highlighted in the underlined, italic text in FIGS. 6B and 6E.

FIG. 12 is a series of graphs depicting the specificity of the 16G7 monoclonal antibody for TLR4. The specificity of the 16G7 antibody is shown by flow cytometry analysis of HEK 293 cells transiently transfected with either rabbit TLR4 and rabbit MD-2 (Panels A, E and I); human TLR4 and human MD-2 (Panels B, F and J); rabbit TLR4 and human MD-2 (Panels C, G and K); or human TLR4 and rabbit MD-2 (Panels D, H and L). Cells were incubated with either α-FLAG™ antibody (to detect TLR4 expression); α-C-myc antibody (to detect MD-2 expression) or the 16G7 monoclonal antibody, followed by an APC-coupled α-mouse (H+L) antibody.

FIGS. 13A-13F are a series of illustrations depicting the VH nucleotide sequence (SEQ ID NO:11) (FIG. 13A), the VH amino acid sequence (SEQ ID NO:12) (FIG. 13B), the VL nucleotide sequence (SEQ ID NO:16) (FIG. 13D), and the VL amino acid sequence (SEQ ID NO:17) (FIG. 13E) for 16G7. The VH complementarity determining regions (CDRs) (SEQ ID NOs: 13, 14 and 15) (FIG. 13C) and the VL CDRs (SEQ ID NOs: 18, 19 and 20) (FIG. 13F) are highlighted in the underlined, italic text in FIGS. 13B and 13E.

FIG. 16 is a series of graphs depicting inhibition of LPS-induced IL-8 production in human whole blood by the monoclonal antibody 15C1. Whole blood was drawn from 3 healthy volunteers, treated with heparin and diluted 1:4 in RPMI medium. The following antibodies were added at the concentrations indicated: Isotype matched control (IgG1); HTA125 (anti-human TLR4 non-blocking monoclonal antibody); 15C1 and 28C5 (anti-human CD14 blocking monoclonal antibody). LPS was subsequently added for a final concentration of 10 ng/ml.

FIGS. 18A-18F are a series of illustrations depicting the VH nucleotide sequence (SEQ ID NO:21) (FIG. 18A), the VH amino acid sequence (SEQ ID NO:22) (FIG. 18B), the VL nucleotide sequence (SEQ ID NO:26) (FIG. 18D), and the VL amino acid sequence (SEQ ID NO:27) (FIG. 18E) for 15C1. The VH complementarity determining regions (CDRs) (SEQ ID NOs: 23, 24 and 25) (FIG. 18C) and the VL CDRs (SEQ ID NOs: 28, 29 and 30) (FIG. 18F) are highlighted in the underlined, italic text in FIGS. 18B and 18E.

FIG. 23 is a series of graphs depicting inhibition of LPS-induced IL-8 production in human whole blood by the monoclonal antibody 7E3. Whole blood was drawn from 3 healthy volunteers, treated with heparin and diluted 1:4 in RPMI medium. The following antibodies were added at the concentrations indicated: Isotype matched control (IgG1); HTA125 (anti-human TLR4 non-blocking monoclonal antibody); 7E3 and 28C5 (anti-human CD14 blocking monoclonal antibody). LPS was subsequently added for a final concentration of 10 ng/ml.

FIGS. 25A-25F are a series of illustrations depicting the VH nucleotide sequence (SEQ ID NO:31) (FIG. 25A), the VH amino acid sequence (SEQ ID NO:32) (FIG. 25B), the VL nucleotide sequence (SEQ ID NO:36) (FIG. 25D), and the VL amino acid sequence (SEQ ID NO:37) (FIG. 25E) for 7E3. The VH complementarity determining regions (CDRs) (SEQ ID NOs: 33, 34 and 35) (FIG. 25C) and the VL CDRs (SEQ ID NOs: 38, 39 and 40) (FIG. 25F) are highlighted in the underlined italic text in FIGS. 25B and 25E.

FIG. 32A illustrates a nucleic acid sequence encoding the accessory protein MD-1 (SEQ ID NO:41).

FIG. 32B depicts an amino acid sequence of a mature MD-1 accessory protein in a preferred embodiment of the invention (SEQ ID NO:42).

FIG. 33A illustrates a nucleic acid sequence encoding the accessory protein MD-2 (SEQ ID NO:43).

FIG. 33B depicts an amino acid sequence of a mature MD-2 accessory protein (SEQ ID NO:44).

DETAILED DESCRIPTION OF THE INVENTION

Figure 1:
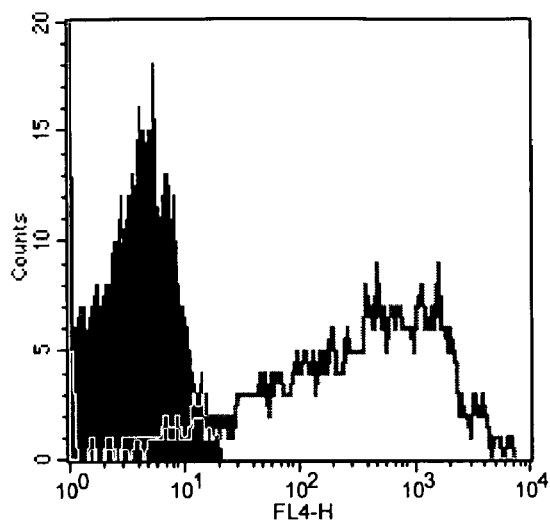
FIG. 1 is a graph depicting the binding of one monoclonal antibody of the invention, 18H10, to the TLR4/MD-2 complex. Specificity of binding is shown by flow cytometry using mock transfected or TLR4/MD-2 transfected cells. The results using mock-transfected cells are shown in the filled graph (left), while the results using TLR4/MD-2 transfected cells are shown as in the outline graph (right).

The present invention provides monoclonal antibodies that neutralize the activation of the TLR4/MD-2 receptor complex. In particular, the invention provides monoclonal antibodies that recognize the TLR4/MD-2 receptor complex expressed on the cell surface. These monoclonal antibodies block LPS-induced IL-8 production. In addition, some monoclonal antibodies of the invention also recognize TLR4 when not complexed with MD-2. Exemplary antibodies of the invention include, for example, the 18H10 antibody (FIGS. 6A-6F), the 16G7 antibody (FIGS. 13A-13F), the 15C1 antibody (FIGS. 18A-18F) and the 7E3 antibody (FIGS. 25A-25F).

The present invention also provides soluble chimeric toll receptor proteins (also referred to herein as toll-like receptor proteins), methods for expressing toll receptor proteins, and methods for purifying such proteins in a soluble form. The chimeric proteins are useful, e.g., in generating antibodies.

TLRs recognize microbial particles and activate immune cells against the source of these microbial particles. (See Takeda et al., Annu. Rev. Immunol., 21: 335-76 (2003), hereby incorporated by reference in its entirety). TLR4 and MD-2 have been shown to form a complex on the cell surface, and the presence of MD-2 appears essential for the responsiveness of TLR4 to various ligands, including LPS. LPS is a gram-negative bacterial outer membrane glycolipid that is capable of strongly activating the innate immune system. LPS has been implicated as one of the major factors activating the immune system during the severe generalized inflammation resulting from gram-negative infection. (Lakhani et al., Curr. Opin. Pediatr. 15: 278-282 (2003), hereby incorporated by reference in its entirety).

LPS delivers signals to immune cells via its multi-chain receptor in which the TLR4/MD-2 complex is the principle signaling component. LPS has been shown to exert its effects on the immune system via signaling through TLR4. LPS rapidly binds to the lipopolysaccharide-binding protein (LBP) in the bloodstream, and in this form, LPS interacts with the GPI-anchored cell surface protein CD14. LPS is then transferred to TLR4, which transduces an intracellular activation signal. Another protein, MD-2, has been found to be necessary for signal transduction via TLR4 to occur. MD-2 interacts directly with TLR4 and plays an important role in its post-translational modification and intracellular trafficking. In addition, MD-2 has been shown to directly bind LPS, which demonstrates the importance of this accessory protein in the LPS receptor complex. (See Miyake K., Int. Immunopharmacol. 3:119-128 (2003), hereby incorporated by reference in its entirety).

Accordingly, neutralization of LPS signaling mediated by the TLR4/MD-2 complex is a potential therapeutic strategy in the treatment of disorders such as, for example, acute systemic inflammation and sepsis induced by gram-negative bacterial infection.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is $\leq 1$ µM; preferably $\leq 100$ nM and most preferably $\leq 10$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to the Toll-like Receptor 4 (TLR4)/MD-2 complex or to TLR4 when not complexed to MD-2, when the equilibrium binding constant ($K_d$) is $\leq 1$ µM, preferably $\leq 100$ nM, more preferably $\leq 10$ nM, and most preferably $\leq 100$ µM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Preferred polypeptides in accordance with the invention comprise the human heavy chain immunoglobulin molecules represented in FIGS. 6B, 13B, 18B and 25B and the human light chain immunoglobulin molecules represented in FIGS. 6E, 13E, 18 and 25, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to TLR4/MD2 complex or TLR4 alone, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH=CH-$ (cis and trans), $-COCH_2-$, $CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Monoclonal antibodies of the invention have the ability to inhibit LPS-induced IL-8 production. Inhibition is determined, for example, in the human whole blood and huTLR4/MD2 transfected HEK 293 cellular assays described herein. Exemplary monoclonal antibodies include, for example, the antibodies referred to herein as "18H10", "16G7", "15C1" and "7E3". The 18H10 antibody recognizes the TLR4/MD-2 complex, but does not recognize an MD-2 protein when not complexed with TLR4. The 16G7, 15C1 and 7E3 monoclonal antibodies recognize the TLR4/MD-2 complex. 15C1 and 16G7 also recognize TLR4 when not complexed with MD-2.

Also included in the invention are antibodies that bind to the same epitope as the antibodies described herein. Those skilled in the art will recognize that it is possible to determine, without undue experimentation, if a monoclonal antibody has the same specificity as a monoclonal antibody of the invention (e.g., monoclonal antibody 18H10, 16G7, 15C1 and/or 7E3) by ascertaining whether the former prevents the latter from binding to the TLR4/MD-2 complex or to TLR4 when not complexed to MD-2. If the monoclonal antibody being tested competes with the monoclonal antibody of the invention, as shown by a decrease in binding by the monoclonal antibody of the invention, then it is likely that the two monoclonal antibodies bind to the same, or a closely related, epitope. Another way to determine whether a monoclonal antibody has the specificity of a monoclonal antibody of the invention is to pre-incubate the monoclonal antibody of the invention with the TLR4/MD-2 complex or a soluble TLR4 protein (with which it is normally reactive), and then add the monoclonal antibody being tested to determine if the monoclonal antibody being tested is inhibited in its ability to bind the TLR4/MD-2 complex or to bind TLR4 and TLR4 complexed with MD-2. If the monoclonal antibody being tested is inhibited then, in all likelihood, it has the same, or functionally equivalent, epitopic specificity as the monoclonal antibody of the invention. Screening of monoclonal antibodies of the invention, can be also carried out by measuring LPS-induced IL-8 production and determining whether the test monoclonal antibody is able to neutralize LPS-induced IL-8 production.

Various procedures known within the art may be used for the production of polyclonal or monoclonal antibodies directed against the TLR4/MD-2 complex, or to TLR4 when not complexed to MD-2, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The antibodies of the invention (e.g., 18H10, 16G7, 15C1 and 7E3) are monoclonal antibodies. Monoclonal antibodies that neutralize LPS-signaling that is mediated by the TLR4/MD-2 complex are generated, e.g., by immunizing BALB/c mice with combinations of cell transfectants expressing high levels of TLR4 and MD-2 on their surface and a recombinant soluble chimeric protein comprising both TLR4 and MD-2 tethered by a flexible linker sequence. Hybridomas resulting from myeloma/B cell fusions are then screened for reactivity to this TLR4/MD-2 complex.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816, 567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of the TLR4/MD-2 complex and/or TLR4 in a sample. The antibody can also be used to try to bind to and disrupt TLR4/MD-2 complex-related signaling.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments. The invention also includes $F_v$, $F_{ab}$, $F_{ab'}$ and $F_{(ab')2}$ anti-TLR4/MD2 complex fragments or anti-TLR4 fragments, single chain anti-TLR4/MD2 or anti-TLR4 antibodies, bispecific anti-TLR4/MD2 or anti-TLR4 antibodies and heteroconjugate anti-TLR4/MD2 or anti-TLR4 antibodies.

Bispecific antibodies are antibodies that have binding specificities for at least two different antigens. In the present case, one of the binding specificities is for the TLR4/MD2 complex and/or TLR4 when not complexed with MD-2. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant LPS signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, saponaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Preferred linkers are described in the literature. (See, for example, Ramakrishnan, S. et al., Cancer Res. 44:201-208 (1984) describing use of NBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against the TLR4/MD2 Complex and Antibodies Against TLR4

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a monoclonal antibody of the invention, are used to treat or alleviate a symptom associated with an immune-related disorder. The present invention also provides methods of treating or alleviating a symptom associated with an immune-related disorder. A therapeutic regimen is carried out by identifying a subject, e.g., a human patient suffering from (or at risk of developing) an immune-related disorder, using standard methods.

Antibodies of the invention, which are capable of inhibiting LPS-induced IL-8 production, are useful therapeutic tools in the treatment of disorders, such as, for example, acute inflammation and sepsis induced by microbial products (e.g., LPS) and exacerbations arising from this acute inflammation, such as, for example, chronic obstructive pulmonary disease and asthma (see O'Neill, Curr. Opin. Pharmacol. 3: 396-403 (2003), hereby incorporated by reference in its entirety). Such antibodies are also useful in treating neurodegenerative autoimmune diseases. (Lehnardt et al., Proc. Natl. Acad. Sci. USA 100: 8514-8519 (2003), hereby incorporated by reference in its entirety).

In addition, the antibodies of the invention are also useful as therapeutic reagents in the treatment of diseases, such as, for example, osteoarthritis, which are caused by mechanical stress, which, in turn, induces endogenous soluble "stress" factors that trigger TLR4. Endogenous soluble stress factor include e.g., Hsp60 (see Ohashi et al., J. Immunol. 164: 558-561 (2000)) and fibronectin (see Okamura et al., J. Biol. Chem. 276: 10229-10233 (2001) and heparan sulphate, hyaluronan, gp96, β-Defensin-2 or surfactant protein A (see e.g., Johnson et al., Crit. Rev. Immunol., 23(1-2):15-44 (2003), each of which is hereby incorporated by reference in its entirety). The antibodies of the invention are also useful in the treatment of a variety of disorders associated with mechanical stress, such as for example, mechanical stress that is associated with subjects and patients placed on respirators, ventilators and other respiratory-assist devices. For example, the antibodies of the invention are useful in the treatment of ventilator-induced lung injury ("VILI"), also referred to as ventilation-associated lung injury ("VALI").

Other disease areas in which inhibiting TLR4 function could be beneficial include, for example, chronic inflammation (e.g., chronic inflammation associated with allergic conditions and asthma), autoimmune diseases (e.g., inflammatory bowel disorder) and atherosclerosis (see O'Neill, Curr. Opin. Pharmacol. 3: 396-403 (2003), hereby incorporated by reference in its entirety).

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against the TLR4/MD-2 complex or to TLR4 when not complexed to MD-2 (or a fragment thereof) may be used in methods known within the art relating to the localization and/or quantitation of the TLR4/MD-2 complex or TLR4 (e.g., for use in measuring levels of the TLR4/MD-2 complex or TLR4 within appropriate physiological samples, for use in diagnostic methods, for use in imaging the protein, and the like). In a given embodiment, antibodies specific to the TLR4/MD-2 complex, or TLR4, or derivative, fragment, analog or homolog thereof, that contain the antibody derived antigen binding domain, are utilized as pharmacologically active compounds (referred to hereinafter as "Therapeutics").

An antibody specific for the TLR4/MD-2 complex or TLR4 can be used to isolate the TLR4/MD-2 complex or a TLR4 polypeptide by standard techniques, such as immunoaffinity, chromatography or immunoprecipitation. Antibodies directed against the TLR4/MD-2 complex or a TLR4 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention, including polyclonal, monoclonal, humanized and fully human antibodies, may be used as therapeutic agents. Such agents will generally be employed to treat or prevent a disease or pathology associated with aberrant TLR4 signaling in a subject. An antibody preparation, preferably one having high specificity and high affinity for its target antigen, is administered to the subject and will generally have an effect due to its binding with the target. Administration of the antibody may abrogate or inhibit or interfere with the signaling function of the target (e.g., the TLR4/MD-2 complex). Administration of the antibody may abrogate or inhibit or interfere with the binding of the target (e.g., TLR4) with an endogenous ligand (e.g., TLR4 or the MD-2 accessory protein) to which it naturally binds. For example, the antibody binds to the target and neutralizes LPS-induced IL-8 production.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding the TLR4/MD-2 complex or a TLR4 protein or a fragment thereof of the invention can be administered for the treatment of disorders associated with aberrant LPS signaling in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of the TLR4/MD-2 complex or a TLR4 protein (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$ is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Chimeric Polypeptides

The chimeric peptides of the invention include a first and second domain operably linked together. The first domain includes at least a portion of a toll-like receptor polypeptide, while the second domain includes at least a portion of an MD accessory protein. The first and second domains can occur in any order in the peptide, and the peptide can include one or more of each domain. The chimeric protein comprises at least one biologically active portion of a toll-like receptor polypeptide or MD accessory protein. The chimeric peptide is soluble. By soluble is meant the ability to dissolve in a fluid.

A "toll-like receptor polypeptide" refers to a polypeptide having an amino acid sequence corresponding to at least a portion of a toll-like receptor polypeptide. A toll-like receptor polypeptide includes, for example, TLRs 1-10 and RP105. The toll-like receptor polypeptide, and/or nucleic acids encoding the toll-like receptor polypeptide, can be constructed using toll-like receptor polypeptide encoding sequences that are known in the art and are described in, e.g. GenBank Accession Nos. (CAH72620; CAH72619; NP_003254; NP_003255; NP_003259; NP_006059; NP_057646; NP_003256; AAH33651; CAD99157; AAM23001; BAB43955; AAF05316; AAK26744; AAF78037; AAF78036; AAF78035; BAB19259; AAF64061; AAF60188; AAF89753; AAF07823; BAA78631; AAC34135; AAC34134; AAC34133; AAC34137) and are incorporated herein by reference in their entirety. Within the chimeric protein the toll-like receptor polypeptide can correspond to all or a portion of a toll-like receptor polypeptide. Preferably the toll-like receptor polypeptide includes the extracellular portion of the polypeptide.

An "MD accessory protein" refers to a polypeptide having an amino acid sequence corresponding to at least a portion of a MD accessory protein. The MD protein is, e.g., MD-1 or MD-2. The MD accessory protein, and/or nucleic acids encoding the MD accessory protein, can be constructed using MD accessory protein encoding sequences that are known in the art and are described in, e.g. GenBank Accession Nos. GenBank Accession Nos. O95711 (MD-1); AAC98152 (MD-1); Q9Y6Y9 (MD-2); NP_056179 (MD-2); AAH20690 (MD-2); and BAA78717 (MD-2). Exemplary MD accessory protein and nucleic acid sequences are is shown in FIGS. 32A, 32B, 33A and 33B. Within the chimeric protein the MD accessory protein can correspond to all or a portion of a MD accessory protein.

The chimeric protein may be linked to one or more additional moieties. For example, the chimeric protein may additionally be linked to a GST fusion protein in which the glycoprotein Ibα fusion protein sequences are fused to the C-terminus of the GST (i.e., glutathione S-transferase) sequences. Such fusion proteins can facilitate the purification of chimeric protein.

In another embodiment, the chimeric protein is includes a heterologous signal sequence (i.e., a polypeptide sequence that is not present in a polypeptide encoded by a toll-like receptor polypeptide or MD accessory protein nucleic acid) at its N-terminus. For example, the native toll-like receptor polypeptide signal sequence can be removed and replaced with a signal sequence from another protein. In certain host cells (e.g., mammalian host cells), expression and/or secretion of chimeric protein can be increased through use of a heterologous signal sequence.

An chimeric protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A glycoprotein Ibα encoding nucleic acid can be cloned into such an expression vector such that the fusion moiety is linked in-frame to the immunoglobulin protein.

Within the chimeric protein, the term "operatively linked" is intended to indicate that the first and second polypeptides are chemically linked (most typically via a covalent bond such as a peptide bond) in a manner that allows for at least one function associated with the toll-like receptor polypeptide and MD accessory protein. When used to refer to nucleic acids encoding the chimeric protein the term operatively linked means that a nucleic acid encoding the toll-like receptor polypeptide or MD accessory protein are fused in-frame to each other. The MD accessory protein can be fused to the N-terminus or C-terminus of the toll-like receptor polypeptide. Optionally, the toll-like receptor polypeptide and MD accessory protein are linked via a spacer arm. Spacer arms provide intramolecular flexibility or adjust intramolecular distances between conjugated moieties and thereby may help preserve biological activity. A spacer arm may be in the form of a polypeptide moiety that includes spacer amino acids, e.g. proline, serine or glycine. Preferably the toll-like receptor polypeptide and MD accessory protein are linked via a flexible glycine/serine linker. Alternatively, a spacer arm may be part of the cross-linking reagent, such as in "long-chain SPDP" (Pierce Chem. Co., Rockford, Ill., cat. No. 21651H).

In other embodiments, the toll-like receptor polypeptide and the MD accessory protein are linked by chemical coupling in any suitable manner known in the art. Many known chemical cross-linking methods are non-specific, i.e.; they do not direct the point of coupling to any particular site on the toll-like polypeptide or MD accessory protein. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, CHEMICAL MODIFICATION OF PROTEINS, Holden-Day, 1974, pp. 39-43. Among these reagents are, for example, J-succinimidyl 3-(2-pyridyldithio) propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonyl-chloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis (succinimidylpropionate) ("DSP"), and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

Also included in the invention are derivatives, fragments, homologs, analogs and variants of the chimeric peptides and nucleic acids encoding these peptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments are less than the length of the corresponding full-length nucleic acid or polypeptide from which the chimeric peptide, or nucleic acid encoding same, is derived. Derivatives and analogs may be full length or other than full length, if the derivative or analog contains a modified nucleic acid or amino acid. Derivatives or analogs of the chimeric peptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of TLR4 to the MD-2 accessory protein, or candidate or test compounds or agents that modulate or otherwise interfere with the signaling function of TLR4 and/or the TLR4/MD-2 complex. Also provided are methods of identifying compounds useful to treat disorders associated with aberrant LPS-signaling. The invention also includes compounds identified in the screening assays described herein.

In one embodiment, the invention provides assays for screening candidate or test compounds which modulate the signaling function of the TLR4/MD-2 complex and/or the interaction between TLR4 and MD-2. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates the signaling function of the TLR4/MD-2 complex and/or the interaction between TLR4 and MD-2. For example, the antibody is monoclonal antibody 18H10 and the antigen is the TLR4/MD-2 complex. Alternatively, the monoclonal antibody is 16G7 or 15C1 or 7E3 and the antigen is the TLR4/MD-2 complex or TLR4.

In another embodiment, a TLR4/MD-2 complex is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with aberrant LPS-signaling.

In another embodiment, a soluble chimeric protein of the invention is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with aberrant LPS-signaling.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a neutralizing antibody, such as monoclonal antibody 18H10, 16G7, 15C1 and/or 7E3, each of which modulates or otherwise interferes with LPS-induced IL-8 production.

The screening methods disclosed herein may be performed as a cell-based assay or as a cell-free assay. The cell-free assays of the invention are amenable to use of both the soluble form or the membrane-bound form of the TLR4 and/or TLR4 when complexed with MD-2, and fragments thereof. In the case of cell-free assays comprising the membrane-bound forms of TLR4 and/or the TLR4/MD-2 complex, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. 18H10, 16G7, 15C1, and/or 7E3) or the antigen (e.g. the TLR4/MD-2 complex and/or a TLR4 protein) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which the TLR4/MD-2 complex or a TLR4 protein or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest (e.g. monoclonal antibody 18H10, 16G7, 15C1 and/or 7E3) bound to the immobilized polypeptide is subsequently incubated with a second, labeled antibody or antibody bound to a coupling agent such as biotin or avidin. This second antibody may be another anti-TLR4/MD-2 complex antibody, another anti-TLR4 antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of the TLR4/MD-2 complex or a TLR4 protein in a biological sample involves obtaining a biological sample from a test subject and contacting the biological sample with a labeled monoclonal antibody according to the invention such that the presence of TLR4/MD-2 complex or TLR4 is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect TLR4/MD-2 complex or TLR4 in a biological sample in vitro as well as in vivo. For example, in vitro techniques for detection of TLR4/MD-2 complex or TLR4 include enzyme linked immunosorbent assays (ELISAs), Western blots, immunoprecipitations, and immunofluorescence. Furthermore, in vivo techniques for detection of TLR4/MD-2 complex or TLR4 include introducing into a subject a labeled anti-TLR4/MD-2 complex or anti-TLR4 antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of TLR4/MD-2 complex or TLR4 in a biological sample. For example, the kit can comprise: a labeled compound or agent capable of detecting TLR4/MD-2 complex or TLR4, when not complexed with MD-2, (e.g., an anti-TLR4/MD-2 complex monoclonal antibody or an anti-TLR4 monoclonal antibody) in a biological sample; means for determining the amount of TLR4/MD-2 complex or TLR4 in the sample; and means for comparing the amount of TLR4/MD-2 complex or TLR4 in the sample with a standard. The compound or agent can be packaged in a suitable container. The kit can further comprise instructions for using the kit to detect TLR4/MD-2 complex or TLR4 in a sample.

The invention will be further described in the following examples, which do not limit the scope of the invention described in the claims.

EXAMPLES

Example 1

Materials and Methods for the Generation of 18H10 Monoclonal Antibody

A. Generation of Stable TLR4/MD-2 Transfectants

Stable TLR4/MD-2 transfectants were generated in CHO-K1 and HEK 293 cells. For CHO-K1 cells, human TLR4 cDNA encoding an N-terminal c-myc epitope tag was cloned into pcDNA3.1(−)hygro (Invitrogen), and human MD-2 cDNA encoding C-terminal c-Myc and Protein C epitope tags was cloned into pcDNA3 (Invitrogen). Both constructs were co-transfected into CHO cells using Fugene 6™ reagent (Roche), according to the manufacturer's guidelines. Antibiotic resistant cells were selected in culture medium containing 500 µg/ml G418 and 250 µg/ml hygromycin B (both from Invitrogen).

To select for cells expressing the TLR4/MD-2 complex, $1 \times 10^7$ cells/ml were incubated in 1×PBS supplemented with 1% BSA and 10 µg/ml anti-protein C monoclonal antibody (Roche). Cells were washed once and then incubated in the same buffer with PE-conjugated goat anti-mouse IgG (H+L) antibody (1:200 dilution; Anwara). Cells were subsequently incubated with anti-PE microbeads (Miltenyi Biotec) and passed through a Midi MACS LS column. Cells retained on the column were eluted and placed back in culture with antibiotic selection. Rounds of sorting were continued until a uniformly positive population of cells expressing the TLR4/MD-2 complex was obtained.

B. Generation of Recombinant MD-2 and Chimeric TLR4/MD-2 Protein

To generate recombinant soluble MD-2, cDNA encoding the protein with C terminal FLAG and 6×HIS tags for detection and purification purposes was cloned into pFASTBAC1 and subsequently inserted into bacmid DNA by homologous recombination. Following generation of a viral stock, Sf9 cells were superinfected. 48 hours later, the recombinant protein was purified from infected cell supernatants using a NiNTA affinity matrix (Qiagen).

To generate the recombinant TLR4/MD-2 chimeric protein, cDNA encoding the extracellular portion of human TLR4 linked to MD-2 via a glycine serine (GGGGS$_3$) linker was assembled using PCR. FLAG and 6×HIS tags were included at the C-terminus of MD-2 for detection and purification purposes. The cDNA cassette was cloned into the baculovirus expression vector pFASTBAC1 (Invitrogen) and subsequently inserted into bacmid DNA by homologous recombination. Following generation of a viral stock, Sf9 cells were superinfected. 48 hours later, the recombinant fusion protein was purified from cell lysates using an anti-FLAG™ M2 MAb affinity matrix (Sigma).

C. Immunization of Mice 8 week old female BALB/c mice (IFFA CREDO) were immunized with a subcutaneous injection (s.c.) of $10^6$ CHO cells/ml in RIBI adjuvant (Sigma) at days 0, 7 and 28 as previously described in Buell et al., Blood 92: 3521-3528 (1998), hereby incorporated by reference in its entirety.

D. Specific Serum Titrations

The mice were bled at days 0 and 14. TLR4/MD-2 specific antibody titers were assessed in the sera by FACS analysis on TLR4/MD-2 transfected 293 cells. Cells were incubated with mice sera at 1:250, 1:2500 and 1:25000 dilutions, washed, incubated with APC-conjugated goat anti-mouse IgG (H+L) antibody (Molecular Probes) and analyzed on a FACScalibur (Becton Dickenson) in the FL-4 channel.

E. B Cell/Myeloma Fusions

Mice having specific TLR4/MD-2 serum antibodies were "hyperboosted" subcutaneously (s.c.) with the chimeric TLR4/MD-2 fusion protein either 3 or 4 days prior to fusion. Draining lymph nodes were obtained as a source of B cells for fusion with the mouse myeloma cell line P3-X63-Ag8.653. B cell extraction and cellular fusions were performed as previously described in Buell et al., Blood 92: 3521-3528 (1998), hereby incorporated by reference in its entirety. Cells were plated at an approximate concentration of $10^4$ myeloma cells/well and grown for 10-14 days in culture medium supplemented with HAT (Sigma).

F. Hybridoma Screening

Supernatants from wells containing viable hybridoma cells were screened on mock transfected cells vs. TLR4/MD-2 transfected myeloma cells for TLR4/MD-2 specificity by FACS analysis. Cells were then incubated with supernatant and goat-anti mouse IgG (H+L) antibody (Molecular Probes). Cells were analyzed on a FACScalibur in the FL-4 channel.

G. Monoclonal Antibody Specificity by FACS

Figure 4:
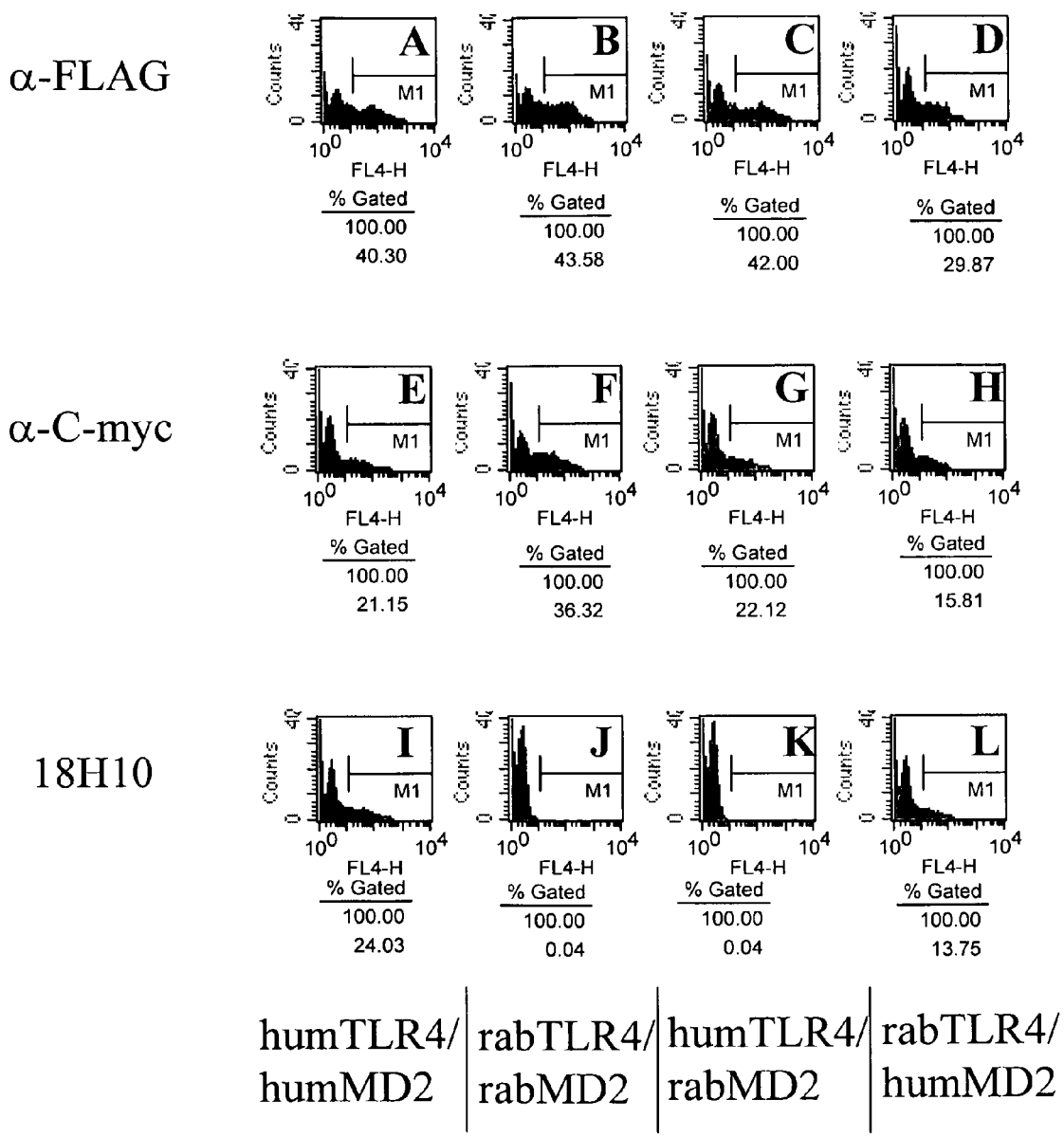
FIG. 4 is a series of graphs depicting the specificity of the 18H10 monoclonal antibody for MD-2. The specificity of the 18H10 antibody is shown by flow cytometry analysis of HEK 293 cells transiently transfected with either human TLR4 and human MD-2 (Panels A, E and I); rabbit TLR4 and rabbit MD-2 (Panels B, F and J); human TLR4 and rabbit MD-2 (Panels C, G and K); or rabbit TLR4 and human MD-2 (Panels D, H and L). Cells were incubated with either α-FLAG™ antibody (to detect TLR4 expression); α-C-myc antibody (to detect MD-2 expression) or the 18H10 monoclonal antibody, followed by an APC-coupled α-mouse (H+L) antibody.

HEK 293 cells were plated in 6 well plates at a density of $2.5 \times 10^5$ cells/well in 2 ml culture medium containing 10% FBS. 16 hours post-plating, cells were transfected with 0.75 µg of the appropriate vector(s) using Fugene™ reagent (Roche) according to the manufacturer's guidelines. 48 hours post-transfection, cells were stained with the appropriate monoclonal antibody (as indicated in FIG. 4) and an APC-coupled goat anti-mouse IgG (H+L) antibody (Molecular Probes) and analyzed using the FACScalibur in the FL-4 channel.

H. Monoclonal Antibody Specificity by Direct ELISA

Recombinant soluble MD-2 with C terminal FLAG and histidine epitope tags was coated at a concentration of 5 µg/ml in 50 µl PBS on ELISA plates (Nunc Maxisorp). Wells were blocked with 200 µl PBS 2% BSA and subsequently incubated with the appropriate MAb at the indicated concentration in PBS 1% BSA. Following 3 wash steps with PBS 0.05% Tween 20, 50 µl HRP conjugated goat anti-mouse IgG (H+L) at a 1:5000 dilution was added to the wells. Following a further wash step, binding was revealed using TMB substrate. Plates were read at a wavelength of 650 nm.

I. Monoclonal Antibody Specificity by Sandwich ELISA

For sample preparation, HEK 293 cells were transfected with the appropriate plasmid constructs using the Fugene 6™ transfection reagent as described in paragraph G above. 48 hours post-transfection, cells were collected and cleared by centrifugation. Cells were subsequently incubated with biotinylated 18H10 (10 µg/ml) and lysed in 20 mM Tris pH 7.4, 150 mM NaCl, 1% NP40 containing COMPLETE™ protease inhibitors (Roche).

To perform the sandwich ELISA, Nunc maxisorp plate wells were coated with 50 µl of the anti-FLAG™ M2 MAb (Sigma) at a concentration of 5 µg/ml in PBS. Wells were blocked with 200 µl PBS 2% BSA and subsequently incubated with 50 µl of the appropriate samples at the indicated dilution. Wells were washed three times with 200 µl PBS 0.05% Tween 20 and incubated with 50 µl of the appropriate antibody (10 µg/ml for biotinylated 18H10 and 12D4, 1 µg/ml for the polyclonal anti-MD-2 MAb). Following a wash step as above, wells were incubated with 50 µl of the appropriate detection antibody (HRP conjugated streptavidin at a dilution of 1:1500 for the biotinylated MAbs and HRP conjugated anti-rabbit IgG (H+L) at a dilution of 1:5000 for the polyclonal rabbit Ab). Following a further wash step, binding was revealed using TMB substrate. Plates were read at a wavelength of 650 nm.

J. Cellular Assay 1

Monoclonal antibody was first purified from hybridoma cell supernatant using protein G affinity chromatography.

TLR4/MD-2 transfected HEK 293 cells were plated in culture medium containing 10% FBS at $5 \times 10^5$ cells/ml in 96 well plates and left to adhere overnight. The culture medium was subsequently removed and replaced with 100 µl culture medium containing 2% FBS and the appropriate monoclonal antibody at twice the desired final concentration for 30 minutes at 37° C. LPS (K12LD25, Sigma) was then added to the cells at a concentration of 30 ng/ml in 100 µl culture medium containing 2% FBS. Cells were incubated at 37° C. for 16 hours and supernatants harvested. IL-8 content was measured by sandwich ELISA using the monoclonal antibody pair 801E and M802B (Endogen).

K. Cellular Assay 2

Human whole blood was diluted 1:4 in RPMI (Sigma) and plated at 100 µl/well in 96 well plates with the appropriate monoclonal antibody at twice the desired final concentration for 30 minutes at 37° C. LPS (K12LD25, Sigma), dosed at twice the desired final concentration, was subsequently added in 100 µl RPMI containing 5 mg/ml HSA and incubated for 6 hours at 37° C. Plates were then centrifuged at 2000 rpm for 5 minutes and the supernatant from each well was retained. IL-8 concentrations were determined by sandwich ELISA using the monoclonal antibody pair 801E and M802B (Endogen), as described above.

L. 18H10 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from three independent subclones of the 18H10 hybridoma was generated by RT-PCR with the mouse ScFv module (Amersham Biosciences) according to the manufacturer's guidelines. Amplified products were cloned into the pGEM-T easy vector (Promega Corp.) and sequenced using the T7 and SP6 primers.

The VH and VL cDNAs were subsequently cloned in mammalian expression vectors containing the human IgG1 and human kappa constant regions respectively in order to express 7E3 as a chimeric MAb ("chimeric 7E3"). To produce recombinant chimeric MAb, HEK 293 cells were plated in 6 well plates at a density of $2.5 \times 10^5$ cells/well in 2 ml culture medium containing 10% FBS. 16 hours post-plating, cells were transfected with 0.75 µg of the appropriate vector(s) using Fugene™ reagent (Roche) according to the manufacturer's guidelines. 48 hours post-transfection, supernatant was harvested and antibody was purified using protein G affinity chromatography.

Example 2

Generation of 18H10 MAbs Directed Against the Human TLR4/MD-2 Complex

Mice immunized with CHO cells expressing surface TLR4/MD-2 were monitored for specific serum titers. Those showing a response to TLR4/MD-2 were "hyperboosted" with recombinant TLR4/MD-2 chimeric protein. This strategy was chosen in order to ensure that the immune system was initially exposed to a conformational TLR4/MD-2 complex whilst minimize the response to non-specific CHO cellular antigens and simultaneously maximizing the TLR4/MD-2-specific response upon hyperboosting. Screening by FACS of supernatants from hybridomas resulting from B cell/myeloma fusions was performed on mock transfected vs. TLR4/MD-2 transfected CHO cells. Monoclonal antibody from one particular clone, referred to herein as 18H10, demonstrated specific binding to TLR4/MD-2 transfected CHO cells (FIG. 1). This antibody was found to have the IgG2b κ isotype, as determined by FACS using the mouse Ig isotyping CBA kit (Beckton Dickenson).

Example 3

18H10 MAb Neutralization of LPS Activity on TLR4/MD-2 Transfected HEK 293 Cells

Figure 2:
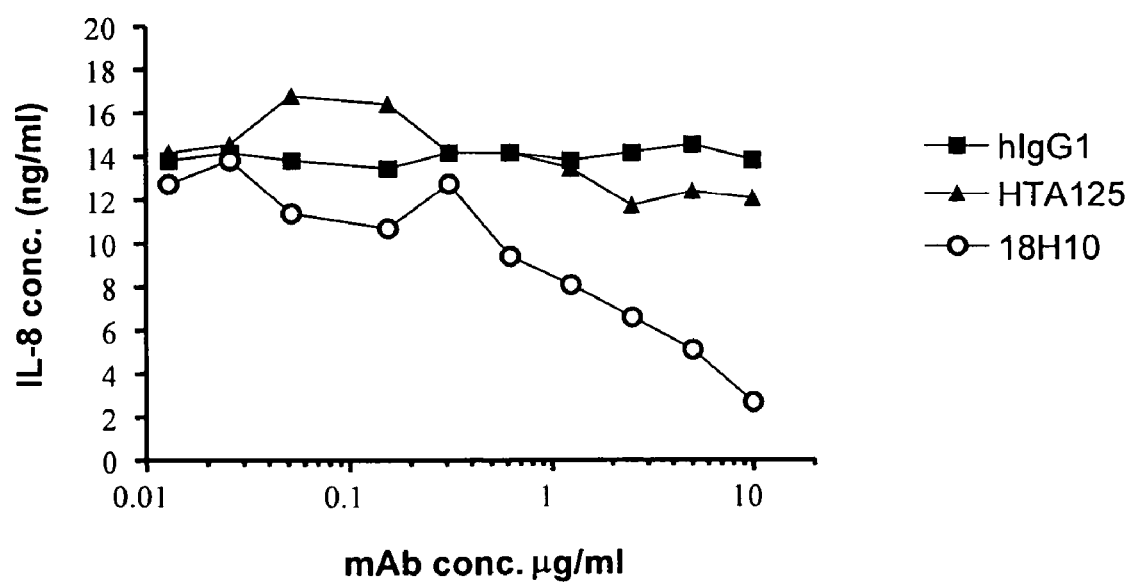
FIG. 2 is a graph depicting inhibition of lipopolysaccharide (LPS)-induced IL-8 production in TLR4/MD-2 transfected HEK 293 cells by the monoclonal antibody 18H10. The cells were incubated with either 18H10, HTA 125 (a commercially available anti-human TLR4 non-blocking MAb) or an antibody control at the indicated concentrations and subsequently incubated with LPS (15 ng/ml). IL-8 levels were assessed 16 hours post LPS treatment.

LPS is known to have the ability to induce IL-8 production in HEK 293 cells transfected with the TLR4/MD-2 complex. The ability of 18H10 to inhibit this IL-8 induction was analyzed by pre-incubating cells with the antibody for 30 minutes prior to LPS administration. FIG. 2 shows that 18H10 inhibited the effects of LPS on HEK 293 cells, even at concentrations below 1 µg/ml.

Example 4

18H10 MAb Neutralization of LPS Activity on Human Whole Blood

The ability of 18H10 to inhibit LPS-induced IL-8 production in human whole blood was tested. 18H10 neutralizing activity was tested in blood from 3 different donors using a range of monoclonal antibody concentrations from 0.5 to 10 µg/ml. FIG. 3 demonstrates that 18H10 significantly reduced the level of IL-8 induced by LPS in all 3 donors, as compared to an isotype matched control. 18H10 was found to be more potent than a previously described α-TLR4 blocking monoclonal antibody (purchased from e-biosciences). These results indicate that the neutralizing epitope recognized by 18H10 on transfected HEK 293 cells is also exposed on the surface on cells in whole blood, and that 18H10 is potent enough to inhibit the activity of LPS in whole blood, even at concentrations below 1 µg/ml.

Example 5

18H10 Specificity

In order to determine the specificity of the 18H10 monoclonal antibody, the fact that 18H10 does not recognize the rabbit ortholog of the TLR4/MD-2 complex (previously cloned) was exploited. cDNAs for either human or rabbit TLR4 with N-terminal FLAG™ epitope tag and either human or rabbit MD-2 with C-terminal c-Myc and protein C epitope tags were transfected in HEK 293 cells in the following combinations: (1) human TLR4 and human MD-2; (2) rabbit TLR4 and rabbit MD-2; (3) human TLR4 and rabbit MD-2; (4) rabbit TLR4 and human MD-2. FIG. 4 shows FACS analysis of these cells following antibody staining, which revealed that 18H10 recognized cells expressing the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by 18H10 is situated on human MD-2 (FIG. 4).

Figure 5A:
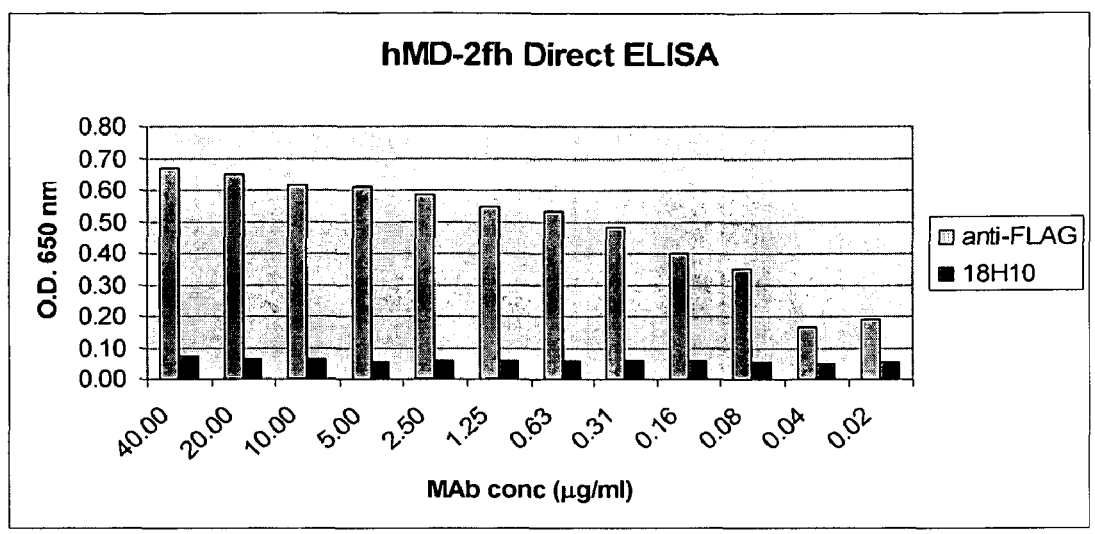
FIG. 5A is a graph demonstrating the lack of specificity of 18H10 for recombinant soluble MD-2 purified from baculovirus-infected insect cell supernatants as determined by ELISA. Protein was coated directly on 96-well plates (5 µg/ml) followed by purified MAb at the indicated concentration and anti-mouse IgG (H+L) HRP.

Although 18H10 shows specificity for MD-2, it was determined that 18H10 only recognizes MD-2 in the context of its interaction with TLR4. Using direct ELISA, no binding of 18H10 to recombinant soluble MD-2 generated with the baculovirus expression system was detected (FIG. 5a). In addition, FIG. 5b reveals that 18H10 only bound to a complex of TLR4 and MD-2 as shown from co-transfected cell lysates, and did not recognize either MD-2 alone in transfected cell lysates/supernatants or TLR4 alone in transfected cell lysates. These data indicate that 18H10 is specific for the TLR4/MD-2 complex and does not recognize either component of the complex separately.

Example 6

18H10 VH and VL Sequences

VH and VL sequences from the 18H10 hybridoma clone were amplified from total RNA by RT-PCR. Sequence analysis is shown in FIGS. 6A-6F.

The 18H10 antibody includes a heavy chain variable region (SEQ ID NO:2, FIG. 6B) encoded by the nucleic acid sequence of SEQ ID NO:1 shown in FIG. 6A, and a light chain variable region (SEQ ID NO:7, FIG. 6E) encoded by the nucleic acid sequence of SEQ ID NO:6 shown in FIG. 6D. The amino acids encompassing the complementarity determining regions (CDR) as defined by Chothia et al. 1989, E. A. Kabat et al., 1991 are highlighted in underlined and italicized text in FIGS. 6B and 6E and shown in FIGS. 6C and 6F. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 18H10 antibody have the following sequences: DSYIH (SEQ ID NO:3); WTDPENVNSIYDPRFQG (SEQ ID NO:4), and GYNGVYYAMDY (SEQ ID NO:5). The light chain CDRs of the 18H10 antibody have the following sequences: SASSSVIYMH (SEQ ID NO:8); RTYNLAS (SEQ ID NO:9); and HQWSSFPYT (SEQ ID NO:10).

Example 7

Chimeric 18H10 Binds to hTLR4 hMD2 Transfected CHO Cells

In order to demonstrate the specificity of the cloned 18H10 VH and VL for the hTLR4/MD-2 complex, FACS analysis was performed on hTLR4/MD-2 transfected CHO cells using the chimeric 18H10 MAb (FIG. 6). Specific binding of MAb at the indicated concentration was detected using an APC-labeled goat-anti-human IgG (H+L) secondary antibody. An irrelevant isotype-matched IgG1 MAb was used as a control.

Example 8

Figure 7:
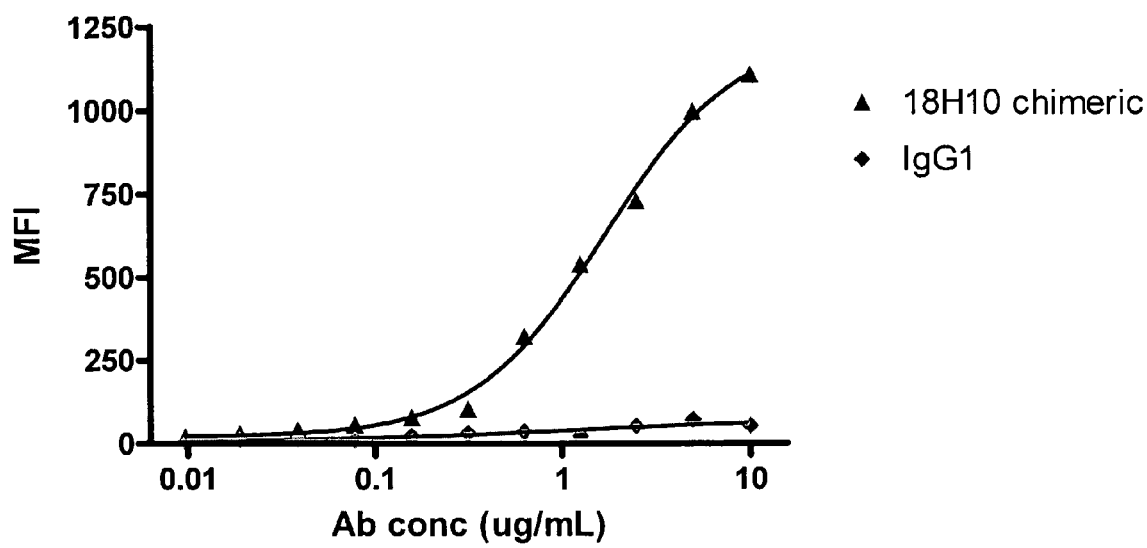
FIG. 7 is a graph depicting that the VH and VL nucleotide sequence of 18H10 expressed as a chimeric MAb ("chimeric 18H10") is capable of binding specifically to the human TLR4/MD-2 complex on the surface of transfected CHO cells. MAb binding to the TLR4/MD-2 transfected CHO cells is shown by flow cytometry using chimeric 18H10 or an isotype matched control MAb at the concentrations indicated.
Figure 8:
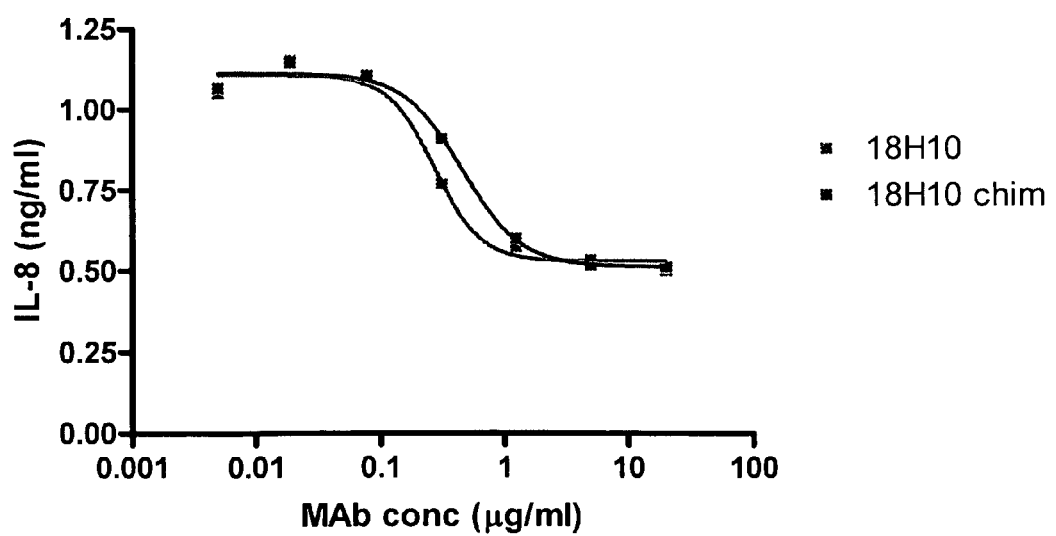
FIG. 8 is a graph depicting inhibition of lipopolysaccharide (LPS)-induced IL-8 production in TLR4/MD-2 transfected HEK 293 cells by the chimeric 18H10 MAb. Cells were incubated with 18H10, or chimeric 18H10 at the indicated concentrations and subsequently incubated with LPS (15 ng/ml). IL-8 levels were assessed 16 hours post LPS-treatment. Inhibition of LPS-induced IL-8 production by the chimeric 18H10 was similar to the inhibition by the 18H10 mouse MAb of the invention.

Chimeric 18H10 Inhibits LPS-Induced IL-8 Production in hTLR4 hMD2 Transfected HEK 293 Cells In order to demonstrate the neutralizing capacity of the cloned 18H10 VH and VL for LPS, the ability of 18H10 to inhibit LPS dependent IL-8 induction of hTLR4/MD-2 transfected HEK 293 cells was tested (as described above). FIG. 7 shows that chimeric 18H10 inhibited the effects of LPS on HEK 293 cells in a manner very similar to that of the original 18H10 mouse MAb.

Example 9

Materials and Methods for the Generation of 16G7 Monoclonal Antibody

A. Generation of Stable TLR4/MD-2 Transfectants

Stable TLR4/MD-2 transfectants were generated in CHO-K1 and HEK 293 cells. For CHO-K1 cells, human TLR4 cDNA encoding an N-terminal c-myc epitope tag was cloned into pcDNA3.1 (−)hygro (Invitrogen), and human MD-2 cDNA encoding C-terminal c-Myc and Protein C epitope tags was cloned into pcDNA3 (Invitrogen). Both constructs were co-transfected into CHO cells using Fugene 6™ reagent (Roche), according to the manufacturer's guidelines. Antibiotic resistant cells were selected in culture medium containing 500 µg/ml G418 and 250 µg/ml hygromycin B (both from Invitrogen).

For HEK 293 cells, human TLR4 cDNA encoding an N-terminal FLAG™ epitope tag was cloned into pcDNA3.1 (−)hygro (Invitrogen), and human MD-2 cDNA encoding C-terminal FLAG™ and 6× Histidine epitope tags was cloned into pcDNA3 (Invitrogen). Both constructs were transfected into HEK 293 cells, and antibiotic resistant cells were selected in culture medium containing 500 µg/ml G418 and 250 µg/ml hygromycin B (both from Invitrogen), as described above.

To select for cells expressing the TLR4/MD-2 complex, $1 \times 10^7$ cells/ml were incubated in 1×PBS supplemented with 1% BSA and either 10 µg/ml anti-protein C monoclonal antibody (for CHO cells; Roche) or anti-FLAG monoclonal antibody (for 293 cells; Sigma). Cells were washed once and then incubated in the same buffer with PE-conjugated goat anti-mouse IgG (H+L) antibody (1:200 dilution; Anwara). Cells were subsequently incubated with anti-PE microbeads (Miltenyi Biotec) and passed through a Midi MACS LS column. Cells retained on the column were eluted and placed back in culture with antibiotic selection. Rounds of sorting were continued until a uniformly positive population of cells expressing the TLR4/MD-2 complex was obtained.

B. Immunization of Mice 8 week old female BALB/c mice (IFFA CREDO) were immunized as described above in Example 1, subsection C.

C. Specific Serum Titrations

Mice sera titrations were performed as described above in Example 1, subsection D.

D. B Cell/Myeloma Fusions

Mice having specific TLR4/MD-2 serum antibodies were "hyperboosted" subcutaneously (s.c.) with TLR4/MD-2 transfected HEK 293 either 3 or 4 days prior to fusion. Draining lymph nodes were obtained as a source of B cells for fusion with the mouse myeloma cell line P3-X63-Ag8.653. B cell extraction and cellular fusions were performed as previously described in Buell et al., Blood 92: 3521-3528 (1998), hereby incorporated by reference in its entirety. Cells were plated at an approximate concentration of $10^4$ myeloma cells/well and grown for 10-14 days in culture medium supplemented with HAT (Sigma).

E. Hybridoma Screening

Hybridomas were Screened as Described Above in Example 1, Subsection F.

F. Monoclonal Antibody Specificity

The specificity of the 16G7 monoclonal antibody was determined as described above in Example 1, subsection G.

G. Cellular Assay 1

Cellular Assay I was performed as described above in Example 1, subsection J.

H. Cellular Assay 2

Cellular Assay II was performed as described above in Example 1, subsection K.

I. 16G7 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from the 16G7 clone was generated by RT-PCR with the mouse ScFv module (Amersham Biosciences) according to the manufacturer's guidelines. Amplified products were cloned into the pGEM-T easy vector (Promega Corp.) and sequenced using the T7 and SP6 primers.

Example 10

Generation of 16G7 MAbs Directed Against the Human TLR4/MD-2 Complex

Figure 9:
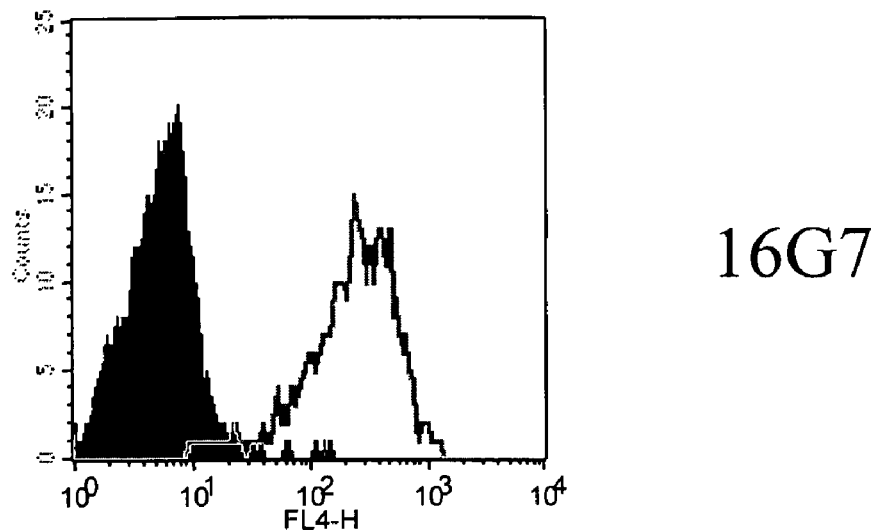
FIG. 9 is a graph depicting the binding of an monoclonal antibody of the invention, 16G7, to the TLR4/MD-2 complex. Specificity of binding is shown by flow cytometry using mock-transfected or TLR4/MD-2 transfected cells. The results using mock transfected cells are shown in the filled graph (left), while the results using TLR4/MD-2 transfected cells are shown as in the outline graph (right).

Mice immunized with CHO cells expressing surface TLR4/MD-2 were monitored for specific serum titers. Those showing a response to TLR4/MD-2 were "hyperboosted" with HEK 293 TLR4/MD-2 transfectants. This strategy was chosen in order to minimize the response to non-specific CHO cellular antigens, while simultaneously maximizing the TLR4/MD-2-specific response. Screening by FACS of supernatants from hybridomas resulting from B cell/myeloma fusions was performed on mock transfected vs. TLR4/MD-2 transfected CHO cells. Monoclonal antibody from a specific clone, referred to herein as 16G7, demonstrated specific binding to TLR4/MD-2 transfected CHO cells (FIG. 9). 16G7 was found to have the IgG1 κ isotype, as determined by FACS using the mouse Ig isotyping CBA kit (Beckton Dickenson).

Example 11

16G7 Neutralization of LPS Activity on TLR4/MD-2 Transfected HEK 293 Cells

Figure 10:
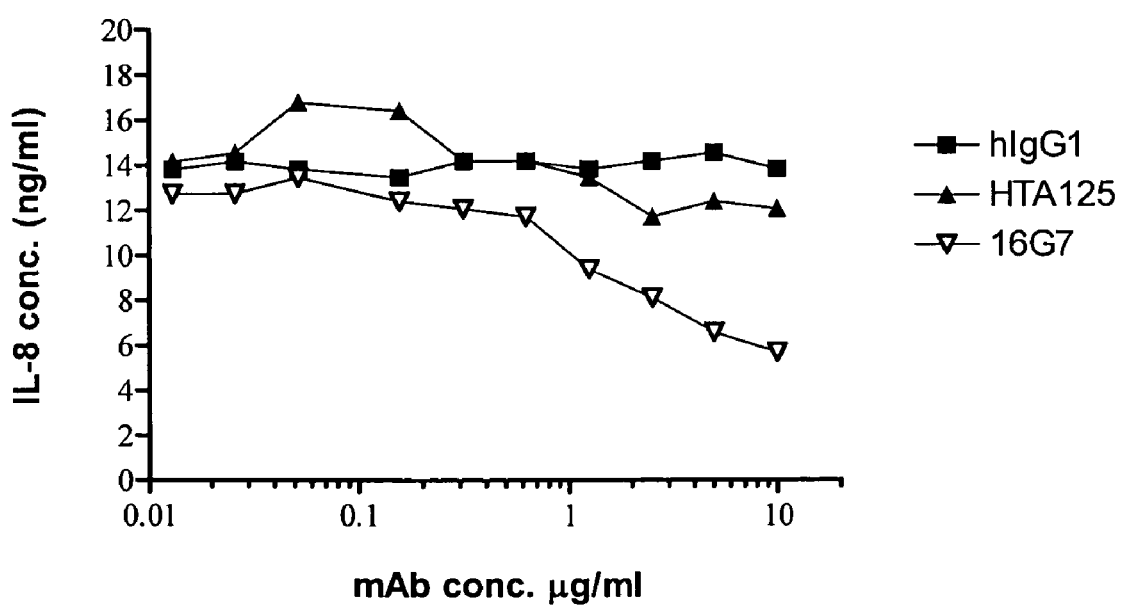
FIG. 10 is a graph depicting inhibition of lipopolysaccharide (LPS)-induced IL-8 production in TLR4/MD-2 transfected HEK 293 cells by the monoclonal antibody 16G7. The cells were incubated with the 16G7 monoclonal antibody, the HTA 125 anti-TLR4 MAb or an antibody control at the indicated concentrations and subsequently incubated with LPS (15 ng/ml). IL-8 levels were assessed 16 hours post LPS treatment.

LPS is known to have ability to induce IL-8 production in HEK 293 cells transfected with the TLR4/MD-2 complex. The ability of 16G7 to inhibit this IL-8 induction was analyzed by pre-incubating cells with each antibody for 30 minutes prior to LPS administration. FIG. 10 shows that 16G7 inhibited the effects of LPS on HEK 293 cells, even at sub-microgram/ml concentrations.

Example 12

16G7 Neutralization of LPS Activity on Human Whole Blood

Figure 11:
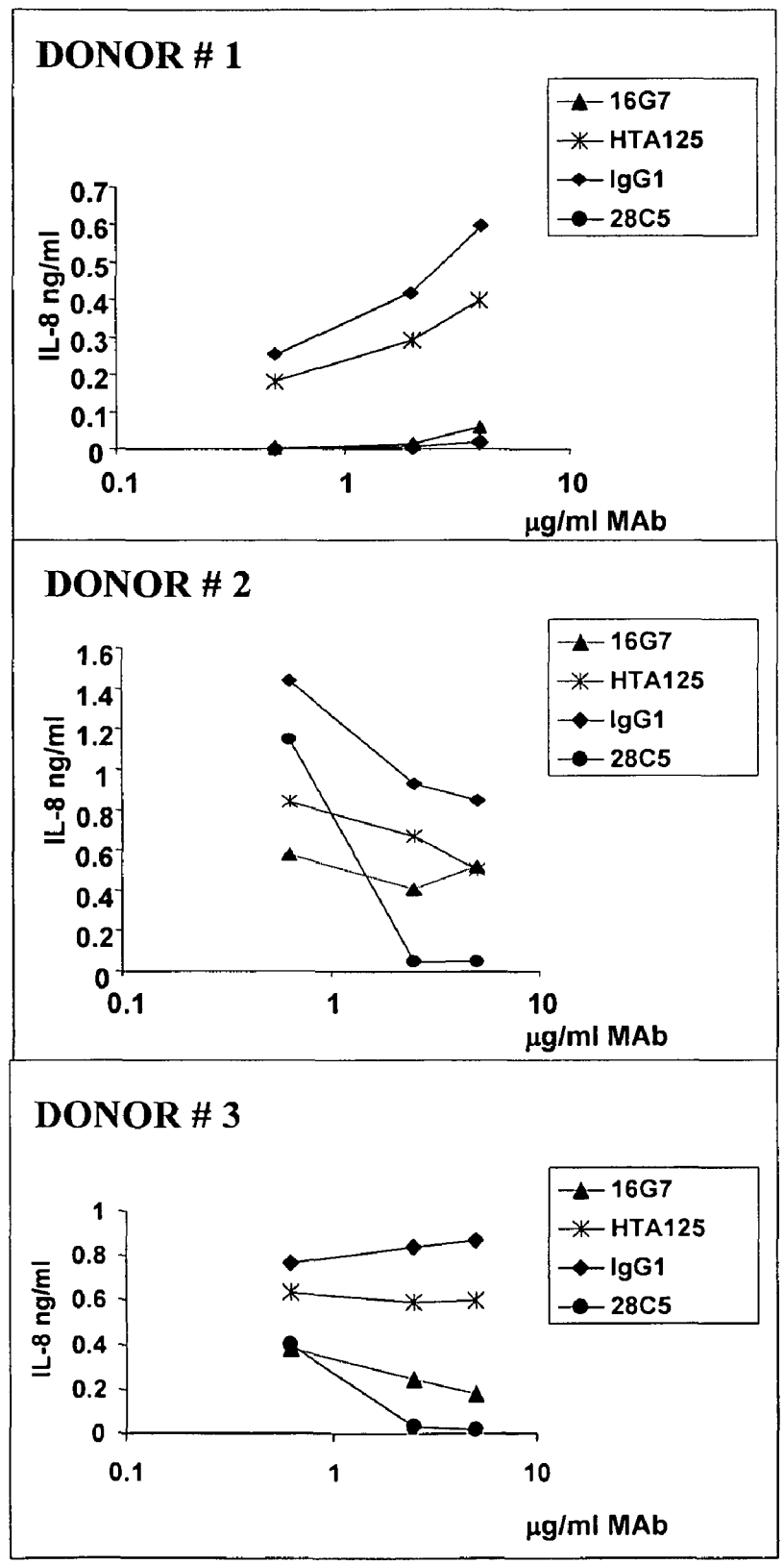
FIG. 11 is a series of graphs depicting inhibition of LPS-induced IL-8 production in human whole blood by the monoclonal antibody 16G7. Whole blood was drawn from 3 healthy volunteers, treated with heparin and diluted 1:4 in RPMI medium. The following antibodies were added at the concentrations indicated: Isotype matched control; HTA125 (anti-human TLR4 non-blocking monoclonal antibody); 16G7 and 28C5 (anti-human CD14 blocking monoclonal antibody). LPS was subsequently added for a final concentration of 10 ng/ml.

The ability of 16G7 to inhibit LPS-induced IL-8 production in human whole blood was tested. 16G7 neutralizing activity was tested in blood from 3 different donors using a range of monoclonal antibody concentrations from 0.5 to 5 µg/ml. FIG. 11 demonstrates that 16G7 significantly reduced the level of IL-8 induced by LPS in all 3 donors, as compared to an isotype matched control. 16G7 was found to be more potent than a previously described α-TLR4 blocking monoclonal antibody (from e-biosciences). (See Shimazu et al. J. Exp. Med. 189: 1777-1782 (1999)). In some cases, 16G7 was found to be as potent as an α-CD14 blocking monoclonal antibody that was also included in the study. (See Kirkland et al. J. Biol. Chem. 268: 24818-24823 (1993)). These results indicate that the neutralizing epitope recognized by 16G7 on transfected HEK 293 cells is also exposed on the surface on cells in whole blood, and that 16G7 is potent enough to inhibit the activity of LPS in whole blood, even at concentrations below 1 µg/ml.

Example 13

16G7 Specificity

In order to determine the specificity of the 16G7 monoclonal antibody, the fact that 16G7 does not recognize the rabbit ortholog of the TLR4/MD-2 complex (previously cloned) was exploited. cDNAs for either rabbit or human TLR4 with N-terminal FLAG™ epitope tag and MD-2 with C-terminal c-Myc and protein C epitope tags were transfected in HEK 293 cells in the following combinations: (1) rabbit TLR4 and rabbit MD-2; (2) human TLR4 and human MD-2; (3) rabbit TLR4 and human MD-2; (4) human TLR4 and rabbit MD-2. FIG. 12 shows FACS analysis of these cells following antibody staining, which revealed that 16G7 recognized cells expressing the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by 16G7 is situated on human TLR4 (FIG. 12).

Example 14

16G7 VH and VL Sequences

VH and VL sequences from the 16G7 hybridoma clone were amplified from total RNA by RT-PCR. Sequence analysis is shown in FIGS. 13A-13F. Alignment of the 16G7 VH and VL nucleotide sequences with known mouse VH and VL sequences (using the International Immunogenetics Information System; which can be found at http://imgt.cines.fr) reveals that the 16G7 VH sequence most closely resembles the IgHV1 subfamily, while the 16G7 VL belongs to the IgKV1 subfamily.

The 16G7 antibody includes a heavy chain variable region (SEQ ID NO:12, FIG. 13B) encoded by the nucleic acid sequence of SEQ ID NO:11 shown in FIG. 13A, and a light chain variable region (SEQ ID NO:17, FIG. 13E) encoded by the nucleic acid sequence of SEQ ID NO:16 shown in FIG. 13D. The amino acids encompassing the CDR as defined by Chothia et al. 1989, E. A. Kabat et al., 1991 are highlighted in underlined and italicized text in FIGS. 13B and 13E and shown in FIGS. 13C and 13F. The heavy chain CDRs of the 16G7 antibody have the following sequences: DYWIE (SEQ ID NO:13); EILPGSGSTNYNEDFKD (SEQ ID NO:14); and EERAYYFGY (SEQ ID NO:15). The light chain CDRs of the 16G7 antibody have the following sequences: RSSQSLENSNGNTYLN (SEQ ID NO:18); RVSNRFS (SEQ ID NO:19); and LQVTHVPPT (SEQ ID NO:20).

Example 15

Materials and Methods for the Generation of 15C1 Monoclonal Antibody

A. Generation of Stable TLR4/MD-2 Transfectants

Stable TLR4/MD-2 transfectants were generated in CHO-K1 and HEK 293 cells as described above in Example 9, subsection A.

B. Generation of Recombinant MD-2 and Chimeric TLR4/MD-2 Protein

To generate recombinant soluble MD-2, cDNA encoding the protein with C terminal FLAG and 6×HIS tags for detection and purification purposes was cloned into pFASTBAC1 and subsequently inserted into bacmid DNA by homologous recombination. Following generation of a viral stock, Sf9 cells were superinfected. 48 hours later, the recombinant protein was purified from infected cell supernatants using a NiNTA affinity matrix (Qiagen).

To generate the recombinant TLR4/MD-2 chimeric protein, cDNA encoding the extracellular portion of human TLR4 linked to MD-2 via a glycine serine (GGGGS$_3$) linker was assembled using PCR. FLAG and 6×HIS tags were included at the C-terminus of MD-2 for detection and purification purposes. The cDNA cassette was cloned into the baculovirus expression vector pFASTBAC1 (Invitrogen) and subsequently inserted into bacmid DNA by homologous recombination. Following generation of a viral stock, Sf9 cells were superinfected. 48 hours later, the recombinant fusion protein was purified from cell lysates using an anti-FLAG™ M2 MAb affinity matrix (Sigma).

C. Immunization of Mice 8 week old female BALB/c mice (IFFA CREDO) were immunized as described above in Example 1, subsection C.

D. Specific Serum Titrations

Mice serum titrations were performed as described above in Example 1, subsection D.

E. B Cell/Myeloma Fusions

B cell extraction and cellular fusion were performed and analyzed as described above in Example 9, subsection D.

F. Hybridoma Screening

Hybridoma screening was performed as described above in Example 1, subsection F.

G. Monoclonal Antibody Specificity

The specificity of the 15C1 monoclonal antibody was determined as described above in Example 1, subsection G.

H. Cellular Assay 1

Cellular Assay I was performed as described above in Example 1, subsection J.

I. Cellular Assay 2

Cellular Assay II was performed as described above in Example 1, subsection K.

J. 15C1 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from the 15C1 clone was generated by RT-PCR with the mouse ScFv module (Amersham Biosciences) according to the manufacturer's guidelines. Amplified products were cloned into the pGEM-T easy vector (Promega Corp.) and sequenced using the T7 and SP6 primers.

The VH and VL cDNAs were subsequently cloned in mammalian expression vectors containing the human IgG1 and human kappa constant regions respectively in order to express 15C1 as a chimeric MAb ("chimeric 15C1"). To produce recombinant chimeric MAb, HEK 293 cells were plated in 6 well plates at a density of 2.5×10$^5$ cells/well in 2 ml culture medium containing 10% FBS. 16 hours post-plating, cells were transfected with 0.75 μg of the appropriate vector(s) using Fugene™ reagent (Roche) according to the manufacturer's guidelines. 48 hours post-transfection, supernatant was harvested and antibody was purified using protein G affinity chromatography.

Example 16

Generation of MAbs Directed Against the Human TLR4/MD-2 Complex

Figure 14:
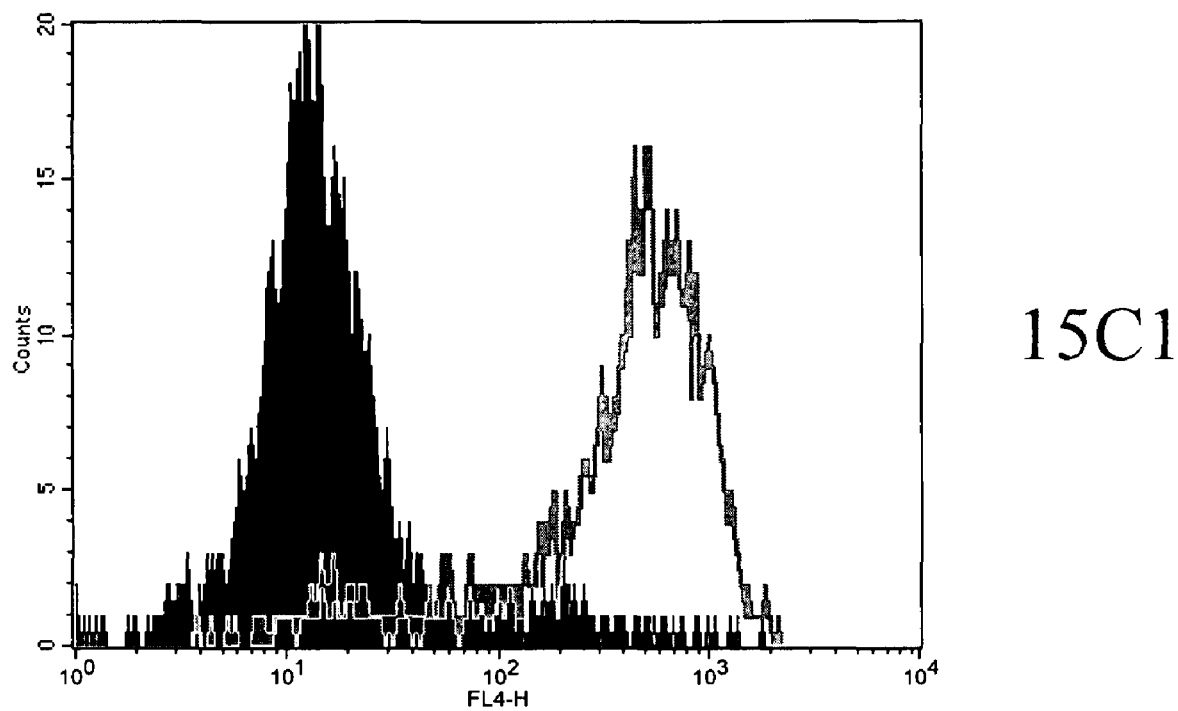
FIG. 14 is a graph depicting the binding of a monoclonal antibody of the invention, 15C1, to the TLR4/MD-2 complex. Specificity of binding is shown by flow cytometry using mock transfected or TLR4/MD-2 transfected cells. The results using mock-transfected cells are shown in the filled graph (left), while the results using TLR4/MD-2 transfected cells are shown as in the outline graph (right).

Mice immunized with CHO cells expressing surface TLR4/MD-2 were monitored for specific serum titers. Those showing a response to TLR4/MD-2 were "hyperboosted" with HEK 293 TLR4/MD-2 transfectants. This strategy was chosen in order to minimize the response to non-specific CHO cellular antigens, while simultaneously maximizing the TLR4/MD-2-specific response. Screening by FACS of supernatants from hybridomas resulting from B cell/myeloma fusions was performed on mock-transfected vs. TLR4/MD-2-transfected CHO cells. Monoclonal antibody from a specific clone, referred to herein as 15C1, demonstrated specific binding to TLR4/MD-2 transfected CHO cells (FIG. 14). 15C1 was found to have the IgG1 κ isotype, as determined by FACS using the mouse Ig isotyping CBA kit (Beckton Dickenson).

Example 17

Neutralization of LPS Activity on TLR4/MD-2 Transfected HEK 293 Cells

Figure 15:
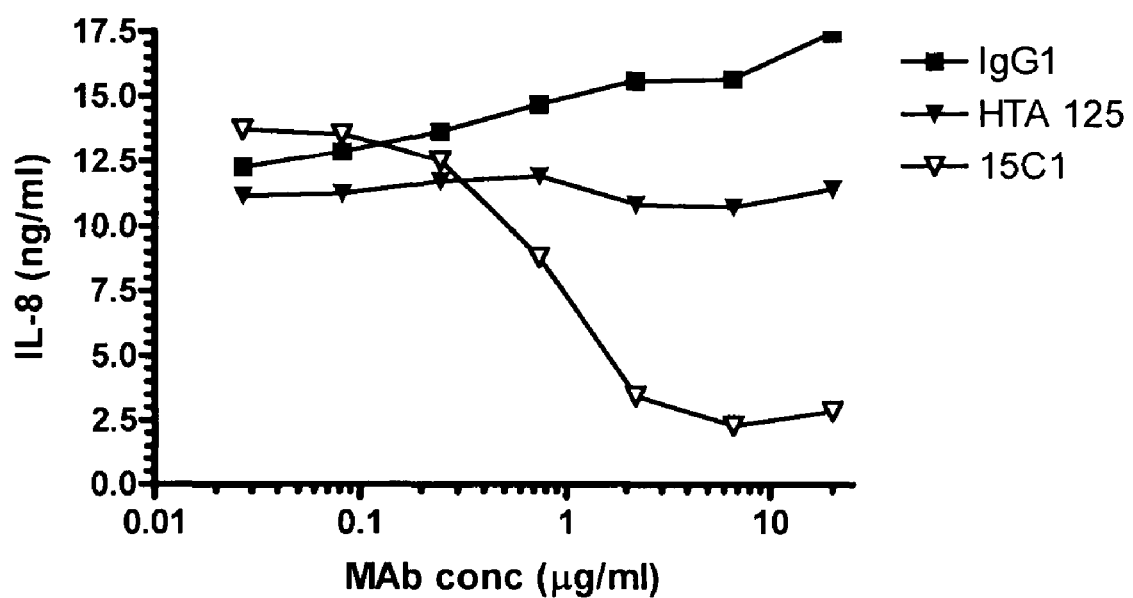
FIG. 15 is a graph depicting inhibition of lipopolysaccharide (LPS)-induced IL-8 production in TLR4/MD-2 transfected HEK 293 cells by the monoclonal antibody 15C1. The cells were incubated with the 15C1 monoclonal antibody, HTA 125 (anti-human TLR4 non-blocking monoclonal antibody) and an isotype-matched control (IgG1) at the indicated concentrations and subsequently incubated with LPS (15 ng/ml). IL-8 levels were assessed 16 hours post LPS treatment.

LPS is known to have ability to induce IL-8 production in HEK 293 cells transfected with the TLR4/MD-2 complex. The ability of 15C1 to inhibit this IL-8 induction was analyzed by pre-incubating cells with each antibody for 30 minutes prior to LPS administration. FIG. 15 shows that 15C1 inhibited the effects of LPS on HEK 293 cells, even at sub-microgram/ml concentrations.

Example 18

Neutralization of LPS Activity on Human Whole Blood

The ability of 15C1 to inhibit LPS-induced IL-8 production in human whole blood was tested. 15C1 neutralizing activity was tested in blood from 3 different donors using a range of monoclonal antibody concentrations from 0.5 to 5 μg/ml. FIG. 16 demonstrates that 15C1 significantly reduced the level of IL-8 induced by LPS in all 3 donors, as compared to an isotype matched control. 15C1 was found to be more potent than a previously described α-TLR4 blocking monoclonal antibody (from e-biosciences). (See Shimazu et al. J. Exp. Med. 189: 1777-1782 (1999)). In some cases, 15C1 was found to be as potent as an α-CD14 blocking monoclonal antibody that was also included in the study. (See Kirkland et al. J. Biol. Chem. 268: 24818-24823 (1993)). These results indicate that the neutralizing epitope recognized by 15C1 on transfected HEK 293 cells is also exposed on the surface on cells in whole blood, and that 15C1 is potent enough to inhibit the activity of LPS in whole blood, even at concentrations below 1 μg/ml.

Example 19

15C1 Specificity

Figure 17:
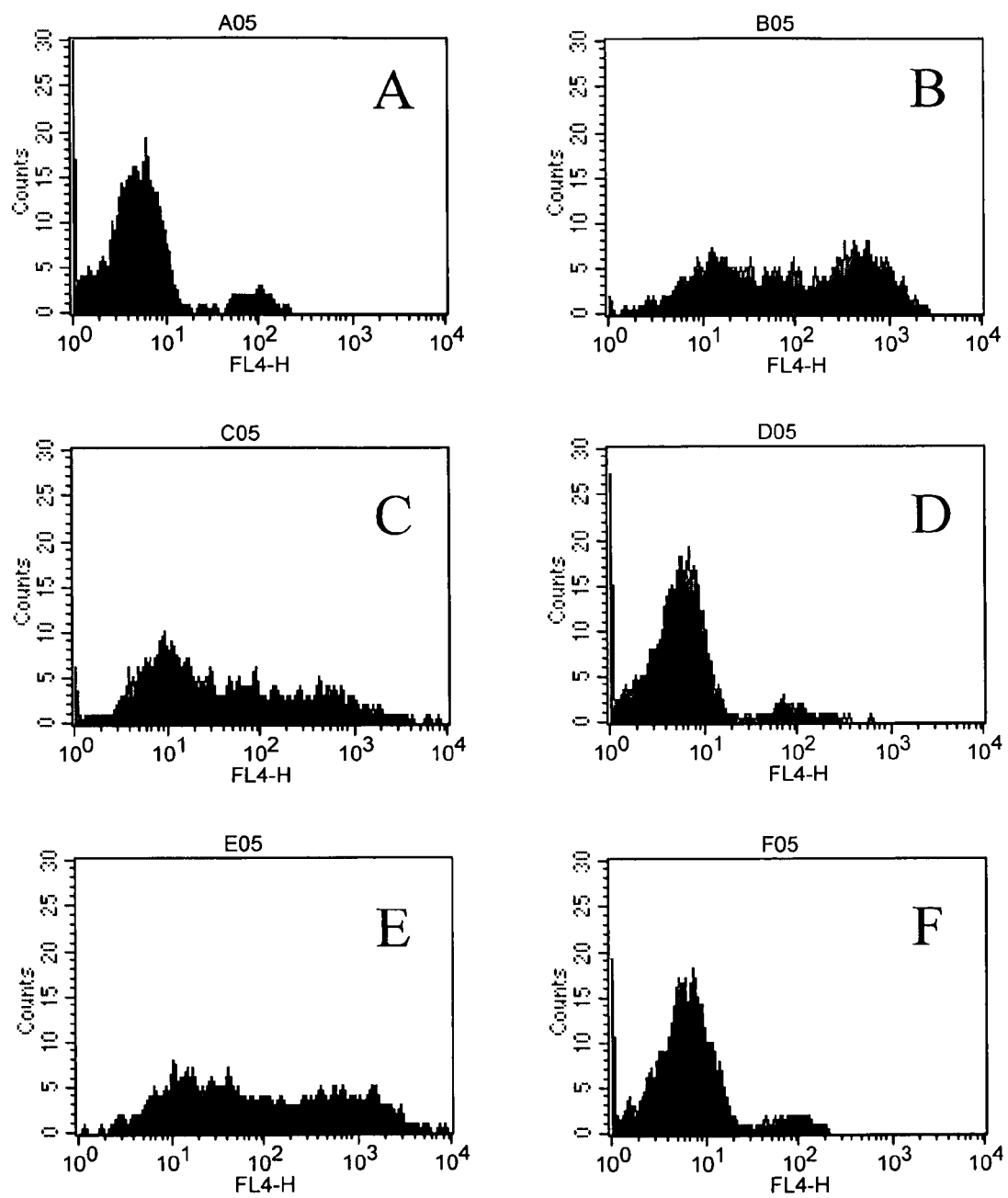
FIG. 17 is a series of graphs depicting the specificity of the 15C1 monoclonal antibody for TLR4. The specificity of the 15C1 antibody is shown by flow cytometry analysis of HEK 293 cells transiently transfected with either mock vector, i.e., empty vector (Panel A), human TLR4 (Panel B), human TLR4 and human MD-2 (Panel C), rabbit TLR4 and rabbit MD-2 (Panel D), human TLR4 and rabbit MD-2 (Panel E), or rabbit TLR4 and human MD-2 (Panel F). Cells were incubated with the 15C1 monoclonal antibody (10 μg/ml), followed by an APC-coupled α-mouse (H+L) antibody.

In order to determine the specificity of the 15C1 monoclonal antibody, the fact that 15C1 does not recognize the rabbit ortholog of the TLR4/MD-2 complex (previously cloned) was exploited. cDNAs for either rabbit or human TLR4 with N-terminal FLAG™ epitope tag and MD-2 with C-terminal c-Myc and protein C epitope tags were transfected in HEK 293 cells in the following combinations: (1) mock vector (2) human TLR4 alone (3) human TLR4 and human MD-2 (4) rabbit TLR4 and rabbit MD-2; (5) human TLR4 and rabbit MD-2; (6) rabbit TLR4 and human MD-2. FIG. 17 shows FACS analysis of these cells following antibody staining, which revealed that 15C1 recognized cells expressing human TLR4 alone, the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by 15C1 is situated on human TLR4 (FIG. 17).

Example 20

15C1 VH and VL Sequences

VH and VL sequences from the 15C1 hybridoma clone were amplified from total RNA by RT-PCR. Sequence analysis is shown in FIGS. 18A-18F.

The 15C1 antibody includes a heavy chain variable region (SEQ ID NO:22, FIG. 18B) encoded by the nucleic acid sequence of SEQ ID NO:21 shown in FIG. 18A, and a light chain variable region (SEQ ID NO:27, FIG. 18E) encoded by the nucleic acid sequence of SEQ ID NO:26 shown in FIG. 18D. The amino acids encompassing the CDR as defined by Chothia et al. 1989, E. A. Kabat et al., 1991 are highlighted in underlined and italicized text in FIGS. 18B and 18E and shown in FIGS. 18C and 18F. The heavy chain CDRs of the 15C1 antibody have the following sequences: GGYSWH (SEQ ID NO:23); YIHYSGYTDFNPSLKT (SEQ ID NO:24); and KDPSDGFPY (SEQ ID NO:25). The light chain CDRs of the 15C1 antibody have the following sequences: RASQSISDHLH (SEQ ID NO:28); YASHAIS (SEQ ID NO:29); and QNGHSFPLT (SEQ ID NO:30).

Example 21

Chimeric 15C1 Binds to hTLR4 hMD2 Transfected CHO Cells

Figure 19:
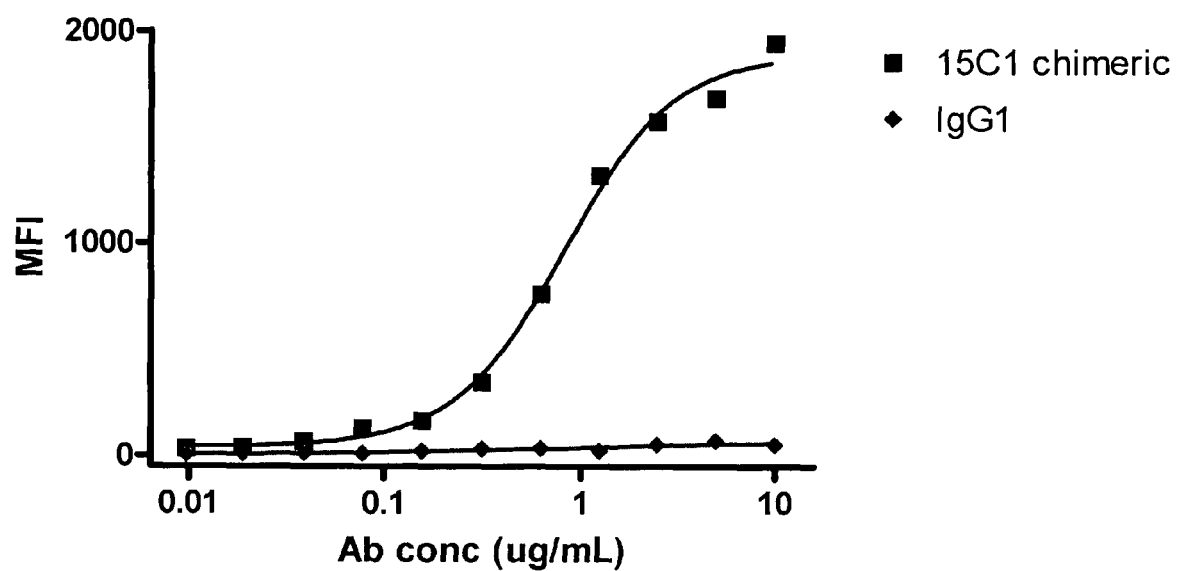
FIG. 19 is a graph depicting that the VH and VL nucleotide sequence of 15C1 expressed as a chimeric MAb ("chimeric 15C1") is capable of binding specifically to the human TLR4/MD-2 complex on the surface of transfected CHO cells. MAb binding to the TLR4/MD-2 complex is shown by flow cytometry using chimeric 15C1 or an isotype matched control monoclonal antibody at the indicated concentration.

In order to demonstrate the specificity of the cloned 15C1 VH and VL for the hTLR4/MD-2 complex, FACS analysis on hTLR4/MD-2 transfected CHO cells using the chimeric 15C1 MAb was performed (FIG. 19). Specific binding of MAb at the indicated concentration was detected using an APC-labeled goat-anti-human IgG (H+L) secondary antibody. An irrelevant isotype-matched IgG1 MAb was used as a control.

Example 22

Figure 20:
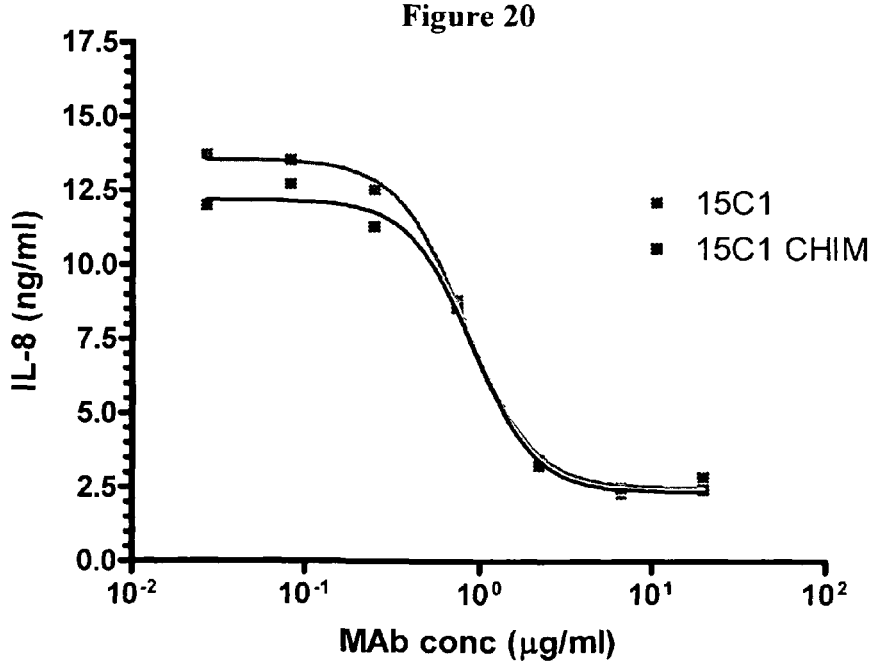
FIG. 20 is a graph depicting inhibition of lipopolysaccharide (LPS)-induced IL-8 production in TLR4/MD-2 transfected HEK 293 cells by the chimeric 15C1 MAb. Cells were incubated with 15C1 or chimerical 15C1 at the concentrations indicated and subsequently incubated with LPS (15 ng/ml). IL-8 levels were assessed 16 hours post LPS treatment. Inhibition of LPS-induced IL-8 production by the chimeric 15C1 was similar to the inhibition by the 15C1 mouse MAb of the invention.

Chimeric 15C1 Inhibits LPS-Induced IL-8 Production in hTLR4 hMD2 Transfected HEK 293 Cells In order to demonstrate the neutralizing capacity of the cloned 15C1 VH and VL for LPS, the ability of 15C1 to inhibit LPS dependent IL-8 induction of hTLR4/MD-2 transfected HEK 293 cells was tested (as described above). FIG. 20 shows that chimeric 15C1 inhibited the effects of LPS on HEK 293 cells in a manner very similar to that of the 15C1 MAb.

Example 23

Materials and Methods for the Generation of 7E3 Monoclonal Antibody

A. Generation of Stable TLR4/MD-2 Transfectants

Stable TLR4/MD-2 transfectants were generated in CHO-K1 and HEK 293 cells as described above in Example 9, subsection A.

B. Generation of Recombinant MD-2 and Chimeric TLR4/MD-2 Protein

Recombinant soluble MD-2 was generated as described above in Example 15, subsection B.

To generate the recombinant TLR4/MD-2 chimeric protein, cDNA encoding the extracellular portion of human TLR4 linked to MD-2 via a glycine serine (GGGGS$_3$) linker was assembled using PCR. FLAG and 6×HIS tags were included at the C-terminus of MD-2 for detection and purification purposes. The cDNA cassette was cloned into the baculovirus expression vector pFASTBAC1 (Invitrogen) and subsequently inserted into bacmid DNA by homologous recombination. Following generation of a viral stock, Sf9 cells were superinfected. 48 hours later, the recombinant fusion protein was purified from cell lysates using an anti-FLAG™ M2 MAb affinity matrix (Sigma).

C. Immunization of Mice 8 week old female BALB/c mice (IFFA CREDO) were immunized as described above in Example 1, subsection C.

D. Specific Serum Titrations

Mice serum titrations were performed as described above in Example 1, subsection D.

E. B Cell/Myeloma Fusions

B cell extraction and cellular fusion were performed and analyzed as described above in Example 9, subsection D.

F. Hybridoma Screening

Hybridoma screening was performed as described above in Example 1, subsection F.

G. Monoclonal Antibody Specificity

The specificity of the 7E3 monoclonal antibody was determined as described above in Example 1, subsection G.

H. Cellular Assay 1

Monoclonal antibody was first purified from hybridoma cell supernatant using protein G affinity chromatography.

Cellular Assay I was performed as described above in Example 1, subsection J.

I. Cellular Assay 2

Cellular Assay II was performed as described above in Example 1, subsection K.

J. 7E3 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from the 7E3 clone was generated by RT-PCR with the mouse ScFv module (Amersham Biosciences) according to the manufacturer's guidelines. Amplified products were cloned into the pGEM-T easy vector (Promega Corp.) and sequenced using the T7 and SP6 primers.

The VH and VL cDNAs were subsequently cloned in mammalian expression vectors containing the human IgG1 and human kappa constant regions respectively in order to express 7E3 as a chimeric MAb ("chimeric 7E3"). To produce recombinant chimeric MAb, HEK 293 cells were plated in 6 well plates at a density of 2.5×10$^5$ cells/well in 2 ml culture medium containing 10% FBS. 16 hours post-plating, cells were transfected with 0.75 µg of the appropriate vector(s) using Fugene™ reagent (Roche) according to the manufacturer's guidelines. 48 hours post-transfection, supernatant was harvested and antibody was purified using protein G affinity chromatography.

Example 24

Generation of MAbs Directed Against the Human TLR4/MD-2 Complex

Figure 21:
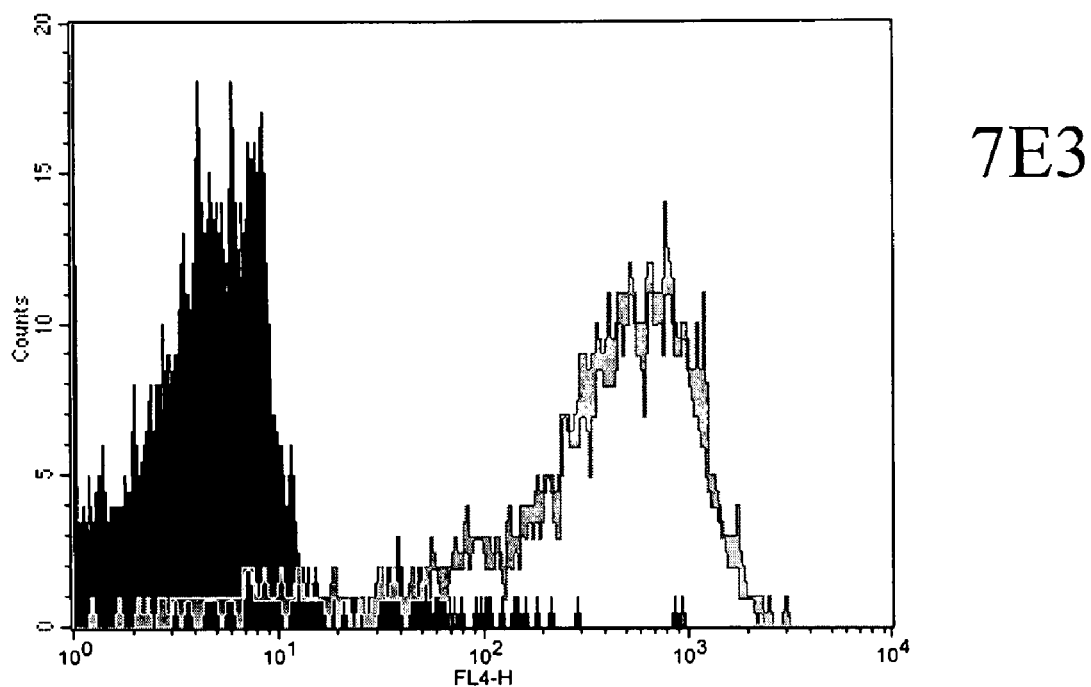
FIG. 21 is a graph depicting the binding of a monoclonal antibody of the invention, 7E3, to the TLR4/MD-2 complex. Specificity of binding is shown by flow cytometry using mock transfected or TLR4/MD-2 transfected cells. The results using mock-transfected cells are shown in the filled graph (left), while the results using TLR4/MD-2 transfected cells are shown as in the outline graph (right).

Mice immunized with CHO cells expressing surface TLR4/MD-2 were monitored for specific serum titers. Those showing a response to TLR4/MD-2 were "hyperboosted" with HEK 293 TLR4/MD-2 transfectants. This strategy was chosen in order to minimize the response to non-specific CHO cellular antigens, while simultaneously maximizing the TLR4/MD-2-specific response. Screening by FACS of supernatants from hybridomas resulting from B cell/myeloma fusions was performed on mock transfected vs. TLR4/MD-2 transfected CHO cells. Monoclonal antibody from a specific clone, referred to herein as 7E3, demonstrated specific binding to TLR4/MD-2 transfected CHO cells (FIG. 21). 7E3 was found to have the IgG1 κ isotype, as determined by FACS using the mouse Ig isotyping CBA kit (Beckton Dickenson).

Example 25

Neutralization of LPS Activity on TLR4/MD-2 Transfected HEK 293 Cells

Figure 22:
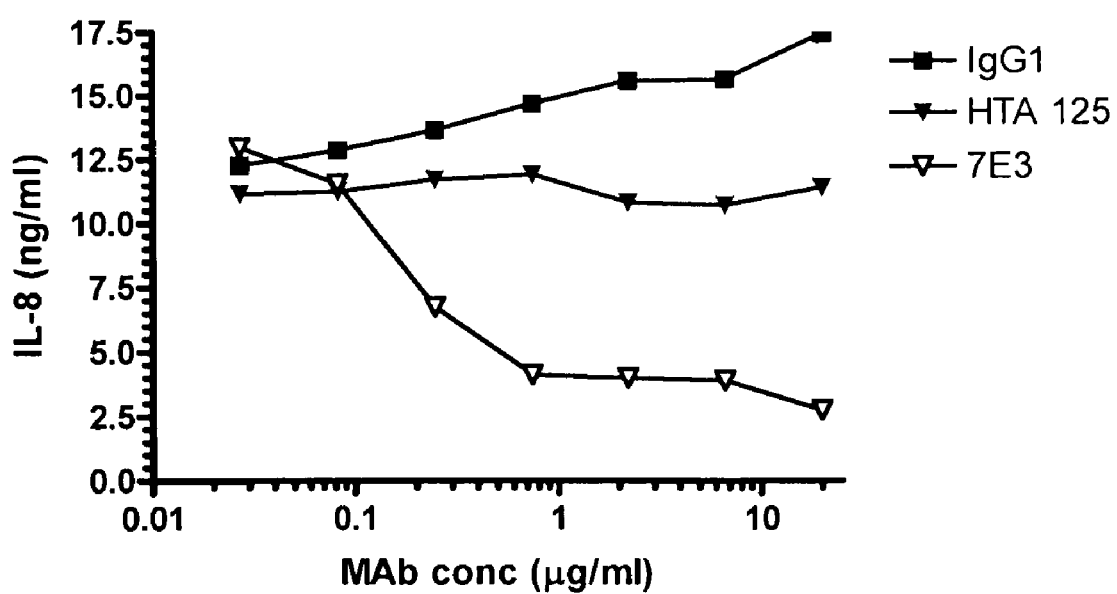
FIG. 22 is a graph depicting inhibition of lipopolysaccharide (LPS)-induced IL-8 production in TLR4/MD-2 transfected HEK 293 cells by the monoclonal antibody 7E3. The cells were incubated with the 7E3 monoclonal antibody, HTA 125 (anti-human TLR4 non-blocking monoclonal antibody) and an isotype-matched control (IgG1) at the indicated concentrations and subsequently incubated with LPS (15 ng/ml). IL-8 levels were assessed 16 hours post LPS treatment.

LPS is known to have ability to induce IL-8 production in HEK 293 cells transfected with the TLR4/MD-2 complex. The ability of 7E3 to inhibit this IL-8 induction was analyzed by pre-incubating cells with each antibody for 30 minutes prior to LPS administration. FIG. 22 shows that 7E3 inhibited the effects of LPS on HEK 293 cells, even at sub-microgram/ml concentrations.

Example 26

Neutralization of LPS Activity on Human Whole Blood

The ability of 7E3 to inhibit LPS-induced IL-8 production in human whole blood was tested. 7E3 neutralizing activity was tested in blood from 3 different donors using a range of monoclonal antibody concentrations from 0.5 to 5 µg/ml. FIG. 23 demonstrates that 7E3 significantly reduced the level of IL-8 induced by LPS in all 3 donors, as compared to an isotype matched control. 7E3 was found to be more potent than a previously described α-TLR4 blocking monoclonal antibody (purchased from e-biosciences). (See Shimazu et al. J. Exp. Med. 189: 1777-1782 (1999)). In some cases, 7E3 was found to be as potent as an α-CD14 blocking monoclonal antibody that was also included in the study. (See Kirkland et al. J. Biol. Chem. 268: 24818-24823 (1993)). These results indicate that the neutralizing epitope recognized by 7E3 on transfected HEK 293 cells is also exposed on the surface on cells in whole blood, and that 7E3 is potent enough to inhibit the activity of LPS in whole blood, even at concentrations below 1 µg/ml.

Example 27

7E3 Specificity

Figure 24:
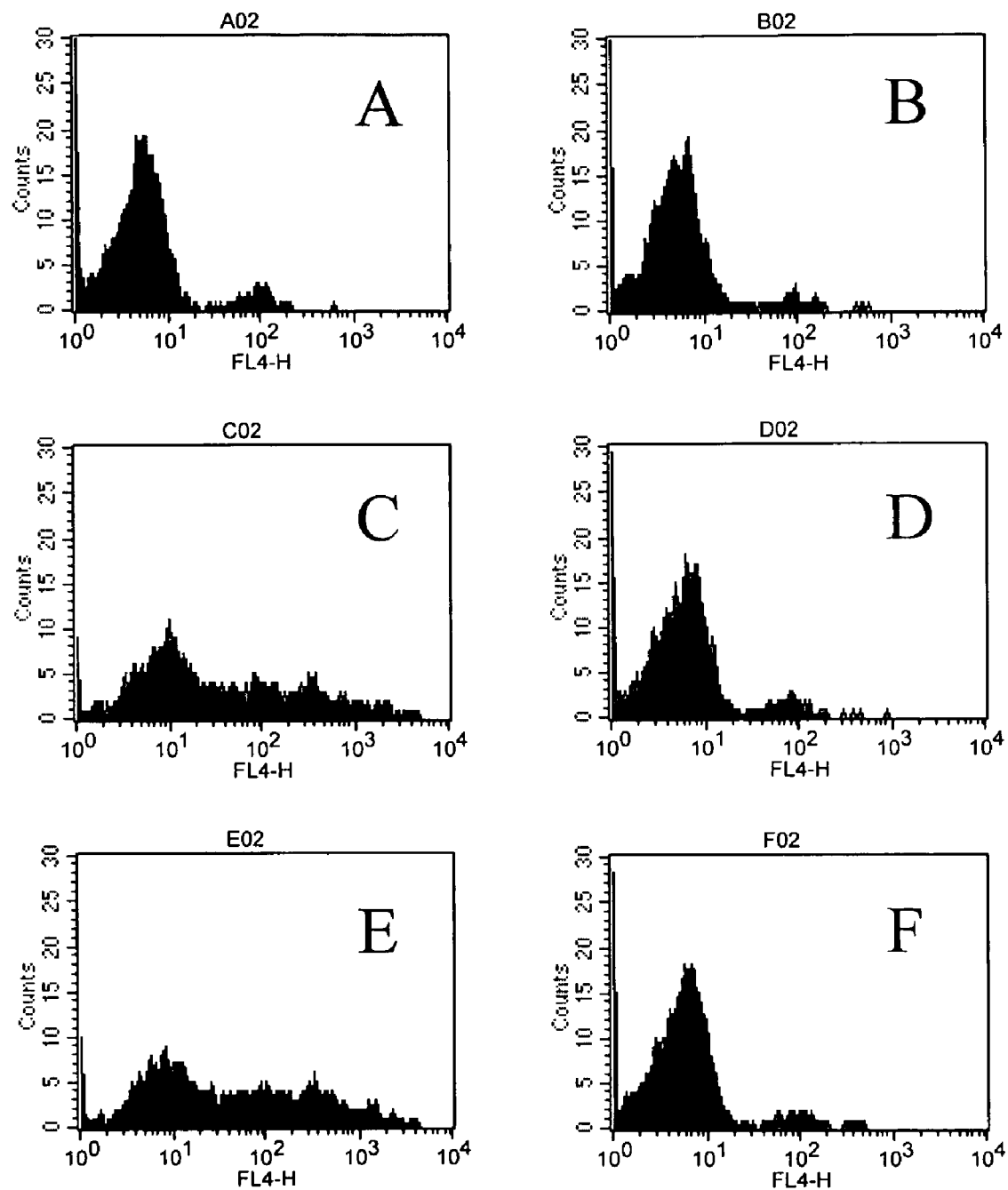
FIG. 24 is a series of graphs depicting the specificity of the 7E3 monoclonal antibody for the TLR4/MD-2 complex. The specificity of the 7E3 antibody is shown by flow cytometry analysis of HEK 293 cells transiently transfected with either mock vector (Panel A), human TLR4 (Panel B), human TLR4 and human MD-2 (Panel C), rabbit TLR4 and rabbit MD-2 (Panel D), human TLR4 and rabbit MD-2 (Panel E), or rabbit TLR4 and human MD-2 (Panel F). Cells were incubated with the 7E3 monoclonal antibody (10 μg/ml), followed by an APC-coupled α-mouse (H+L) antibody.

In order to determine the specificity of the 7E3 monoclonal antibody, the fact that 7E3 does not recognize the rabbit ortholog of the TLR4/MD-2 complex (previously cloned) was exploited. cDNAs for either rabbit or human TLR4 with N-terminal FLAG™ epitope tag and MD-2 with C-terminal c-Myc and protein C epitope tags were transfected in HEK 293 cells in the following combinations: (1) mock vector (2) human TLR4 alone (3) human TLR4 and human MD-2 (4) rabbit TLR4 and rabbit MD-2; (5) human TLR4 and rabbit MD-2; (6) rabbit TLR4 and human MD-2. FIG. 24 shows FACS analysis of these cells following antibody staining, which revealed that 7E3 recognized cells expressing the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by 7E3 is situated human TLR4 but the presence of MD-2 is essential for MAb binding (FIG. 24).

Example 28

7E3 VH and VL Sequences

VH and VL sequences from the 7E3 hybridoma clone were amplified from total RNA by RT-PCR. Sequence analysis is shown in FIGS. 25A-25F.

The 7E3 antibody includes a heavy chain variable region (SEQ ID NO:32, FIG. 25B) encoded by the nucleic acid sequence of SEQ ID NO:31 shown in FIG. 25A, and a light chain variable region (SEQ ID NO:37, FIG. 25E) encoded by the nucleic acid sequence of SEQ ID NO:36 shown in FIG. 25D. The amino acids encompassing the CDR as defined by Chothia et al. 1989, E. A. Kabat et al., 1991 are highlighted in underlined and italicized text in FIGS. 25B and 25E and shown in FIGS. 25C and 25F. The heavy chain CDRs of the 7E3 antibody have the following sequences: TYNIGVG (SEQ ID NO:33); HIWWNDNIYYNTVLKS (SEQ ID NO:34); and MAEGRYDAMDY (SEQ ID NO:35). The light chain CDRs of the 7E3 antibody have the following sequences: RASQDITNYLN (SEQ ID NO:38); YTSKLHS (SEQ ID NO:39); and QQGNTFPWT (SEQ ID NO:40).

Example 29

Chimeric 7E3 Binds to hTLR4 hMD2 Transfected CHO Cells

Figure 26:
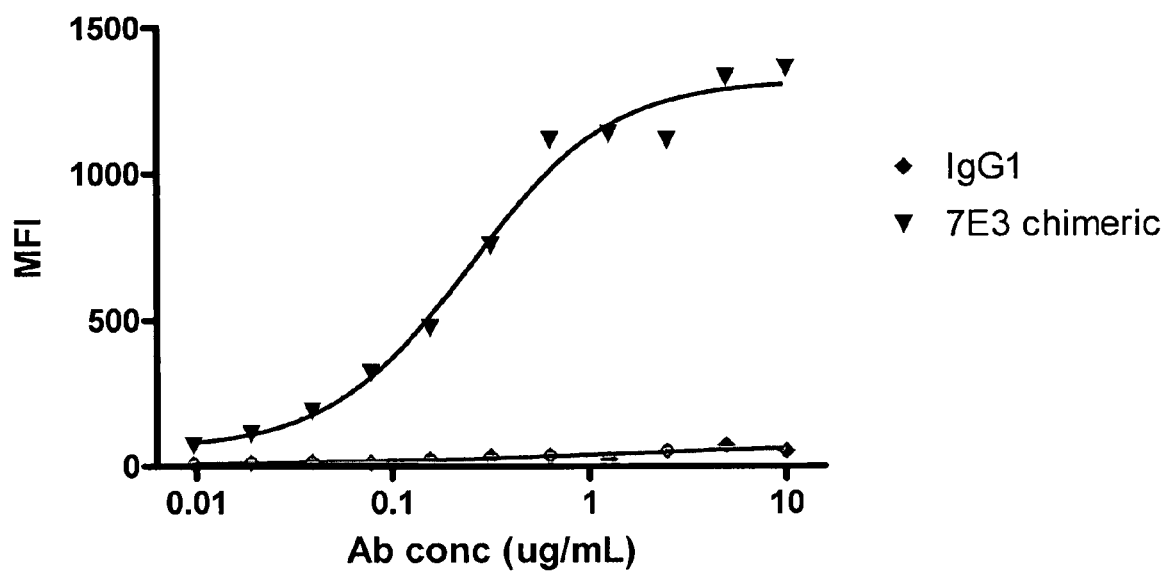
FIG. 26 is a graph illustrating that the VH and VL nucleotide sequence of 7E3 expressed as a chimeric MAb ("chimeric 7E3") is capable of binding specifically to the human TLR4/MD-2 complex on the surface of transfected CHO cells. Monoclonal antibody binding to TLR4/MD-2 transfected CHO cells is shown by flow cytometry using chimeric 7E3 or an isotype matched control MAb at the indicated concentrations.

In order to demonstrate the specificity of the cloned 7E3 VH and VL for the hTLR4/MD-2 complex, FACS analysis on hTLR4/MD-2 transfected CHO cells using the chimeric 7E3 MAb was performed (FIG. 26). Specific binding of MAb at the indicated concentration was detected using an APC-labeled goat-anti-human IgG (H+L) secondary antibody. An irrelevant isotype-matched IgG1 MAb was used as a control.

Example 30

Figure 27:
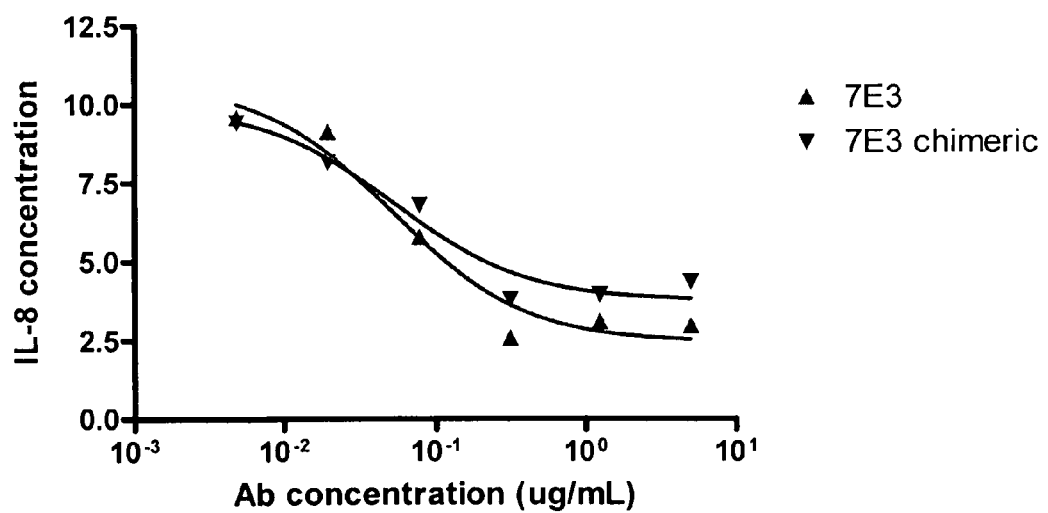
FIG. 27 is a graph depicting inhibition of lipopolysaccharide (LPS)-induced IL-8 production in TLR4/MD-2 transfected HEK 293 cells by the chimeric 7E3 MAb. Cells were incubated with chimeric 7E3 or an isotype matched MAb control at the indicated concentrations and subsequently incubated with LPS (15 ng/ml). IL-8 levels were assessed 16 hours post LPS-treatment.

Chimeric 7E3 Inhibits LPS-Induced IL-8 Production in hTLR4 hMD2 Transfected HEK 293 Cells In order to demonstrate the neutralizing capacity of the cloned 7E3 VH and VL for LPS, the ability of 7E3 to inhibit LPS dependent IL-8 induction of hTLR4/MD-2 transfected HEK 293 cells was tested as described above. FIG. 27 shows that chimeric 7E3 inhibited the effects of LPS on HEK 293 cells.

Example 31

Construction of TLR4/MD-2 Fusion Protein cDNA and Cloning into pFASTBAC1

Figure 28:
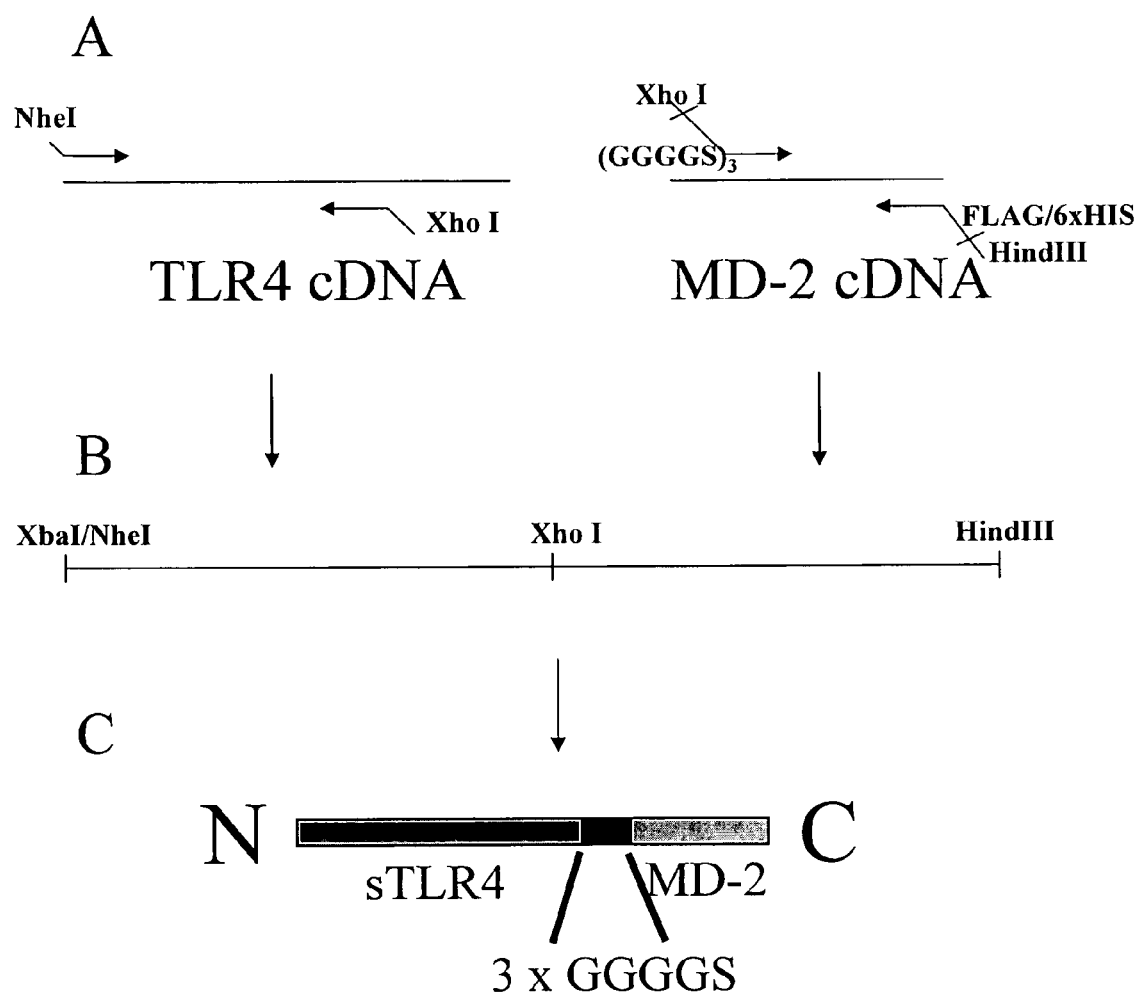
FIG. 28 is an illustration depicting the construction of a TLR4/MD-2 fusion protein cDNA according to the present invention.

The extracellular portion of TLR4 linked to MD-2 via a glycine serine (GGGGS$_3$) linker was assembled using PCR. FLAG and 6×HIS tags were included at the C-terminus of MD-2 for detection and purification purposes. (FIG. 28).

FIGS. 28A-C illustrate the construction of this TLR4/MD-2 fusion protein cDNA according to the present invention. cDNA encoding the extracellular portion of human TLR4 (sTLR4) was amplified by PCR, and unique NheI/XhoI restriction sites were introduced into 5' non-annealing primer extensions. The (GGGGS)$_3$ coding sequence and unique XhoI site was introduced into the 5' non-annealing extension of the sense primer, and a unique HindIII site was introduced into the 5' non-annealing extension of the antisense primer. (Panel A). Panel B depicts the sequential cloning of the amplified sTLR4 and (GGGGS)$_3$/MD-2 cDNAs into pFASTBAC1 between the unique XbaI and HindIII restriction site. Panel C depicts a proposed protein product following expression of the sTLR4/MD-2 cDNA in Sf9 cells.

Example 32

Expression of the TLR4/MD-2 Chimeric Protein in SF9 Cell Lysates and Supernatants The cDNA cassette of Example 1 was cloned into the baculovirus expression vector pFASTBAC1 (Invitrogen) and subsequently inserted into bacmid DNA by homologous recombination. Following generation of a viral stock, Sf9 cells were superinfected and expression of the TLR4/MD-2 fusion protein was analyzed in the cell lysate at 48 and 72 hours post infection by Western blotting. (FIG. 29).

Figure 29:
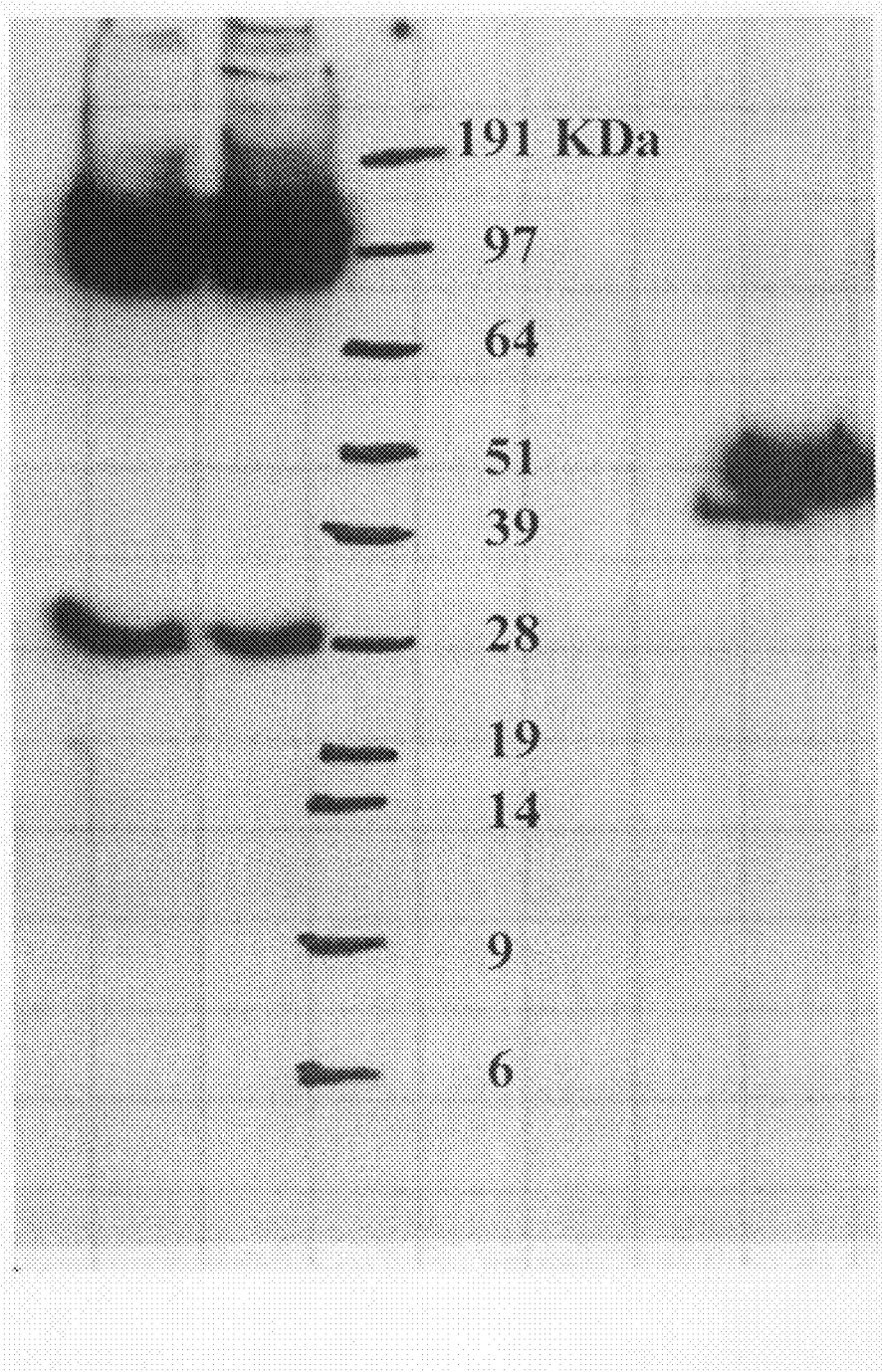
FIG. 29 is an illustration depicting the expression of a TLR4/MD-2 chimeric protein of the invention in Sf9 cell lysates and supernatant.

FIG. 29 demonstrates the expression of a TLR4/MD-2 chimeric protein of the invention in Sf9 cell lysates and supernatants. Protein expression in the Sf9 cell lysates and supernatants was detected by Western blotting using the anti-FLAG M2 antibody: Lane 1 depicts cleared lysate at 48 hours post infection; lane 2 depicts cleared lysate at 72 hours post infection; lane 3 depicts cleared supernatant at 48 hours post infection; lane 4 depicts cleared supernatant at 72 hours post infection; and lane 5 contains a reference protein (FLAG tagged). The molecular weight marker sizes in FIG. 29 are shown in KDa. The predicted molecular weight of TLR4/MD-2 chimeric protein is approximately 90 KDa, and the appearance of probable degradation product occurs at approximately 28 KDa.

Example 33

Purification of the TLR4/MD-2 Chimeric Protein from Infected SF9 Cell Lysates

To purify the fusion protein, Sf9 cells were harvested 48 hours post superinfection and lysed in 20 mM Tris pH7.4, 150 mM NaCl, 1% NP40 with COMPLETE™ protease inhibitors (Roche) at a concentration of 5 volumes/gram cells. Following a fifteen hour (15') incubation at 4° C., lysates were cleared by centrifugation (4000 rpm) and filtration (0.22 μm) and passed through an anti-FLAG M2 MAb affinity matrix (Sigma). Unbound protein was removed from the matrix by successive washing with 20 mM Tris (pH 7.4), 150 mM NaCl, 1% NP40 and 20 mM Tris (pH 7.4), 150 mM NaCl. Bound protein was eluted from the column with 100 mM glycine (pH 2.75) and collected in 0.5 ml fractions. Fractions were rapidly brought to neutral pH through the addition of 50 μl of 1M Tris (pH 9). Protein content was analyzed by western blotting (with peroxidase conjugated anti-FLAG M2) and Coomassie brilliant blue staining. (FIG. 30).

Figure 30:
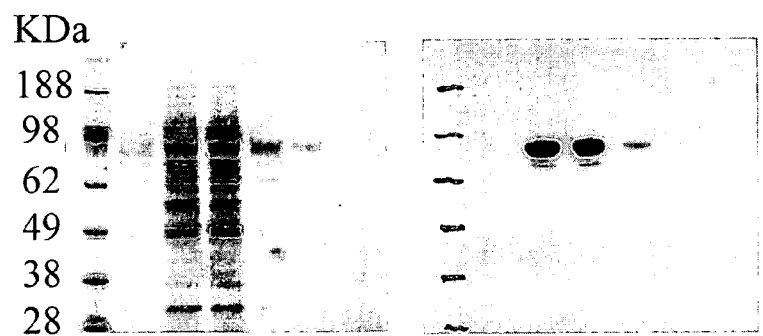
FIG. 30 is an illustration depicting the purification of a TLR4/MD-2 chimeric protein according to the invention from infected Sf9 cell lysates.

FIG. 30 demonstrates the presence of purified TLR4/MD-2 chimeric protein in infected Sf9 cell lysates. Protein in the cell lysates was detected by Coomassie brilliant blue staining (FIG. 30, left panel) or Western blotting (FIG. 30, right panel) using the anti-FLAG M2 antibody. Lanes 1-5 depict 0.5 ml eluted fractions from the anti-FLAG M2 affinity column.

Example 34

Inhibition of LPS Induced IL-8 Production Using Chimeric Soluble TLR4/MD-2

Figure 31:
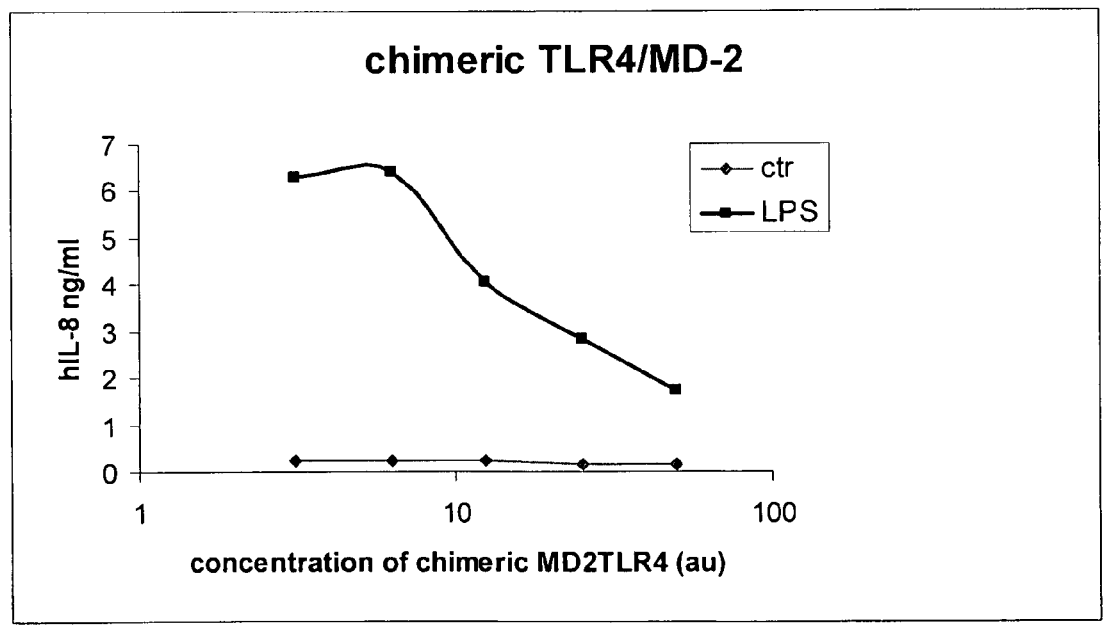
FIG. 31 is a graph depicting the inhibit of lipopolysaccharide-(LPS) induced IL-8 production using a soluble chimeric TLR4/MD-2 protein according to the present invention.

Lipopolysaccharide (LPS) (15 ng/ml) was preincubated with a purified chimeric TLR4/MD-2 according to the present invention at varying concentrations and subsequently incubated with TLR4/MD-2 transfected HEK 293 cells. FIG. 31 is a graph depicting IL-8 production in the cell culture medium 24 hours post treatment.

As seen in FIG. 31, purified chimeric TLR4/MD-2 was shown to have an inhibitory effect on the LPS-induced IL-8 production in TLR4/MD-2 transfected HEK cells, thereby indicating that the purified TLR4/MD-2 protein of the invention was at least partially conformationally correct.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of alleviating a symptom of a pathology associated with TLR4 activation, the method comprising administering an isolated antibody that binds a human Toll-like receptor 4 (TLR4)/human MD-2 complex to a subject in which such alleviation is desired in an amount sufficient to alleviate the symptom of the pathology in the subject, wherein the antibody comprises a heavy chain with three complementarity determining regions (CDRs) comprising a CDR1 region comprising an amino acid sequence comprising GGYSWH (SEQ ID NO:23); a CDR2 region comprising an amino acid sequence comprising YIHYSGYTDFNPSLKT (SEQ ID NO:24); and a CDR3 region comprising an amino acid sequence comprising KDPSDGFPY (SEQ ID NO:25); and a light chain with three CDRs comprising a CDR1 region comprising an amino acid sequence comprising RASQSIS-DHLH (SEQ ID NO:28); a CDR2 region comprising an amino acid sequence comprising YASHAIS (SEQ ID NO:29); and a CDR3 region comprising an amino acid sequence comprising QNGHSFPLT (SEQ ID NO:30); and wherein the antibody inhibits at least 50% of lipopolysaccharide (LPS)-induced IL-8 production in a solution comprising human TLR4/MD-2 transfected HEK293 cells when said antibody is added to said solution at a concentration of 10 µg/ml, as compared to the level of LPS-induced IL-8 production in the absence of said antibody.

2. The method of claim 1, wherein the antibody is an antibody selected from an antibody that does not bind to a human MD-2 protein when said MD-2 protein is not complexed to human TLR4, an antibody that binds soluble human TLR4, an antibody that binds human TLR4 on a cell surface, a monoclonal antibody, a humanized antibody, and combinations thereof.

3. The method of claim 1, wherein said antibody comprises a heavy chain variable amino acid sequence comprising SEQ ID NO: 22.

4. The method of claim 1, wherein said antibody comprises a light chain variable amino acid sequence comprising SEQ ID NO: 27.

5. The method of claim 1, wherein said antibody comprises a heavy chain variable amino acid sequence comprising SEQ ID NO: 22 and a light chain variable amino acid sequence comprising SEQ ID NO: 27.

6. The method of claim 1, wherein the subject is a human.

7. The method of claim 1, wherein said pathology is an autoimmune disease.

8. The method of claim 1, wherein said pathology is selected from the group consisting of sepsis, ventilator-induced lung injury, acute inflammation, chronic inflammation, and diseases and disorders induced by endogenous soluble stress factors wherein said endogenous soluble stress factors are induced by mechanical stress.

9. The method of claim 8, wherein said chronic inflammation is associated with an allergic condition, or asthma.

10. The method of claim 8, wherein said pathology is inflammatory bowel disorder or atherosclerosis.

11. The method of claim 8, wherein said disorder induced by endogenous soluble stress factors is osteoarthritis or rheumatoid arthritis.

12. The method of claim 8, wherein said endogenous soluble stress factor is Hsp60, fibronectin, heparan sulphate, hyaluronan, gp96, β-Defensin-2 or surfactant protein A.

* * * * *

SEQUENCE LISTING

<160> NUMBER OF SEQ ID NOS: 44

<210> SEQ ID NO 1
<211> LENGTH: 360
<212> TYPE: DNA
<213> ORGANISM: Mus musculus

<400> SEQUENCE: 1
caggtgcaac tgcagcagtc tggggctgat cttgtgaggc caggggcctt agtcaagttg       60
tcctgcacag cttctggctt caacattaaa gactccatata tacactgggt gaagaagagg     120
cctgaatggg gcctggagtg gattggatgg actgatcctg agaatgttaa ttctatatat     180
gacccgaggt ttcagggcaa ggccagtata acagcagaca catcctccaa cacagccttc     240
cttcagctca ccagcctgac atctgaggac actgccgtct attactgtgc tagggggttat     300 aacggtgttt actatgctat ggactactgg ggccaaggga cctcagtcac cgtctcctca     360

<210> SEQ ID NO 2
<211> LENGTH: 120
<212> TYPE: PRT
<213> ORGANISM: Mus musculus

<400> SEQUENCE: 2

Gln Val Gln Leu Gln Gln Ser Gly Ala Asp Leu Val Arg Pro Gly Ala
1               5                   10                  15

Leu Val Lys Leu Ser Cys Thr Ala Ser Gly Phe Asn Ile Lys Asp Ser
            20                  25                  30

Tyr Ile His Trp Val Lys Lys Arg Pro Glu Trp Gly Leu Glu Trp Ile
        35                  40                  45

Gly Trp Thr Asp Pro Glu Asn Val Asn Ser Ile Tyr Asp Pro Arg Phe
    50                  55                  60

Gln Gly Lys Ala Ser Ile Thr Ala Asp Thr Ser Ser Asn Thr Ala Phe
65                  70                  75                  80

Leu Gln Leu Thr Ser Leu Thr Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Thr Val Thr Val Ser Ser
        115                 120

<210> SEQ ID NO 3
<211> LENGTH: 5
<212> TYPE: PRT
<213> ORGANISM: Mus musculus

<400> SEQUENCE: 3

Asp Ser Tyr Ile His
1               5

<210> SEQ ID NO 4
<211> LENGTH: 17
<212> TYPE: PRT
<213> ORGANISM: Mus musculus

<400> SEQUENCE: 4

Trp Thr Asp Pro Glu Asn Val Asn Ser Ile Tyr Asp Pro Arg Phe Gln
1               5                   10                  15

Gly

<210> SEQ ID NO 5
<211> LENGTH: 11
<212> TYPE: PRT
<213> ORGANISM: Mus musculus

<400> SEQUENCE: 5

Gly Tyr Asn Gly Val Tyr Tyr Ala Met Asp Tyr
1               5                   10

<210> SEQ ID NO 6
<211> LENGTH: 321
<212> TYPE: DNA
<213> ORGANISM: Mus musculus

<400> SEQUENCE: 6

```
caaattgttc tcacccagtc tccatcaatc atgtctgcgt ctctagggga ggagatcacc      60
ctaacctgca gtgccagctc gagtgtaatt tacatgcact ggtaccagca aaagtcaggc    120
acttctccca aactcttgat ttataggaca tacaacctgg cttctggagt cccttctcgc    180
ttcagtggca gtgggtctgg gacctttat tctctcacaa tcagcagtgt ggaggctgaa     240
gatgctgccg attattactg ccatcagtgg agtagttttc cgtacacgtt cggaggggg     300
accaagctgg aaatcaaacg g                                              321
```

<210> SEQ ID NO 7
<211> LENGTH: 107
<212> TYPE: PRT
<213> ORGANISM: Mus musculus

<400> SEQUENCE: 7

Gln Ile Val Leu Thr Gln Ser Pro Ser Ile Met Ser Ala Ser Leu Gly
1               5                   10                  15

Glu Glu Ile Thr Leu Thr Cys Ser Ala Ser Ser Val Ile Tyr Met
            20                  25                  30

His Trp Tyr Gln Gln Lys Ser Gly Thr Ser Pro Lys Leu Leu Ile Tyr
        35                  40                  45

Arg Thr Tyr Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Phe Pro Tyr Thr
                85                  90                  95

Phe Gly Gly Gly Thr Lys Leu Glu Ile Lys Arg
            100                 105

<210> SEQ ID NO 8
<211> LENGTH: 10
<212> TYPE: PRT
<213> ORGANISM: Mus musculus

<400> SEQUENCE: 8

Ser Ala Ser Ser Ser Val Ile Tyr Met His
1               5                   10

<210> SEQ ID NO 9
<211> LENGTH: 7
<212> TYPE: PRT
<213> ORGANISM: Mus musculus

<400> SEQUENCE: 9

Arg Thr Tyr Asn Leu Ala Ser
1               5

<210> SEQ ID NO 10
<211> LENGTH: 9
<212> TYPE: PRT
<213> ORGANISM: Mus musculus

<400> SEQUENCE: 10

His Gln Trp Ser Ser Phe Pro Tyr Thr
1               5

<210> SEQ ID NO 11
<211> LENGTH: 353
<212> TYPE: DNA
<213> ORGANISM: Mus musculus

<400> SEQUENCE: 11

```
aggtgaaact gcaggagtct ggagctgagc tgatgaagcc tggggcctca gtgaagatat      60
cctgcaaggc tactggctac aaattcagtg actactggat agagtggata aaacagaggc     120
ctggacatgg ccttgagtgg attggagaga ttttgcctgg aagtggtagt actaactaca     180
atgaggactt caaggacaag gccacattca cttcagatac atcctccaac acagcctaca     240
tgcaactcag cagcctgaca tctgaagact ctgccgtcta ttactgtgca aaagaggaga     300
gggcgtacta ctttggctat tggggccaag ggaccacggt caccgtctcc tca            353
```

<210> SEQ ID NO 12
<211> LENGTH: 118
<212> TYPE: PRT
<213> ORGANISM: Mus musculus

<400> SEQUENCE: 12

Gln Val Lys Leu Gln Glu Ser Gly Ala Glu Leu Met Lys Pro Gly Ala
1               5                   10                  15

Ser Val Lys Ile Ser Cys Lys Ala Thr Gly Tyr Lys Phe Ser Asp Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Ser Thr Asn Tyr Asn Glu Asp Phe
    50                  55                  60

Lys Asp Lys Ala Thr Phe Thr Ser Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Lys Glu Glu Arg Ala Tyr Tyr Phe Gly Tyr Trp Gly Gln Gly Thr
            100                 105                 110

Thr Val Thr Val Ser Ser
        115

<210> SEQ ID NO 13
<211> LENGTH: 5
<212> TYPE: PRT
<213> ORGANISM: Mus musculus

<400> SEQUENCE: 13

Asp Tyr Trp Ile Glu
1               5

<210> SEQ ID NO 14
<211> LENGTH: 17
<212> TYPE: PRT
<213> ORGANISM: Mus musculus

<400> SEQUENCE: 14

Glu Ile Leu Pro Gly Ser Gly Ser Thr Asn Tyr Asn Glu Asp Phe Lys
1               5                   10                  15
Asp

<210> SEQ ID NO 15
<211> LENGTH: 9
<212> TYPE: PRT
<213> ORGANISM: Mus musculus

<400> SEQUENCE: 15

Glu Glu Arg Ala Tyr Tyr Phe Gly Tyr
1               5

<210> SEQ ID NO 16
<211> LENGTH: 339
<212> TYPE: DNA
<213> ORGANISM: Mus musculus

<400> SEQUENCE: 16
gatgttttga tgacccaaac tccactctcc ctgcctgtca gtcttggaga tcaagcctcc      60
atctcttgca ggtctagtca gagccttgaa acagtaatg gaaacaccta tttgaactgg     120
tacctccaga aaccaggcca gtctccacag ctcctgatct acagggtttc caaccgattt     180
tctggggtcc tagacaggtt cagtggtagt ggatcaggga cagatttcac actgaaaatc     240
agcagagtgg aggctgagga tttgggagtt tatttctgcc tccaagttac acatgtccct     300
cccacgttcg gtgctgggac caagctggaa ctgaaacgg                            339

<210> SEQ ID NO 17
<211> LENGTH: 113
<212> TYPE: PRT
<213> ORGANISM: Mus musculus

<400> SEQUENCE: 17

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr Phe Gly Ala Gly Thr Lys Leu Glu Leu Lys
            100                 105                 110

Arg

<210> SEQ ID NO 18
<211> LENGTH: 16
<212> TYPE: PRT
<213> ORGANISM: Mus musculus

<400> SEQUENCE: 18

Arg Ser Ser Gln Ser Leu Glu Asn Ser Asn Gly Asn Thr Tyr Leu Asn
1               5                   10                  15

<210> SEQ ID NO 19
<211> LENGTH: 7
<212> TYPE: PRT
<213> ORGANISM: Mus musculus

<400> SEQUENCE: 19

Arg Val Ser Asn Arg Phe Ser
1               5

<210> SEQ ID NO 20
<211> LENGTH: 9
<212> TYPE: PRT
<213> ORGANISM: Mus musculus

<400> SEQUENCE: 20

Leu Gln Val Thr His Val Pro Pro Thr
1               5

<210> SEQ ID NO 21
<211> LENGTH: 354
<212> TYPE: DNA
<213> ORGANISM: Mus musculus

<400> SEQUENCE: 21
gatgtgcagc ttcaggagtc aggacctgac ctaatacaac cttctcagtc actttcactc    60
acctgcactg tcactggcta ctccatcacc ggtggttata gctggcactg gatccggcag   120
tttccaggaa acaaactgga atggatgggc tacatccact acagtggtta cactgacttc   180
aaccctctc tcaaaactcg aatctctatc actcgagaca catccaagaa ccagttcttc   240
ctgcagttga attctgtgac tactgaagac acagccacat attactgtgc aagaaaagat   300
ccgtccgacg gatttcctta ctggggccaa gggactctgg tcactgtctc tgca          354

<210> SEQ ID NO 22
<211> LENGTH: 118
<212> TYPE: PRT
<213> ORGANISM: Mus musculus

<400> SEQUENCE: 22

Asp Val Gln Leu Gln Glu Ser Gly Pro Asp Leu Ile Gln Pro Ser Gln
1               5                   10                  15

Ser Leu Ser Leu Thr Cys Thr Val Thr Gly Tyr Ser Ile Thr Gly Gly
                20                  25                  30

Tyr Ser Trp His Trp Ile Arg Gln Phe Pro Gly Asn Lys Leu Glu Trp
            35                  40                  45

Met Gly Tyr Ile His Tyr Ser Gly Tyr Thr Asp Phe Asn Pro Ser Leu
        50                  55                  60

Lys Thr Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ala
        115

<210> SEQ ID NO 23
<211> LENGTH: 6
<212> TYPE: PRT
<213> ORGANISM: Mus musculus

<400> SEQUENCE: 23

Gly Gly Tyr Ser Trp His
1               5

<210> SEQ ID NO 24
<211> LENGTH: 16
<212> TYPE: PRT
<213> ORGANISM: Mus musculus

<400> SEQUENCE: 24

Tyr Ile His Tyr Ser Gly Tyr Thr Asp Phe Asn Pro Ser Leu Lys Thr
1               5                   10                  15

<210> SEQ ID NO 25
<211> LENGTH: 9
<212> TYPE: PRT
<213> ORGANISM: Mus musculus

<400> SEQUENCE: 25

Lys Asp Pro Ser Asp Gly Phe Pro Tyr
1               5

<210> SEQ ID NO 26
<211> LENGTH: 321
<212> TYPE: DNA
<213> ORGANISM: Mus musculus

<400> SEQUENCE: 26
gacattgtga tgacccagtc tccagccacc ctgtctgtga ctccaggtga tagagtctct     60
ctttcctgca gggccagcca gagtatcagc gaccacttac actggtatca acaaaaatca    120
catgagtctc cacggcttct catcaaatat gcttcccatg ccatttctgg gatcccctcc    180
aggttcagtg gcagtggatc aggacagat ttcactctca gcatcaaaag tgtggaacct    240
gaagatattg ggtgtatta ctgtcaaaat ggtcacagtt ttccgctcac gttcggtgct    300
gggaccaagc tggagctgaa a                                              321

<210> SEQ ID NO 27
<211> LENGTH: 108
<212> TYPE: PRT
<213> ORGANISM: Mus musculus

<400> SEQUENCE: 27

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp His
            20                  25                  30

Leu His Trp Tyr Gln Gln Lys Ser His Glu Ser Pro Arg Leu Leu Ile
        35                  40                  45

Lys Tyr Ala Ser His Ala Ile Ser Gly Ile Pro Ser Arg Phe Ser Gly
    50                  55                  60

Ser Gly Ser Gly Thr Asp Phe Thr Leu Ser Ile Lys Ser Val Glu Pro
65                  70                  75                  80

Glu Asp Ile Gly Val Tyr Tyr Cys Gln Asn Gly His Ser Phe Pro Leu
                85                  90                  95

Thr Phe Gly Ala Gly Thr Lys Leu Glu Leu Lys Arg
            100                 105

<210> SEQ ID NO 28
<211> LENGTH: 11
<212> TYPE: PRT
<213> ORGANISM: Mus musculus

<400> SEQUENCE: 28

Arg Ala Ser Gln Ser Ile Ser Asp His Leu His
1               5                   10

<210> SEQ ID NO 29
<211> LENGTH: 7
<212> TYPE: PRT
<213> ORGANISM: Mus musculus

<400> SEQUENCE: 29

Tyr Ala Ser His Ala Ile Ser
1               5

<210> SEQ ID NO 30
<211> LENGTH: 9
<212> TYPE: PRT
<213> ORGANISM: Mus musculus

<400> SEQUENCE: 30

Gln Asn Gly His Ser Phe Pro Leu Thr
1               5

<210> SEQ ID NO 31
<211> LENGTH: 363
<212> TYPE: DNA
<213> ORGANISM: Mus musculus

<400> SEQUENCE: 31
caggttactc tgaaagagtc tggccctggg atattgcagc cctcccagac cctcagtctg      60
acttgttctt tctctgggtt ttcactgacc acttataata taggagtagg ctggattcgt     120
cagccttcag ggaagggtct ggagtggctg gcacacattt ggtggaatga taatatttac     180
tataatacag tccttaagag ccgactcaca ttctccaagg atacctccaa caaccaggtt     240
ttcctcaaga tcgccagtgt ggacattgca gatactgcca catattactg tattcgaatg     300
gctgagggaa ggtacgacgc tatggactac tggggtcaag gaacctcagt caccgtctcc     360
tca                                                                   363

<210> SEQ ID NO 32
<211> LENGTH: 121
<212> TYPE: PRT
<213> ORGANISM: Mus musculus

<400> SEQUENCE: 32

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Asn Ile Gly Val Gly Trp Ile Arg Gln Pro Ser Gly Lys Gly Leu Glu
        35                  40                  45

Trp Leu Ala His Ile Trp Trp Asn Asp Asn Ile Tyr Tyr Asn Thr Val
    50                  55                  60

```
Leu Lys Ser Arg Leu Thr Phe Ser Lys Asp Thr Ser Asn Asn Gln Val
 65                  70                  75                  80

Phe Leu Lys Ile Ala Ser Val Asp Ile Ala Asp Thr Ala Thr Tyr Tyr
                 85                  90                  95

Cys Ile Arg Met Ala Glu Gly Arg Tyr Asp Ala Met Asp Tyr Trp Gly
            100                 105                 110

Gln Gly Thr Ser Val Thr Val Ser Ser
        115                 120
```

<210> SEQ ID NO 33
<211> LENGTH: 7
<212> TYPE: PRT
<213> ORGANISM: Mus musculus

<400> SEQUENCE: 33

```
Thr Tyr Asn Ile Gly Val Gly
1               5
```

<210> SEQ ID NO 34
<211> LENGTH: 16
<212> TYPE: PRT
<213> ORGANISM: Mus musculus

<400> SEQUENCE: 34

```
His Ile Trp Trp Asn Asp Asn Ile Tyr Tyr Asn Thr Val Leu Lys Ser
1               5                  10                  15
```

<210> SEQ ID NO 35
<211> LENGTH: 11
<212> TYPE: PRT
<213> ORGANISM: Mus musculus

<400> SEQUENCE: 35

```
Met Ala Glu Gly Arg Tyr Asp Ala Met Asp Tyr
1               5                  10
```

<210> SEQ ID NO 36
<211> LENGTH: 324
<212> TYPE: DNA
<213> ORGANISM: Mus musculus

<400> SEQUENCE: 36

```
gctatccaga tgacacagag tacatcctcc ctgtctgcct ctctgggaga cagagtcacc    60
atcaattgca gggcaagtca ggacatcacc aattatttaa attggtatca gcagaaacca   120
gatggaactg tcagactcct gatctattat acatcaaaat tacactcagg agccccatca   180
aggttcagtg gcgtgggtc tggaacagat tattctctca ccattagtaa cctggagcaa   240
gaggatattg ccacttactt ttgccaacag ggtaatacgt ttccgtggac gttcggtgga   300
ggcaccaaac tggaaatcaa acgt                                         324
```

<210> SEQ ID NO 37
<211> LENGTH: 108
<212> TYPE: PRT
<213> ORGANISM: Mus musculus

<400> SEQUENCE: 37

```
Ala Ile Gln Met Thr Gln Ser Thr Ser Ser Leu Ser Ala Ser Leu Gly
1               5                  10                  15

Asp Arg Val Thr Ile Asn Cys Arg Ala Ser Gln Asp Ile Thr Asn Tyr
            20                  25                  30
```

Leu Asn Trp Tyr Gln Gln Lys Pro Asp Gly Thr Val Arg Leu Leu Ile
            35                  40                  45

Tyr Tyr Thr Ser Lys Leu His Ser Gly Ala Pro Ser Arg Phe Ser Gly
        50                  55                  60

Arg Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg
            100                 105

<210> SEQ ID NO 38
<211> LENGTH: 11
<212> TYPE: PRT
<213> ORGANISM: Mus musculus

<400> SEQUENCE: 38

Arg Ala Ser Gln Asp Ile Thr Asn Tyr Leu Asn
1               5                   10

<210> SEQ ID NO 39
<211> LENGTH: 7
<212> TYPE: PRT
<213> ORGANISM: Mus musculus

<400> SEQUENCE: 39

Tyr Thr Ser Lys Leu His Ser
1               5

<210> SEQ ID NO 40
<211> LENGTH: 9
<212> TYPE: PRT
<213> ORGANISM: Mus musculus

<400> SEQUENCE: 40

Gln Gln Gly Asn Thr Phe Pro Trp Thr
1               5

<210> SEQ ID NO 41
<211> LENGTH: 866
<212> TYPE: DNA
<213> ORGANISM: Homo sapiens

<400> SEQUENCE: 41

```
ggcacgagcg gcacgagccc accatgaagg gtttcacagc cactctcttc ctctggactc      60
tgattttttcc cagctgcagt ggaggcggcg gtgggaaagc ctggcccaca cacgtggtct    120
gtagcgacag cggcttggaa gtgctctacc agagttgcga tccattacaa gattttggct    180
tttctgttga aaagtgttcc aagcaattaa aatcaaatat caacattaga tttggaatta    240
ttctgagaga ggacatcaaa gagcttttt ttgacctagc tctcatgtct caaggctcat     300
ctgttttgaa tttctcctat cccatctgtg aggcggctct gcccaagttt tctttctgtg    360
gaagaaggaa aggagagcag atttactatg ctgggcctgt caataatcct gaatttacta    420
ttcctcaggg agaataccag gttttgctgg aactgtacac tgaaaaacgg tccaccgtgg    480
cctgtgccaa tgctactatc atgtgctcct gactgtggcc tgtagcaaaa atcacagcca    540
gctgcatctc gtgggaccct caagctcctc tgactgaacc tacgtgggag gagaagcagt    600
ctgatgacag agagaggctc tacaaagaag cgccccaaa gagtgcagct gctaatttta     660
gtcccaggac cagacatccc cagactccac agatgtaatg aagtcccga atgtatctgt     720
```

```
ttctaaggag cctcttggca gtccttaagc agtcttgagg gtccatcctt tttctctaat    780
tggtcgcctc ccaccagact cacctgcttt tcaactttt aggagtgctt cctcacagtt    840
accaagaata aagaaagctg gccacc                                         866
```

```
<210> SEQ ID NO 42
<211> LENGTH: 162
<212> TYPE: PRT
<213> ORGANISM: Homo sapiens

<400> SEQUENCE: 42
```

Met Lys Gly Phe Thr Ala Thr Leu Phe Leu Trp Thr Leu Ile Phe Pro
1               5                   10                  15

Ser Cys Ser Gly Gly Gly Gly Lys Ala Trp Pro Thr His Val Val
            20                  25                  30

Cys Ser Asp Ser Gly Leu Glu Val Leu Tyr Gln Ser Cys Asp Pro Leu
        35                  40                  45

Gln Asp Phe Gly Phe Ser Val Glu Lys Cys Ser Lys Gln Leu Lys Ser
    50                  55                  60

Asn Ile Asn Ile Arg Phe Gly Ile Ile Leu Arg Glu Asp Ile Lys Glu
65                  70                  75                  80

Leu Phe Leu Asp Leu Ala Leu Met Ser Gln Gly Ser Ser Val Leu Asn
                85                  90                  95

Phe Ser Tyr Pro Ile Cys Glu Ala Ala Leu Pro Lys Phe Ser Phe Cys
            100                 105                 110

Gly Arg Arg Lys Gly Glu Gln Ile Tyr Tyr Ala Gly Pro Val Asn Asn
        115                 120                 125

Pro Glu Phe Thr Ile Pro Gln Gly Glu Tyr Gln Val Leu Leu Glu Leu
    130                 135                 140

Tyr Thr Glu Lys Arg Ser Thr Val Ala Cys Ala Asn Ala Thr Ile Met
145                 150                 155                 160

Cys Ser

```
<210> SEQ ID NO 43
<211> LENGTH: 624
<212> TYPE: DNA
<213> ORGANISM: Homo sapiens

<400> SEQUENCE: 43
ggcgggccgc tcccacttcg gcacgagggg cacgaggtaa atcttttctg cttactgaaa    60
aggaagagtc tgatgattag ttactgatcc tctttgcatt tgtaaagctt tggagatatt    120
gaatcatgtt accatttctg tttttttcca ccctgttttc ttccatattt actgaagctc    180
agaagcagta ttgggtctgc aactcatccg atgcaagtat tcatacacc tactgtgata     240 aaatgcaata cccaatttca attaatgtta accctgtat agaattgaaa ggatccaaag     300
gattattgca cattttctac attccaagga gagatttaaa gcaattatat ttcaatctct    360
atataactgt caacaccatg aatcttccaa agcgcaaaga agttatttgc cgaggatctg    420
atgacgatta ctcttttgc agagctctga agggagagac tgtgaataca acaatatcat    480
tctccttcaa gggaataaaa ttttctaagg gaaaatacaa atgtgttgtt gaagctattt    540
ctgggagccc agaagaaatg ctcttttgct tggagtttgt catcctacac caacctaatt    600
caaattagaa taaattgagt attt                                           624
```

```
<210> SEQ ID NO 44
```

-continued

```
<211> LENGTH: 160
<212> TYPE: PRT
<213> ORGANISM: Homo sapiens

<400> SEQUENCE: 44

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Gly Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
                100                 105                 110

Val Asn Thr Thr Ile Ser Phe Ser Phe Lys Gly Ile Lys Phe Ser Lys
            115                 120                 125

Gly Lys Tyr Lys Cys Val Val Glu Ala Ile Ser Gly Ser Pro Glu Glu
        130                 135                 140

Met Leu Phe Cys Leu Glu Phe Val Ile Leu His Gln Pro Asn Ser Asn
145                 150                 155                 160
```